(12) United States Patent
Ban et al.

(10) Patent No.: US 10,294,237 B2
(45) Date of Patent: May 21, 2019

(54) BICYCLIC HETEROCYCLIC AMIDE DERIVATIVE

(71) Applicant: Sumitomo Dainippon Pharma Co., Ltd., Osaka (JP)

(72) Inventors: Hitoshi Ban, Osaka (JP); Manabu Kusagi, Osaka (JP); Yosuke Takanashi, Osaka (JP); Futoshi Hasegawa, Osaka (JP)

(73) Assignee: Sumitomo Dainippon Pharma Co., Ltd., Osaka (JP)

( * ) Notice: Subject to any disclaimer, the term of this patent is extended or adjusted under 35 U.S.C. 154(b) by 0 days.

(21) Appl. No.: 15/738,734

(22) PCT Filed: Jun. 21, 2016

(86) PCT No.: PCT/JP2016/068424
§ 371 (c)(1),
(2) Date: Dec. 21, 2017

(87) PCT Pub. No.: WO2016/208592
PCT Pub. Date: Dec. 29, 2016

(65) Prior Publication Data
US 2018/0194773 A1    Jul. 12, 2018

(30) Foreign Application Priority Data

Jun. 22, 2015  (JP) ................................ 2015-125175

(51) Int. Cl.
| | | |
|---|---|---|
| C07D 491/056 | (2006.01) | |
| C07D 403/12 | (2006.01) | |
| C07D 405/14 | (2006.01) | |
| A61K 45/00 | (2006.01) | |
| A61K 31/4365 | (2006.01) | |
| A61K 31/437 | (2006.01) | |
| A61K 31/4375 | (2006.01) | |

(Continued)

(52) U.S. Cl.
CPC ........ *C07D 491/056* (2013.01); *A61K 31/437* (2013.01); *A61K 31/4365* (2013.01); *A61K 31/4375* (2013.01); *A61K 31/4709* (2013.01); *A61K 45/00* (2013.01); *A61P 35/02* (2018.01); *C07D 233/88* (2013.01); *C07D 401/12* (2013.01); *C07D 403/12* (2013.01); *C07D 405/12* (2013.01); *C07D 405/14* (2013.01); *C07D 471/04* (2013.01); *C07D 495/04* (2013.01); *C07D 498/04* (2013.01); *C07D 513/04* (2013.01)

(58) Field of Classification Search
None
See application file for complete search history.

(56) References Cited

U.S. PATENT DOCUMENTS 5,817,677 A    10/1998  Linz et al.
9,101,141 B2    8/2015  Kohn et al.
(Continued)

FOREIGN PATENT DOCUMENTS

WO    WO1999/002155    1/1999
WO    WO2005/092864    10/2005
(Continued)

OTHER PUBLICATIONS

Delest, B. et al., Tetrahedron (2004), vol. 60, pp. 6079-6083.*
Al-Hajj et al., "Self-renewal and solid tumor stem cells", Oncogene, 23, pp. 7274-7282, 2004.
Atkinson et al., "N-Benzylimidazole carboxamides as potent, orally active stearoylCoA desaturase-1 inhibitors", Bioorganic & Medicinal Chemistry Letters, 21, pp. 1621-1625, 2011.
Boman et al., "Cancer Stem Cells: A Step Towards the Cure", Journal of Clinical Oncology, vol. 26, No. 17, pp. 2795-2799, Jun. 10, 2008.
(Continued)

*Primary Examiner* — Heidi Reese
(74) *Attorney, Agent, or Firm* — Fish & Richardson P.C.

(57) ABSTRACT

The present invention provides a bicyclic heterocyclic amide derivative of formula (1) wherein ring $Q^1$ is optionally-substituted $C_{6-10}$ aryl group, etc.; $R^1$ and $R^2$ are independently hydrogen atom, etc.; $W^1$ is optionally-substituted $C_{1-4}$ alkylene group; $W^2$ is —$NR^{3a}C(O)$—, etc. wherein $R^{3a}$ is hydrogen atom or $C_{1-6}$ alkyl group; $Cy^1$ is the following group of formula (11), etc.; ring $Q^2$ is optionally-substituted benzene ring, etc.; n and m are independently 0, 1 or 2, provided that n and m are not simultaneously 0; X is $NR^5$, etc.; $R^5$ is hydrogen atom, etc.; p is 1, 2, 3, 4 or 5; $R^4$ is, independently when two or more exist, hydrogen atom, etc.; and a pharmacologically acceptable salt thereof, which have a potent inhibitory effect on the sphere-forming ability of cancer cells and are useful as an orally-available anti-tumor agent.

(1)

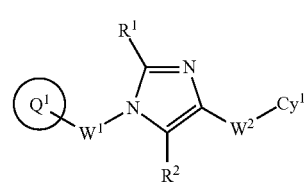

(11)

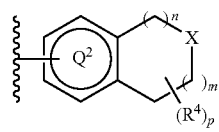

36 Claims, No Drawings

(51) Int. Cl.
| | |
|---|---|
| A61K 31/4709 | (2006.01) |
| C07D 233/88 | (2006.01) |
| C07D 401/12 | (2006.01) |
| C07D 405/12 | (2006.01) |
| C07D 471/04 | (2006.01) |
| C07D 495/04 | (2006.01) |
| C07D 498/04 | (2006.01) |
| C07D 513/04 | (2006.01) |
| A61P 35/02 | (2006.01) |

(56) References Cited

U.S. PATENT DOCUMENTS

| 9,828,362 B2 | 11/2017 | Ban et al. |
|---|---|---|
| 2016/0376263 A1 | 12/2016 | Patron et al. |

FOREIGN PATENT DOCUMENTS

| WO | WO2006/001750 | 1/2006 |
|---|---|---|
| WO | WO2006/087355 | 8/2006 |
| WO | WO2006/114313 | 11/2006 |
| WO | WO2007/034326 | 3/2007 |
| WO | WO2007/073299 | 6/2007 |
| WO | WO2007/138072 | 12/2007 |
| WO | WO2008/073461 | 6/2008 |
| WO | WO2008/138842 | 11/2008 |
| WO | WO2008/138843 | 11/2008 |
| WO | WO2009/060054 | 5/2009 |
| WO | WO2011/106114 | 9/2011 |
| WO | WO2014/125444 | 8/2014 |
| WO | WO2015/151490 | 10/2015 |

OTHER PUBLICATIONS

Delest et al., "Synthesis of 1-benzyl-8,9-dihydroimidazo[4,5-c]pyrrolo[3,2-g]-quinolin-4(5H)-one via palladium-catalyzed intromolecular acylation", Tetrabedron, 60, pp. 6079-6083, 2004.

Deng et al., "Discovery of liver-targeted inhibitors of stearoyl-CoA desaturase (SCD1)", Bioorganic & Medicinal Chemistry Letters, 23, pp. 791-796, 2013.

Haberhauer et al., "Synthesis of Structural Investigation of C4- and C2-Symmetric Molecular Scaffolds Based on Imidazole Peptides", Eur. J. Org. Chem., pp. 1779-1792, 2007.

Helal et al., "Potent and cellularly active 4-aminoimidazole inhibitors of cyclin-dependent kinase 5/p25 for the treatment of Alzheimer's disease", Bioorganic & Medicinal Chemistry Letters, 19, pp. 5703-5707, 2009.

International Search Report and Written Opinion in International Application No. PCT/JP2016/068424, dated Aug. 8, 2016, 8 pages.

Lobo et al., "The Biology of Cancer Stem Cells", Annu. Rev. Cell Dev. Biol., 23:675-99, 2007.

Ponti et al., "Isolation and In Vitro propagation of Tumorigenic Breast Cancer Cells with Stem/Progenitor cell properties", Cancer Res., 65, pp. 5506-5511, 2005.

Su et al., "A Bulky Biaryl Phosphine Ligand Allows for Palladium-Catalyzed Amidation of Five-Membered Heterocycles as Electrophiles", Angew. Chem. Int. Ed., 51, pp. 4710-4713, 2012.

Yamaguchi et al., "Inhibitors of Stearoyl-CoA Desaturase 1 as an Anti-obesity Drug" Monthly Fine Chemicals, vol. 38, No. 8, pp. 12-24, Aug. 2009.

Yamaguchi et al., "Research and Synthesis of stearoyl-CoA desaturase 1 inhibitors", The 27th medicinal chemistry symposium, Nov. 26-28, 2008, Mielparque Osaka.

Yamaguchi et al., "Research and Synthesis of stearoyl-CoA desaturase 1 inhibitors", The Pharm. Soc. Of Japan, Division of Medicinal Chemistry, pp. 166-167, Nov. 10, 2008.

Zhang et al., "Synergistic Effect of the y-Secretase Inhibitor PF-03084014 and Docetaxel in Breast Cancer Models", Stem Cells Translational Medicine, 2, pp. 233-242, 2013.

STN Registry [online] RN: 1351788-43-6 (ED: Dec. 23, 2011), RN: 1351771-27-1.

STN Registry [online] RN: 1251699-10-1 (ED: Nov. 3, 2010), RN: 1251594-36-1.

Extended European Search Report in Application No. 16814362.6, dated Dec. 4, 2018, 9 pages.

* cited by examiner

BICYCLIC HETEROCYCLIC AMIDE DERIVATIVE

CROSS REFERENCE TO RELATED APPLICATIONS

This application is a U.S. National Phase under 35 U.S.C. § 371 of International Application No. PCT/JP2016/068424, filed Jun. 21, 2016, which published as WO 2016/208592, and which claims priority to Japanese Application No. 2015-125175, filed Jun. 22, 2015. All of the above are hereby incorporated by reference in their entireties.

TECHNICAL FIELD

The present invention relates to a pharmaceutically-useful bicyclic heterocyclic amide derivative including a pharmaceutically acceptable salt thereof, and an anti-tumor agent comprising it as an active ingredient.

BACKGROUND ART

Conventional cancer treatments are sometimes not expected to bring in meaningful survival effects even if they can induce the regression of tumors, because of the persistent proliferation of malignant tumors, the metastasis or recurrence of cancer, and the resistance to an anti-tumor agent. These days, it has been suggested that cancer stem cell (hereinafter referred to as "CSC", as necessary) is one of the reasons of the failure, which is closely involved in the factors such as the persistent proliferation of malignant tumor. CSCs have been identified in almost all types of major cancers in human such as breast cancer, colon cancer, lung cancer, and hematological malignancy (Non-Patent Document 1). Also, CSCs can be greatly different in the biological feature from standard cancer cells which differentiate from CSCs, and thus the development of an anti-tumor agent whose target is CSCs is expected to lead to a new strategy for cancer treatments (Non-Patent Document 2).

One of the features in CSCs is the self-renewal ability (Non-Patent Document 3). Reliable methods established for measuring the self-renewal ability of cells include, for example, a method for measuring the sphere-forming ability of cancer cells in non-adherent condition in the absence of serum (Non-Patent Document 4).

Non-Patent Document 5 discloses that PF-03084014 having an N-imidazolylamide skeleton can inhibit CSCs to exhibit an anti-cancer effect. However, Non-Patent Document 5 does not disclose the compound of formula (1) of the present invention.

PRIOR ART DOCUMENTS

Non-Patent Documents

Non-Patent Document 1: Boman et al., Journal of Clinical Oncology 26(17): 2795-2799. 2008
Non-Patent Document 2: Lobo et al., Annu Rev Cell Dev Biol 23: 675-99. 2007
Non-Patent Document 3: Al-Hajj et al., Oncogene 23(43): 7274-82. 2004
Non-Patent Document 4: Ponti et al., Cancer Res 65(13): 5506-11. 2005
Non-Patent Document 5: Zhang et al., Stem Cells Translational Medicine 2: 233-242. 2013

SUMMARY OF INVENTION

Problem to be Solved by the Invention

An object of the present invention is to provide a novel anti-tumor agent whose target is CSCs which are thought to be closely involved in the persistent proliferation of malignant tumor, the metastasis or recurrence of cancer, and the resistance to an anti-tumor agent.

Means for Solving the Problems

The present inventors have extensively studied to reach the above object, and then have found that a compound of the following formula (1) or a pharmaceutically acceptable salt thereof (hereinafter referred to as "the present compound", as necessary) has a potent inhibitory effect on the sphere-forming ability of cancer cells and is highly useful as a novel anti-tumor agent. Based upon the new findings, the present invention has been completed.

The present invention provides inventions described below.

[1] A compound of formula (1):

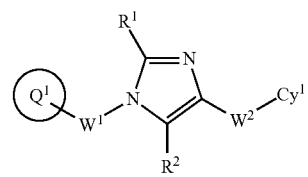

or a pharmaceutically acceptable salt thereof, wherein ring $Q^1$ is optionally-substituted $C_{6-10}$ aryl group, optionally-substituted $C_{3-10}$ cycloalkyl group, or optionally-substituted 5- to 10-membered heteroaryl group;

$R^1$ and $R^2$ are independently hydrogen atom, halogen atom, or $C_{1-6}$ alkyl group which may be optionally substituted with the same or different 1 to 3 halogen atoms;

$W^1$ is optionally-substituted $C_{1-4}$ alkylene group;

$W^2$-$Cy^1$ is —$NR^{3a}C(O)$-$Cy^1$, —$NR^{3a}C(O)O$-$Cy^1$, —$NR^{3a}C(O)OCH_2$-$Cy^1$, —$NR^{3a}C(O)NR^{3b}$-$Cy^1$, —$NR^{3a}C(O)NR^{3b}CH_2$-$Cy^1$, —$NR^{3a}C(O)CH_2O$-$Cy^1$, —$NR^{3a}C(O)CH_2$-$Cy^1$, —$NR^{3a}C(O)CH_2CH_2$-$Cy^1$, —$C(O)NR^{3a}$-$Cy^1$, —$C(O)NR^{3a}CH_2$—$C(O)NR^{3a}CH_2CH_2$-$Cy^1$, or —$NR^{3a}C(O)$—$CR^{3c}$=$CR^3$-$Cy^1$ wherein $R^{3a}$ and $R^{3b}$ are independently hydrogen atom or $C_{1-6}$ alkyl group; and $R^{3c}$ and $R^{3d}$ are independently hydrogen atom, fluorine atom, or $C_{1-6}$ alkyl group; and $Cy^1$ is a group of the following formula (11), (12), (13), (14), (15), or (16):

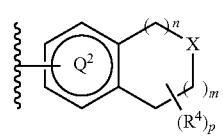

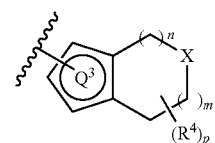

3
-continued

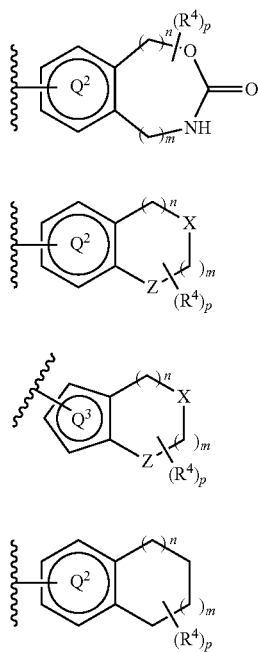

wherein ring $Q^2$ is optionally-substituted benzene ring, optionally-substituted pyridine ring, optionally-substituted pyrimidine ring, optionally-substituted pyridazine ring, or optionally-substituted pyrazine ring;

ring $Q^3$ is optionally-substituted 5-membered heteroaryl ring;

n and m are independently 0, 1 or 2, provided that n and m are not simultaneously 0;

X and Z are independently $NR^5$, —$NR^{3e}C(O)$—, —$C(O)NR^{3e}$—, or O wherein $R^5$ is hydrogen atom, $C_{1-6}$ alkyl group which may be optionally substituted with the same or different 1 to 3 halogen atoms, or $C_{1-6}$ alkylcarbonyl; and $R^{3e}$ is hydrogen atom or $C_{1-6}$ alkyl group;

p is 1, 2, 3, 4 or 5; and $R^4$ is, independently when two or more exist, hydrogen atom, halogen atom, hydroxy, oxo, $C_{1-6}$ alkyl group which may be optionally substituted with the same or different 1 to 3 halogen atoms, or $C_{1-6}$ alkoxy group which may be optionally substituted with the same or different 1 to 3 halogen atoms; or when two $R^4$ are attached to the same carbon atom or the adjacent carbon atoms on the ring, they may be combined with the carbon atom(s) to form (1) 5- to 8-membered saturated or partially-unsaturated carbocyclic ring which may be optionally substituted with the same or different 1 to 4 groups selected from the group consisting of halogen atom, hydroxy, $C_{1-6}$ alkyl, and $C_{1-6}$ alkoxy, or (2) 5- to 8-membered saturated or partially-unsaturated heterocyclic ring which may be optionally substituted with the same or different 1 to 4 groups selected from the group consisting of halogen atom, hydroxy, $C_{1-6}$ alkyl, and $C_{1-6}$ alkoxy.

4

[2] A compound of formula (1):

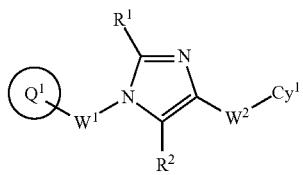

or a pharmaceutically acceptable salt thereof, wherein ring $Q^1$ is optionally-substituted $C_{6-10}$ aryl group, optionally-substituted $C_{3-10}$ cycloalkyl group, or optionally-substituted 5- to 10-membered heteroaryl group;

$R^1$ and $R^2$ are independently hydrogen atom, halogen atom, or $C_{1-6}$ alkyl group which may be optionally substituted with the same or different 1 to 3 halogen atoms;

$W^1$ is optionally-substituted $C_{1-4}$ alkylene group;

$W^2$-Cy1 is —$NR^{3a}C(O)$-$Cy^1$, —$NR^{3a}C(O)O$-$Cy^1$, —$NR^{3a}C(O)OCH_2$-$Cy^1$, —$NR^{3a}C(O)NR^{3b}$-$Cy^1$, —$NR^{3a}C(O)NR^{3b}CH_2$-$Cy^1$, —$NR^{3a}C(O)CH_2O$-$Cy^1$, —$NR^{3a}C(O)CH_2$-$Cy^1$, —$NR^{3a}C(O)CH_2CH_2$-$Cy^1$, —$C(O)NR^{3a}$-$Cy^1$, —$C(O)NR^{3a}CH_2$-$Cy^1$, or —$C(O)NR^{3a}CH_2CH_2$-Cy wherein $R^{3a}$ and $R^{3b}$ are independently hydrogen atom or $C_{1-6}$ alkyl group; and $Cy^1$ is a group of the following formula (11), (12), or (13):

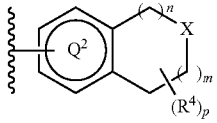

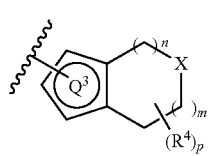

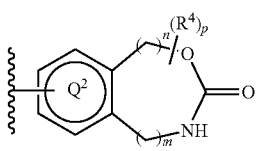

wherein ring $Q^2$ is optionally-substituted benzene ring, optionally-substituted pyridine ring, optionally-substituted pyrimidine ring, optionally-substituted pyridazine ring, or optionally-substituted pyrazine ring;

ring $Q^3$ is optionally-substituted 5-membered heteroaryl ring;

n and m are independently 0, 1 or 2, provided that n and m are not simultaneously 0;

X is $NR^5$ or O wherein $R^5$ is hydrogen atom or $C_{1-6}$ alkyl group which may be optionally substituted with the same or different 1 to 3 halogen atoms;

p is 1, 2, 3, 4 or 5; and $R^4$ is, independently when two or more exist, hydrogen atom, halogen atom, or $C_{1-6}$ alkyl group which may be optionally substituted with the same or different 1 to 3 halogen atoms.

[3] The compound according to [1] or [2] or a pharmaceutically acceptable salt thereof, wherein ring $Q^1$ is (1) $C_{6-10}$ aryl group which may be optionally substituted with the same or different 1 to 5 groups selected from the group consisting of:
  (a) halogen atom,
  (b) $C_{1-6}$ alkyl which may be optionally substituted with the same or different 1 to 3 groups selected from the group consisting of halogen atom, hydroxy, and $C_{1-6}$ alkoxy,
  (c) $C_{1-6}$ alkoxy which may be optionally substituted with the same or different 1 to 3 groups selected from the group consisting of halogen atom, hydroxy, and $C_{1-6}$ alkoxy,
  (d) cyano,
  (e) $C_{6-10}$ aryl which may be optionally substituted with the same or different 1 to 4 groups selected from the group consisting of halogen atom, $C_{1-6}$ alkyl, and $C_{1-6}$ alkoxy,
  (f) 5- or 6-membered heteroaryl which may be optionally substituted with the same or different 1 to 4 groups selected from the group consisting of halogen atom, $C_{1-6}$ alkyl, and $C_{1-6}$ alkoxy,
  (g) $C_{6-10}$ aryloxy which may be optionally substituted with the same or different 1 to 4 groups selected from the group consisting of halogen atom, $C_{1-6}$ alkyl, and $C_{1-6}$ alkoxy,
  (h) hydroxy,
  (i) amino which may be optionally substituted with the same or different 1 to 2 $C_{1-6}$ alkyl groups,
  (j) aminocarbonyl wherein the amino moiety thereof may be optionally substituted with the same or different 1 to 2 $C_{1-6}$ alkyl groups,
  (k) $C_{1-6}$ alkoxy-carbonyl wherein the alkoxy moiety thereof may be optionally substituted with the same or different 1 to 3 groups selected from the group consisting of halogen atom, hydroxy, and $C_{1-6}$ alkoxy,
  (l) $C_{1-6}$ alkyl-carbonyl wherein the alkyl moiety thereof may be optionally substituted with the same or different 1 to 3 groups selected from the group consisting of halogen atom, hydroxy, and $C_{1-6}$ alkoxy,
  (m) $C_{1-6}$ alkylsulfonyl wherein the alkyl moiety thereof may be optionally substituted with the same or different 1 to 3 groups selected from the group consisting of halogen atom, hydroxy, and $C_{1-6}$ alkoxy,
  (n) $C_{1-6}$ alkyl-carbonylamino wherein the alkyl moiety thereof may be optionally substituted with the same or different 1 to 3 groups selected from the group consisting of halogen atom, hydroxy, and $C_{1-6}$ alkoxy,
  (o) $C_{1-6}$ alkylsulfonylamino wherein the alkyl moiety thereof may be optionally substituted with the same or different 1 to 3 groups selected from the group consisting of halogen atom, hydroxy, and $C_{1-6}$ alkoxy,
  (p) $C_{1-6}$ alkoxy-carbonylamino wherein the alkoxy moiety thereof may be optionally substituted with the same or different 1 to 3 groups selected from the group consisting of halogen atom, hydroxy, and $C_{1-6}$ alkoxy,
  (q) alkyl-carbonyloxy wherein the alkyl moiety thereof may be optionally substituted with the same or different 1 to 3 groups selected from the group consisting of halogen atom, hydroxy, and $C_{1-6}$ alkoxy,
  (r) aminosulfonyl wherein the amino moiety thereof may be optionally substituted with the same or different 1 to 2 $C_{1-6}$ alkyl groups, and
  (s) $C_{3-10}$ cycloalkyl which may be optionally substituted with the same or different 1 to 4 groups selected from the group consisting of halogen atom, hydroxy, and $C_{1-6}$ alkoxy,
(2) $C_{3-10}$ cycloalkyl group which may be optionally substituted with the same or different 1 to 5 groups selected from the group consisting of (a) to (s) defined in the above (1), or
(3) 5- to 10-membered heteroaryl group which may be optionally substituted with the same or different 1 to 5 groups selected from the group consisting of (a) to (s) defined in the above (1);
$W^1$ is $C_{1-4}$ alkylene group which may be optionally substituted with the same or different 1 to 4 groups selected from the group consisting of halogen atom, hydroxy, and $C_{1-6}$ alkoxy;
ring $Q^2$ is benzene ring, pyridine ring, pyrimidine ring, pyridazine ring, or pyrazine ring wherein the benzene ring, pyridine ring, pyrimidine ring, pyridazine ring, and pyrazine ring may be optionally substituted with the same or different 1 to 3 groups selected from the group consisting of
(1) halogen atom,
(2) $C_{1-6}$ alkyl which may be optionally substituted with the same or different 1 to 4 groups selected from the group consisting of the same or different 1 to 3 halogen atoms, hydroxy and $C_{1-6}$ alkoxy,
(3) $C_{1-6}$ alkoxy which may be optionally substituted with the same or different 1 to 3 halogen atoms,
(4) hydroxy, and
(5) cyano;
ring $Q^3$ is 5-membered heteroaryl ring which may be optionally substituted with halogen atom or $C_{1-6}$ alkyl which may be optionally substituted with the same or different 1 to 4 groups selected from the group consisting of the same or different 1 to 3 halogen atoms, hydroxy and $C_{1-6}$ alkoxy.

[4] The compound according to any one of [1] to [3] or a pharmaceutically acceptable salt thereof, wherein ring $Q^1$ is
(1) phenyl group which may be optionally substituted with the same or different 1 to 5 groups selected from the group consisting of:
  (a) halogen atom,
  (b) $C_{1-6}$ alkyl which may be optionally substituted with the same or different 1 to 3 groups selected from the group consisting of halogen atom, hydroxy and $C_{1-6}$ alkoxy,
  (c) $C_{1-6}$ alkoxy which may be optionally substituted with the same or different 1 to 3 groups selected from the group consisting of halogen atom, hydroxy and $C_{1-6}$ alkoxy,
  (d) cyano,
  (e) phenyl which may be optionally substituted with the same or different 1 to 4 groups selected from the group consisting of halogen atom, $C_{1-6}$ alkyl and $C_{1-6}$ alkoxy,
  (f) 5- or 6-membered heteroaryl which may be optionally substituted with the same or different 1 to 4 groups selected from the group consisting of halogen atom, $C_{1-6}$ alkyl and $C_{1-6}$ alkoxy, and
  (g) phenoxy which may be optionally substituted with the same or different 1 to 4 groups selected from the group consisting of halogen atom, $C_{1-6}$ alkyl and $C_{1-6}$ alkoxy,
(2) $C_{3-7}$ cycloalkyl group which may be optionally substituted with 1 to 4 groups selected from the group consisting of (a) to (g) defined in the above (1), or
(3) pyridyl group which may be optionally substituted with 1 to 4 groups selected from the group consisting of (a) to (g) defined in the above (1).

[5] The compound according to any one of [1] to [4] or a pharmaceutically acceptable salt thereof, wherein ring $Q^1$ is phenyl group which may be optionally substituted with the same or different 1 to 5 groups selected from the group consisting of:
  (a) halogen atom,
  (b) $C_{1-6}$ alkyl which may be optionally substituted with the same or different 1 to 3 halogen atoms, and
  (c) $C_{1-6}$ alkoxy which may be optionally substituted with the same or different 1 to 3 halogen atoms.

[6] The compound according to any one of [1] to [5] or a pharmaceutically acceptable salt thereof, wherein $W^1$ is methylene group which may be optionally substituted with the same or different 1 to 2 halogen atoms or ethylene group which may be optionally substituted with the same or different 1 to 4 halogen atoms.

[7] The compound according to any one of [1] to [6] or a pharmaceutically acceptable salt thereof, wherein $W^2$-$Cy^1$ is —$NR^{3a}C(O)$-$Cy^1$ or —$C(O)NR^{3a}$-$Cy^1$ wherein $R^{3a}$ is hydrogen atom or $C_{1-6}$ alkyl group.

[8] The compound according to any one of [1] to [7] or a pharmaceutically acceptable salt thereof, wherein $W^2$-$Cy^1$ is —$NR^{3a}C(O)$-$Cy^1$ wherein $R^{3a}$ is hydrogen atom or $C_{1-6}$ alkyl group.

[9] The compound according to [1] represented by formula (1a):

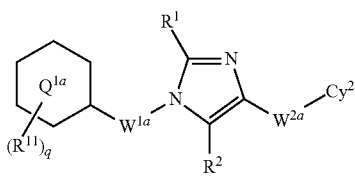

(1a)

or a pharmaceutically acceptable salt thereof, wherein ring $Q^{1a}$ is phenyl group, pyridyl group, or cyclohexyl group;

q is 1, 2, 3, 4 or 5;

$R^{11}$ is, independently when two or more exist, (1) hydrogen atom, (2) halogen atom, (3) $C_{1-6}$ alkyl group which may be optionally substituted with the same or different 1 to 3 halogen atoms, or (4) $C_{1-6}$ alkoxy group which may be optionally substituted with the same or different 1 to 3 halogen atoms;

$R^1$ and $R^2$ are independently hydrogen atom, halogen atom, or $C_{1-6}$ alkyl group which may be optionally substituted with the same or different 1 to 3 halogen atoms;

$W^{1a}$ is methylene group which may be optionally substituted with the same or different 1 to 2 halogen atoms or ethylene group which may be optionally substituted with the same or different 1 to 4 halogen atoms;

$W^{2a}$-$Cy^2$ is —$NR^{3a}C(O)$-$Cy^2$ or —$C(O)NR^{3a}$-$Cy^2$ wherein $R^{3a}$ is hydrogen atom or $C_{1-6}$ alkyl group; and $Cy^2$ is a group of the following formula (21), (22), or (23):

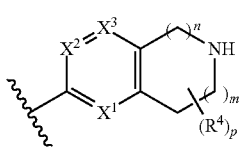

(21)

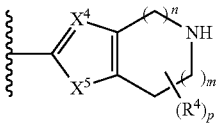

(22)

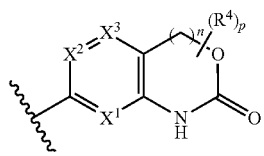

(23)

wherein $X^1$ is N or $CR^{12}$;
$X^2$ is N or $CR^{13}$;
$X^3$ is N or $CR^{14}$;
$X^4$ is N or $CR^{15}$;
$X^5$ is S, O or NH;
provided that $X^1$, $X^2$ and $X^3$ are not simultaneously N;
$R^{12}$, $R^{13}$, $R^{14}$ and $R^{15}$ are independently (1) hydrogen atom, (2) halogen atom, (3) $C_{1-6}$ alkyl group which may be optionally substituted with the same or different 1 to 3 halogen atoms, or (4) $C_{1-6}$ alkoxy group which may be optionally substituted with the same or different 1 to 3 halogen atoms;

n and m are independently 0, 1 or 2, provided that n and m are not simultaneously 0;

p is 1, 2, 3, 4 or 5; and $R^4$ is, independently when two or more exist, hydrogen atom, halogen atom, or $C_{1-6}$ alkyl group which may be optionally substituted with the same or different 1 to 3 halogen atoms.

[10] The compound according to [9] or a pharmaceutically acceptable salt thereof, wherein ring $Q^{1a}$ is phenyl group.

[11] The compound according to [9] or [10] or a pharmaceutically acceptable salt thereof, wherein $W^{2a}$-$Cy^2$ is —$NHC(O)$-$Cy^2$.

[12] The compound according to [9] or [10] or a pharmaceutically acceptable salt thereof, wherein $W^{2a}$-$Cy^2$ is —$C(O)NH$-$Cy^2$.

[13] The compound according to any one of [9] to [12] or a pharmaceutically acceptable salt thereof, wherein $Cy^2$ is a group of formula (21) or (23).

[14] The compound according to any one of [9] to [12] or a pharmaceutically acceptable salt thereof, wherein $Cy^2$ is a group of formula (22); $X^4$ is N or CH; and $X^5$ is S.

[15] The compound according to any one of [1] to [14] or a pharmaceutically acceptable salt thereof, wherein $R^1$ and $R^2$ are hydrogen atom.

[16] The compound according to [1] represented by formula (1b):

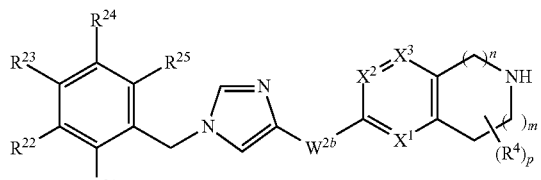

(1b)

or a pharmaceutically acceptable salt thereof, wherein is N or $CR^{12}$;
$X^2$ is N or $CR^{13}$;
$X^3$ is N or $CR^{14}$;
provided that $X^1$, $X^2$ and $X^3$ are not simultaneously N;
$W^{2b}$ is —NHC(O)— or —C(O)NH—;

$R^{12}$, $R^{13}$, $R^{14}$, $R^{21}$, $R^{22}$, $R^{23}$, $R^{24}$, and $R^{25}$ are independently
(1) hydrogen atom,
(2) halogen atom,
(3) $C_{1-6}$ alkyl group which may be optionally substituted with the same or different 1 to 3 halogen atoms, or
(4) $C_{1-6}$ alkoxy group which may be optionally substituted with the same or different 1 to 3 halogen atoms;
n and m are independently 0, 1 or 2, provided that n and m are not simultaneously 0;
p is 1, 2, 3, 4 or 5; and
$R^4$ is, independently when two or more exist, hydrogen atom, halogen atom, or $C_{1-6}$ alkyl group which may be optionally substituted with the same or different 1 to 3 halogen atoms.

[17] The compound according to [16] or a pharmaceutically acceptable salt thereof, wherein $R^{22}$ is halogen atom or $C_{1-6}$ alkyl group which may be optionally substituted with the same or different 1 to 3 halogen atoms.

[18] The compound according to [16] or a pharmaceutically acceptable salt thereof, wherein $R^{22}$ is halogen atom.

[19] The compound according to any one of [16] to [18] or a pharmaceutically acceptable salt thereof, wherein $R^{21}$, $R^{23}$, $R^{24}$ and $R^{25}$ are independently
(1) hydrogen atom,
(2) halogen atom, or
(3) $C_{1-6}$ alkyl group which may be optionally substituted with the same or different 1 to 3 halogen atoms.

[20] The compound according to any one of [16] to [19] or a pharmaceutically acceptable salt thereof wherein $W^{2b}$ is —NRC(O)—.

[21] The compound according to any one of [16] to [19] or a pharmaceutically acceptable salt thereof, wherein $W^{2b}$ is —C(O)NH—.

[22] The compound according to any one of [9] to [21] or a pharmaceutically acceptable salt thereof, wherein only one of $X^1$, $X^2$ and $X^3$ is N.

[23] The compound according to any one of [1] to [22] or a pharmaceutically acceptable salt thereof, wherein $R^4$ is hydrogen atom.

[24] The compound according to any one of [1] to [23] or a pharmaceutically acceptable salt thereof, wherein n is 1 and m is 1; or n is 2 and m is 0.

[25] The compound according to any one of [1] to [24] or a pharmaceutically acceptable salt thereof, wherein n is 1 and m is 1.

[26] The compound according to [1] selected from the following compounds or a pharmaceutically acceptable salt thereof:
N-(7-fluoro-1,2,3,4-tetrahydroisoquinolin-6-yl)-1-(3,4,5-trifluorobenzyl)-1H-imidazole-4-carboxamide (Example 1),
N-(5,6,7,8-tetrahydro-2,7-naphthyridin-3-yl)-1-(3,4,5-trifluorobenzyl)-1H-imidazole-4-carboxamide (Example 3),
N-(1,2,3,4-tetrahydroisoquinolin-6-yl)-1-(3,4,5-trifluorobenzyl)-1H-imidazole-4-carboxamide (Example 4),
8-fluoro-N-[1-(3,4,5-trifluorobenzyl)-1H-imidazol-4-yl]-1,2,3,4-tetrahydroisoquinoline-6-carboxamide (Example 5),
N-[1-(3,4,5-trifluorobenzyl)-1H-imidazol-4-yl]-1,2,3,4-tetrahydroisoquinoline-6-carboxamide (Example 6),
N-[1-(3,4,5-trifluorobenzyl)-1H-imidazol-4-yl]-5,6,7,8-tetrahydro-2,7-naphthyridine-3-carboxamide (Example 8),
N-{1-[3-(trifluoromethyl)benzyl]-1H-imidazol-4-yl}-5,6,7,8-tetrahydro-2,7-naphthyridine-3-carboxamide (Example 9),
N-{1-[3-(trifluoromethyl)benzyl]-1H-imidazol-4-yl}-5,6,7,8-tetrahydro-1,6-naphthyridine-2-carboxamide (Example 10),
N-[1-(3,4,5-trifluorobenzyl)-1H-imidazol-4-yl]-5,6,7,8-tetrahydro-1,6-naphthyridine-2-carboxamide (Example 11),
N-[1-(3,4,5-trifluorobenzyl)-1H-imidazol-4-yl]-5,6,7,8-tetrahydro-1,7-naphthyridine-3-carboxamide (Example 12),
N-{1-[3-(trifluoromethyl)benzyl]-1H-imidazol-4-yl}-5,6,7,8-tetrahydro-1,7-naphthyridine-3-carboxamide (Example 13),
N-{1-[3-(trifluoromethyl)benzyl]-1H-imidazol-4-yl}-1,2,3,4-tetrahydroisoquinoline-6-carboxamide (Example 19),
1-(3,4-difluorobenzyl)-N-(5,6,7,8-tetrahydro-2,7-naphthyridin-3-yl)-1H-imidazole-4-carboxamide (Example 35),
N-[1-(3,5-difluorobenzyl)-1H-imidazol-4-yl]-5,6,7,8-tetrahydro-1,7-naphthyridine-3-carboxamide (Example 47),
N-[1-(3,4-difluorobenzyl)-1H-imidazol-4-yl]-5,6,7,8-tetrahydro-1,7-naphthyridine-3-carboxamide (Example 48),
N-{1-[3-(trifluoromethoxy)benzyl]-1H-imidazol-4-yl}-5,6,7,8-tetrahydro-1,7-naphthyridine-3-carboxamide (Example 49),
N-[1-(3-phenoxybenzyl)-1H-imidazol-4-yl]-5,6,7,8-tetrahydro-1,7-naphthyridine-3-carboxamide (Example 50),
N-[1-(4-chloro-3-fluorobenzyl)-1H-imidazol-4-yl]-5,6,7,8-tetrahydro-1,7-naphthyridine-3-carboxamide (Example 51),
N-[1-(3-chloro-5-fluorobenzyl)-1H-imidazol-4-yl]-5,6,7,8-tetrahydro-1,7-naphthyridine-3-carboxamide (Example 52),
N-{1-[4-fluoro-3-(trifluoromethyl)benzyl]-1H-imidazol-4-yl}-5,6,7,8-tetrahydro-1,7-naphthyridine-3-carboxamide (Example 53),
N-{1-[4-chloro-3-(trifluoromethyl)benzyl]-1H-imidazol-4-yl}-5,6,7,8-tetrahydro-1,7-naphthyridine-3-carboxamide (Example 54),
N-{1-[4-(trifluoromethyl)benzyl]-1H-imidazol-4-yl}-5,6,7,8-tetrahydro-1,7-naphthyridine-3-carboxamide (Example 64),
N-[1-(4-chlorobenzyl)-1H-imidazol-4-yl]-5,6,7,8-tetrahydro-1,7-naphthyridine-3-carboxamide (Example 65),
N-{1-[3-chloro-5-(trifluoromethoxy)benzyl]-1H-imidazol-4-yl}-5,6,7,8-tetrahydro-1,7-naphthyridine-3-carboxamide (Example 70),
N-[1-(3-phenoxybenzyl)-1H-imidazol-4-yl]-1,2,3,4-tetrahydroisoquinoline-6-carboxamide (Example 89),
N-[1-(4-chloro-3-fluorobenzyl)-1H-imidazol-4-yl]-1,2,3,4-tetrahydroisoquinoline-6-carboxamide (Example 90),
N-[1-(3-chloro-5-fluorobenzyl)-1H-imidazol-4-yl]-1,2,3,4-tetrahydroisoquinoline-6-carboxamide (Example 91),
N-{1-[4-fluoro-3-(trifluoromethyl)benzyl]-1H-imidazol-4-yl}-1,2,3,4-tetrahydroisoquinoline-6-carboxamide (Example 92),
N-{1-[4-chloro-3-(trifluoromethyl)benzyl]-1H-imidazol-4-yl}-1,2,3,4-tetrahydroisoquinoline-6-carboxamide (Example 93),
N-[1-(3-chloro-4-fluorobenzyl)-1H-imidazol-4-yl]-1,2,3,4-tetrahydroisoquinoline-6-carboxamide (Example 95),
N-{1-[4-methyl-3-(trifluoromethyl)benzyl]-1H-imidazol-4-yl}-1,2,3,4-tetrahydroisoquinoline-6-carboxamide (Example 97),
N-{1-[3-fluoro-5-(trifluoromethyl)benzyl]-1H-imidazol-4-yl}-1,2,3,4-tetrahydroisoquinoline-6-carboxamide (Example 99),
N-{1-[3-chloro-5-(trifluoromethoxy)benzyl]-1H-imidazol-4-yl}-1,2,3,4-tetrahydroisoquinoline-6-carboxamide (Example 100), N-[1-(3,5-dichlorobenzyl)-1H-imidazol-4-yl]-1,2,3,4-tetrahydroisoquinoline-6-carboxamide (Example 101), and
N-[1-(3,4-dichlorobenzyl)-1H-imidazol-4-yl]-1,2,3,4-tetrahydroisoquinoline-6-carboxamide (Example 102).

[27] The compound according to [1] selected from the following compounds or a pharmaceutically acceptable salt thereof:
N-(5,6,7,8-tetrahydro-2,7-naphthyridin-3-yl)-1-(3,4,5-trifluorobenzyl)-1H-imidazole-4-carboxamide (Example 3),
8-fluoro-N-[1-(3,4,5-trifluorobenzyl)-1H-imidazol-4-yl]-1,2,3,4-tetrahydroisoquinoline-6-carboxamide (Example 5),
N-[1-(3,4,5-trifluorobenzyl)-1H-imidazol-4-yl]-1,2,3,4-tetrahydroisoquinoline-6-carboxamide (Example 6),
N-{1-[3-(trifluoromethyl)benzyl]-1H-imidazol-4-yl}-5,6,7,8-tetrahydro-1,6-naphthyridine-2-carboxamide (Example 10),
N-[1-(3,4,5-trifluorobenzyl)-1H-imidazol-4-yl]-5,6,7,8-tetrahydro-1,6-naphthyridine-2-carboxamide (Example 11),
N-[1-(3,4,5-trifluorobenzyl)-1H-imidazol-4-yl]-5,6,7,8-tetrahydro-1,7-naphthyridine-3-carboxamide (Example 12), and
N-{1-[3-(trifluoromethyl)benzyl]-1H-imidazol-4-yl}-5,6,7,8-tetrahydro-1,7-naphthyridine-3-carboxamide (Example 13).

[28] A medicament comprising the compound according to any one of [1] to [27] or a pharmaceutically acceptable salt thereof as an active ingredient.

[29] An anti-tumor agent comprising the compound according to any one of [1] to [27] or a pharmaceutically acceptable salt thereof as an active ingredient.

[30] The anti-tumor agent according to [29], wherein the tumor is acute leukemia, chronic lymphatic leukemia, chronic myelocytic leukemia, polycythemia vera, malignant lymphoma, myeloma, brain tumor, head and neck cancer, esophageal cancer, thyroid cancer, small-cell lung cancer, non-small cell lung cancer, breast cancer, stomach cancer, gallbladder or bile duct cancer, liver cancer, pancreatic cancer, colon cancer, rectal cancer, ovarian cancer, chorioepithelioma, endometrial cancer, cervical cancer, urothelial cancer, renal cell cancer, prostate cancer, testicular tumor, Wilms' tumor, malignant melanoma, neuroblastoma, osteosarcoma, Ewing's sarcoma, or soft tissue sarcoma.

A medicament comprising the compound according to any one of [1] to [27] or a pharmaceutically acceptable salt thereof in combination with another anti-cancer agent selected from the group consisting of an anticancer alkylating agent, an anticancer antimetabolite, an anticancer antibiotic, a plant-based anti-cancer agent, an anticancer platinum coordination compound, an anticancer camptothecin derivative, an anticancer tyrosine kinase inhibitor, a serine-threonine kinase inhibitor, a phospholipid kinase inhibitor, a monoclonal antibody, an interferon, a biological response modifier, a hormone preparation, an immune checkpoint inhibitor, an epigenetics-related molecule inhibitor, a post-translational protein modification inhibitor, and an anticancer agent other than the foregoings or a pharmaceutically acceptable salt thereof.

[32] A method for treating cancer which comprises administering a therapeutically effective amount of the compound according to any one of [1] to [27] or a pharmaceutically acceptable salt thereof to a patient in need thereof.

[33] Use of the compound according to any one of [1] to [27] or a pharmaceutically acceptable salt thereof for the manufacture of an agent for treating cancer.

[34] A pharmaceutical composition for the treatment of cancer comprising the compound according to any one of [1] to [27] or a pharmaceutically acceptable salt thereof.

[35] The compound according to any one of [1] to [27] or a pharmaceutically acceptable salt thereof for the use in treating cancer.

Effects of the Invention

The present compound has a potent inhibitory effect on the sphere-forming ability of cancer cells. In addition, the preferred present compound has high biological availability (bioavailability) after oral administration. Thus, the present compound is useful as an orally-available anti-cancer agent.

DESCRIPTION OF EMBODIMENTS

Hereinafter, the present invention is explained in detail. The number of carbon atoms in the definition of the "substituent" used herein may be expressed as, for example, "$C_{1-6}$". Specifically, the term "$C_{1-6}$ alkyl" is used for the same meaning as alkyl group having 1 to 6 carbon atoms.

Specific examples of "halogen atom" used herein include fluorine atom, chlorine atom, bromine atom, and iodine atom.

The term "$C_{1-6}$ alkyl group" used herein means a straight or branched, saturated hydrocarbon group having 1 to 6 carbon atoms. Preferred examples thereof include "$C_{1-4}$ alkyl group". Specific examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, and 2-ethylbutyl.

The term "$C_{1-4}$ alkylene group" used herein means a straight or branched, divalent saturated hydrocarbon group having 1 to 4 carbon atoms, or a divalent saturated hydrocarbon group containing a cyclic structure having 3 to 4 carbon atoms.

Specific examples of the straight or branched "$C_{1-4}$ alkylene group" include methylene, ethylene, trimethylene, tetramethylene, 1-methylmethylene, 1-ethylmethylene, 1-propylmethylene, 1-methylethylene, 2-methylethylene, and 1-ethylethylene. Preferred examples thereof include methylene and ethylene.

Specific examples of the "$C_{1-4}$ alkylene group" containing a cyclic structure include the following groups:

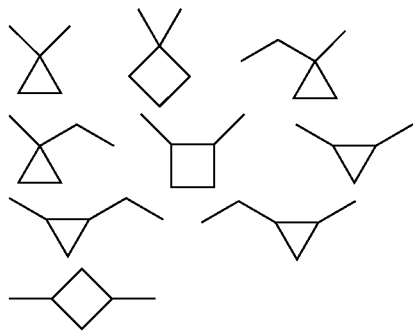

The "$C_{1-6}$ alkyl" moiety of the term "$C_{1-6}$ alkoxy group" used herein is as defined in the above "$C_{1-6}$ alkyl". Preferred examples thereof include "$C_{1-4}$ alkoxy group". Specific examples of the "$C_{1-6}$ alkoxy group" include methoxy, ethoxy, propoxy, isopropoxy, butoxy, isobutoxy, sec-butoxy, and tert-butoxy.

The term "$C_{3-10}$ cycloalkyl group" used herein means a to 10-membered monocyclic or polycyclic, saturated or partially-unsaturated hydrocarbon group. The group is preferably "$C_{3-7}$ cycloalkyl group", and more preferably cyclohexyl group. Specific examples of the "$C_{3-10}$ cycloalkyl group" include cyclopropyl, cyclobutyl, cyclopentyl, cyclohexyl, cycloheptyl, cyclopentenyl, cyclohexenyl, decalinyl, adamantyl, and norbornyl.

The term "$C_{6-10}$ aryl group" used herein means an aromatic hydrocarbon group having 6 to 10 carbon atoms. The group is preferably "$C_6$ aryl group" (phenyl). Specific examples of the "$C_{6-10}$ aryl group" include phenyl, 1-naphthyl, or 2-naphthyl.

Examples of the term "5- to 10-membered heteroaryl group" used herein include a 5- to 10-membered mono- or bi-cyclic aromatic group which contains the same or different one or more (e.g. 1 to 4) heteroatoms selected from the group consisting of nitrogen atom, sulfur atom, and oxygen atom. The bicyclic heteroaryl group also encompasses a fused ring group of a monocyclic heteroaryl group mentioned above with an aromatic group (such as benzene and pyridine) or a non-aromatic ring (such as cyclohexyl and piperidine). Specific examples of the "heteroaryl group" include the groups of the following formulae:

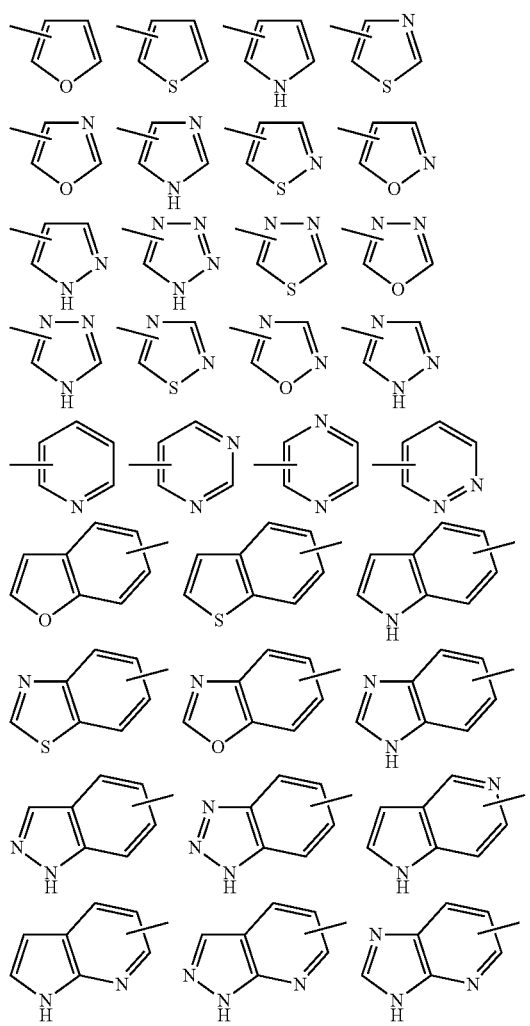

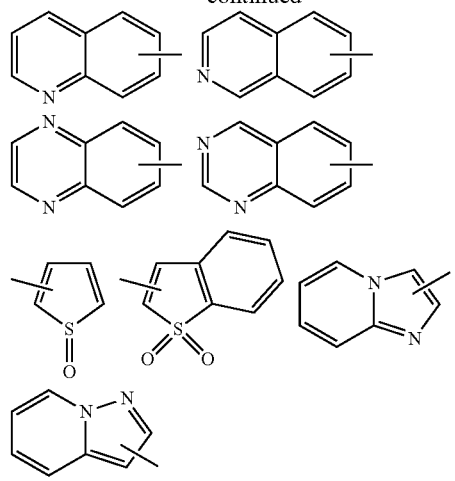

-continued

The bond across a ring in the above formulae means that a "group" is linked at any replaceable position in the ring. For example, when a group is the heteroaryl group of the following formula:

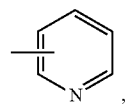

the group means 2-pyridyl group, 3-pyridyl group, or 4-pyridyl group.

Furthermore, when a "heteroaryl group" is a bicyclic group, for example, the group of the following formula:

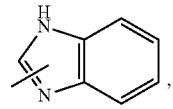

the group may be 1-benzimidazolyl, 2-benzimidazolyl, or 4-, 5-, 6- or 7-benzimidazolyl.

In the groups of formulae (11), (12) and (13) defined in the above [1], the two atoms indicated by arrows, which are shared between ring $Q^2$ or ring $Q^3$ and another ring fused with the ring, are carbon.

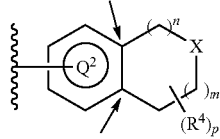

(11)

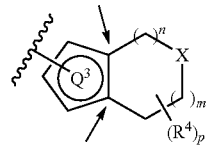

(12)

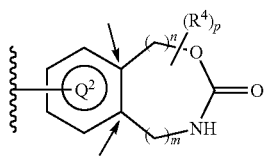

(13)

The term "aminocarbonyl group" used herein means a formyl group wherein hydrogen atom therein is replaced with amino group.

The "$C_{1-6}$ alkyl" moiety of the term "$C_{1-6}$ alkyl-carbonylamino group" used herein is as defined in the above "$C_{1-6}$ alkyl". Preferred examples thereof include "$C_{1-4}$ alkyl-carbonylamino group", more preferably methylcarbonylamino group (acetamido group).

The "$C_{6-10}$ aryl" moiety of the term "$C_{6-10}$ aryloxy group" is as defined in the above "$C_{6-10}$ aryl". Preferred examples thereof include "$C_6$ aryloxy group" (phenoxy group).

The "$C_{1-6}$ alkoxy" moiety of the term "$C_{1-6}$ alkoxycarbonyl group" used herein is as defined in the above "$C_{1-6}$ alkoxy". Preferred examples thereof include "$C_{1-4}$ alkoxycarbonyl group". Specific examples of the "$C_{1-6}$ alkoxycarbonyl group" include methoxycarbonyl, ethoxycarbonyl, and propoxycarbonyl.

The "$C_{1-6}$ alkyl" moiety of the term "$C_{1-6}$ alkyl-carbonyl group" used herein is as defined in the above "$C_{1-6}$ alkyl". Preferred examples thereof include "$C_{1-4}$ alkyl-carbonyl group". Specific examples of the "$C_{1-6}$ alkyl-carbonyl group" include acetyl, ethylcarbonyl, and propylcarbonyl.

The "$C_{1-6}$ alkyl" moiety of the term "$C_{1-6}$ alkylsulfonyl group" used herein is as defined in the above "$C_{1-6}$ alkyl". Preferred examples thereof include "$C_{1-4}$ alkylsulfonyl group". Specific examples of the "$C_{1-6}$ alkylsulfonyl group" include methylsulfonyl, ethylsulfonyl, and propylsulfonyl.

The "$C_{1-6}$ alkyl" moiety of the term "$C_{1-6}$ alkylsulfonylamino group" used herein is as defined in the above "$C_{1-5}$ alkyl". Preferred examples thereof include "$C_{1-4}$ alkylsulfonylamino group". Specific examples of the "$C_{1-6}$ alkylsulfonylamino group" include methylsulfonylamino, ethylsulfonylamino, and propylsulfonylamino.

The "$C_{1-6}$ alkoxy" moiety of the term "$C_{1-6}$ alkoxycarbonylamino group" used herein is as defined in the above "$C_{1-6}$ alkoxy". Preferred examples thereof include "$C_{1-4}$ alkoxy-carbonylamino group". Specific examples of the "$C_{1-6}$ alkoxy-carbonylamino group" include methoxycarbonylamino, ethoxycarbonylamino, and propoxycarbonylamino.

The term "$C_{1-6}$ alkyl-carbonyloxy group" used herein means an oxy group substituted with the above "$C_{1-6}$ alkyl-carbonyl group". Preferred examples thereof include "$C_{1-4}$ alkyl-carbonyloxy group". Specific examples of the "$C_{1-6}$ alkyl-carbonyloxy group" include acetoxy, propionyloxy, and butyryloxy.

The term "aminosulfonyl group" used herein means a sulfo group wherein hydroxy group therein is substituted with amino group.

Examples of the substituent in the term "optionally-substituted $C_{1-4}$ alkylene group" include hydroxy group, halogen atom, $C_{3-7}$ cycloalkyl group, and $C_{1-6}$ alkoxy group, preferably fluorine atom.

Examples of the substituent in the terms "optionally-substituted $C_{5-10}$ aryl group", "optionally-substituted $C_{3-10}$ cycloalkyl group", "optionally-substituted 5- to 10-membered heteroaryl group", "optionally-substituted benzene ring", "optionally-substituted pyridine ring", "optionally-substituted pyrimidine ring", "optionally-substituted pyridazine ring", "optionally-substituted pyrazine ring", "optionally-substituted 5-membered heteroaryl ring" include (a) halogen atom,
(b) $C_{1-6}$ alkyl which may be optionally substituted with the same or different 1 to 3 groups selected from the group consisting of halogen atom, hydroxy, and $C_{1-6}$ alkoxy,
(c) $C_{1-6}$ alkoxy which may be optionally substituted with the same or different 1 to 3 groups selected from the group consisting of halogen atom, hydroxy, and $C_{1-6}$ alkoxy,
(d) cyano,
(e) $C_{6-10}$ aryl which may be optionally substituted with the same or different 1 to 4 groups selected from the group consisting of halogen atom, $C_{1-6}$ alkyl, and $C_{1-6}$ alkoxy, and
(f) 5- or 6-membered heteroaryl which may be optionally substituted with the same or different 1 to 4 groups selected from the group consisting of halogen atom, $C_{1-6}$ alkyl, and $C_{1-6}$ alkoxy,
(g) $C_{6-10}$ aryloxy which may be optionally substituted with the same or different 1 to 4 groups selected from the group consisting of halogen atom, $C_{1-6}$ alkyl, and $C_{1-6}$ alkoxy,
(h) hydroxy,
(i) amino which may be optionally substituted with the same or different 1 to 2 $C_{1-6}$ alkyl groups,
(j) aminocarbonyl wherein the amino moiety thereof may be optionally substituted with the same or different 1 to 2 $C_{1-6}$ alkyl groups,
(k) $C_{1-6}$ alkoxy-carbonyl wherein the alkoxy moiety thereof may be optionally substituted with the same or different 1 to 3 groups selected from the group consisting of halogen atom, hydroxy, and $C_{1-6}$ alkoxy,
(l) $C_{1-6}$ alkyl-carbonyl wherein the alkyl moiety thereof may be optionally substituted with the same or different 1 to 3 groups selected from the group consisting of halogen atom, hydroxy, and $C_{1-6}$ alkoxy,
(m) $C_{1-6}$ alkylsulfonyl wherein the alkyl moiety thereof may be optionally substituted with the same or different 1 to 3 groups selected from the group consisting of halogen atom, hydroxy, and $C_{1-6}$ alkoxy,
(n) $C_{1-6}$ alkyl-carbonylamino wherein the alkyl moiety thereof may be optionally substituted with the same or different 1 to 3 groups selected from the group consisting of halogen atom, hydroxy, and $C_{1-6}$ alkoxy,
(o) $C_{1-6}$ alkylsulfonylamino wherein the alkyl moiety thereof may be optionally substituted with the same or different 1 to 3 groups selected from the group consisting of halogen atom, hydroxy, and $C_{1-6}$ alkoxy,
(p) $C_{1-6}$ alkoxy-carbonylamino wherein the alkoxy moiety thereof may be optionally substituted with the same or different 1 to 3 groups selected from the group consisting of halogen atom, hydroxy, and $C_{1-6}$ alkoxy,
(q) $C_{1-6}$ alkyl-carbonyloxy wherein the alkyl moiety thereof may be optionally substituted with the same or different 1 to 3 groups selected from the group consisting of halogen atom, hydroxy, and $C_{1-6}$ alkoxy,
(r) aminosulfonyl wherein the amino moiety thereof may be optionally substituted with the same or different 1 to 2 $C_{1-6}$ alkyl groups, and
(s) $C_{3-10}$ cycloalkyl which may be optionally substituted with the same or different 1 to 4 groups selected from the group consisting of halogen atom, hydroxy, and $C_{1-6}$ alkoxy.

In the present compound of formula (1), $W^1$, $W^2$, $R^1$, $R^2$, $R^4$, X, n, m, p, ring $Q^1$, and $Cy^1$ are preferably those shown below, but the technical scope of the present invention should not be limited to the following compounds.

$W^1$ is preferably $C_{1-4}$ alkylene group which may be optionally substituted with the same or different 1 to 4 groups selected from the group consisting of halogen atom, hydroxy, and $C_{1-6}$ alkoxy. $W^1$ is more preferably methylene group which may be optionally substituted with the same or different 1 to 2 halogen atoms or ethylene group which may be optionally substituted with the same or different 1 to 4 halogen atoms, furthermore preferably methylene group.

$W^2$-$Cy^1$ preferably includes —$NR^{3a}C(O)$-$Cy^1$ or $C(O)NR^{3a}$-$Cy^1$ wherein $R^{3a}$ is hydrogen atom or $C_{1-6}$ alkyl group. $W^2$-$Cy^1$ is more preferably —$NHC(O)$-$Cy^1$ or —$C(O)NH$-$Cy^1$, furthermore preferably —$NHC(O)$-$Cy^1$.

Preferably, $R^1$ and $R^2$ independently includes hydrogen atom, halogen atom, $C_{1-4}$ alkyl group which may be optionally substituted with the same or different 1 to 3 halogen atoms. $R^1$ and $R^2$ are more preferably hydrogen atom, chlorine atom, or methyl group, furthermore preferably hydrogen atom.

Ring $Q^1$ preferably includes
(1) $C_{6-10}$ aryl group which may be optionally substituted with the same or different 1 to 4 groups selected from the group consisting of:
(a) halogen atom,
(b) $C_{1-5}$ alkyl which may be optionally substituted with the same or different 1 to 3 groups selected from the group consisting of halogen atom, hydroxy, and $C_{1-6}$ alkoxy,
(c) $C_{1-6}$ alkoxy which may be optionally substituted with the same or different 1 to 3 groups selected from the group consisting of halogen atom, hydroxy, and $C_{1-6}$ alkoxy,
(d) cyano,
(e) phenyl which may be optionally substituted with the same or different 1 to 4 groups selected from the group consisting of halogen atom, $C_{1-6}$ alkyl, and $C_{1-6}$ alkoxy,
(f) 5- or 6-membered heteroaryl which may be optionally substituted with the same or different 1 to 4 groups selected from the group consisting of halogen atom, $C_{1-6}$ alkyl, and $C_{1-6}$ alkoxy,
(g) phenoxy which may be optionally substituted with the same or different 1 to 4 groups selected from the group consisting of halogen atom, $C_{1-6}$ alkyl, and $C_{1-6}$ alkoxy,
(h) hydroxy,
(i) amino which may be optionally substituted with the same or different 1 to 2 alkyl groups, and
(j) aminocarbonyl wherein the amino moiety thereof may be optionally substituted with the same or different 1 to 2 $C_{1-6}$ alkyl groups,
(2) $C_{3-10}$ cycloalkyl group which may be optionally substituted with the same or different 1 to 5 groups selected from the group consisting of (a) to (j) defined in the above (1), or
(3) 5- to 10-membered heteroaryl group which may be optionally substituted with the same or different 1 to 5 groups selected from the group consisting of (a) to (j) defined in the above (1).

Ring $Q^1$ preferably includes
(1) phenyl group which may be optionally substituted with the same or different 1 to 5 groups selected from the group consisting of:
(a) halogen atom,
(b) $C_{1-6}$ alkyl which may be optionally substituted with the same or different 1 to 3 groups selected from the group consisting of halogen atom, hydroxy, and $C_{1-6}$ alkoxy,
(c) $C_{1-6}$ alkoxy which may be optionally substituted with the same or different 1 to 3 groups selected from the group consisting of halogen atom, hydroxy, and $C_{1-6}$ alkoxy,
(d) cyano,
(e) phenyl which may be optionally substituted with the same or different 1 to 4 groups selected from the group consisting of halogen atom, $C_{1-6}$ alkyl, and $C_{1-6}$ alkoxy, and
(f) 5- or 6-membered heteroaryl which may be optionally substituted with the same or different 1 to 4 groups selected from the group consisting of halogen atom, $C_{1-6}$ alkyl, and $C_{1-6}$ alkoxy, or
(2) pyridyl group which may be optionally substituted with the same or different 1 to 4 groups selected from the group consisting of (a) to (f) defined in the above (1).

Ring $Q^1$ furthermore preferably includes phenyl group which may be optionally substituted with the same or different 1 to 5 groups selected from the group consisting of:
(a) halogen atom,
(b) $C_{1-6}$ alkyl which may be optionally substituted with the same or different 1 to 3 halogen atoms, and
(c) $C_{1-6}$ alkoxy which may be optionally substituted with the same or different 1 to 3 halogen atoms.

$Cy^1$ preferably includes the group of formula (11) in the above [1].

Preferred aspects of the group of formula (11) in the above [1] include the group of formula (21) in the above [9].

More preferably, it includes the following groups:

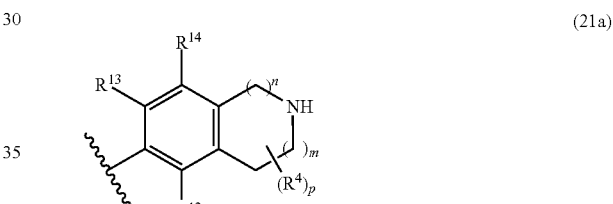
(21a)

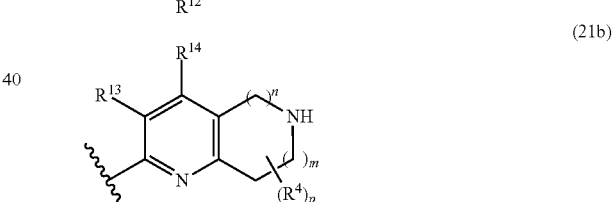
(21b)

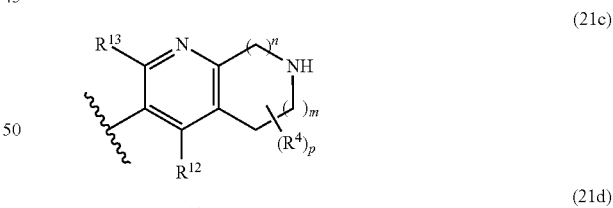
(21c)

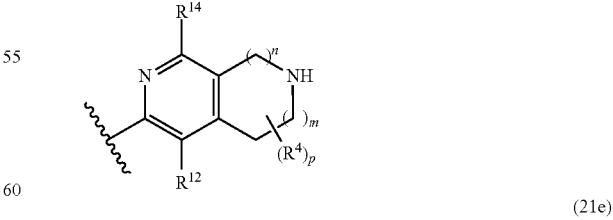
(21d)

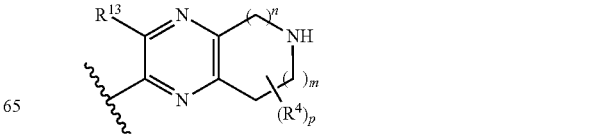
(21e)

-continued

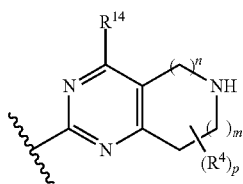

(21f)

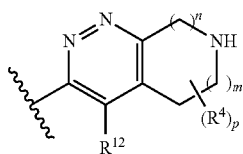

(21g)

wherein R⁴, n, m, and p are as defined in the above [1]; and R, R¹³ and R¹⁴ are as defined in the above [9].

Furthermore preferably, it includes the above groups of formulae (21a), (21b), (21c) and (21d).

Preferred aspects of the group of formula (12) in the above [1] include the group of formula (22) in the above [9].

More preferably, it includes the following groups:

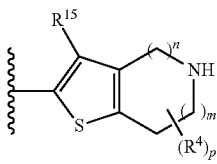

(22a)

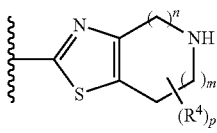

(22b)

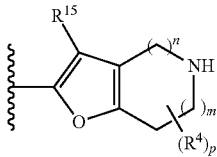

(22c)

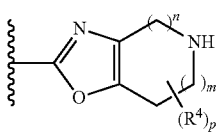

(22d)

wherein R⁴, n, m, and p are as defined in the above [1]; and R¹⁵ is as defined in the above [9].

It furthermore preferably includes the above groups of formulae (22a) and (22b), most preferably the above group of formula (22a).

Preferred aspects of the group of formula (13) in the above [1] include the group of formula (23) in the above [9].

More preferably, it includes the following groups:

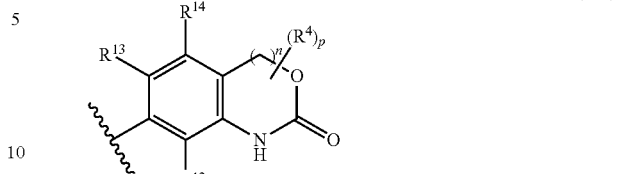

(23a)

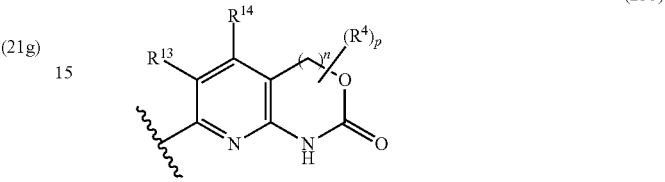

(23b)

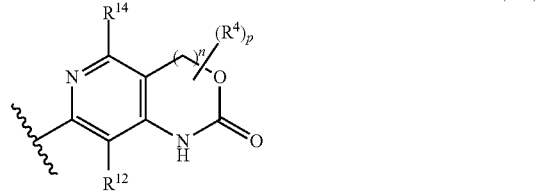

(23c)

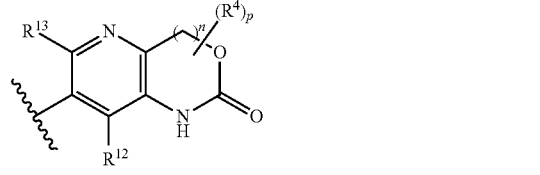

(23d)

wherein R⁴, n, and p are as defined in the above [1]; and R12, R¹³, and R¹⁴ are as defined in the above [9].

Furthermore preferably, it includes the above group of formula (23a).

$R^4$ preferably includes hydrogen atom, fluorine atom, or $C_{1-4}$ alkyl. $R^4$ is more preferably hydrogen atom.

p in the above [1] and q in the above [9] are independently selected from 1, 2, 3, 4, or 5. Preferably, p and q are independently 1, 2, or 3. When the number of the replaceable positions on the ring having the substituent $R^4$ or $R^{11}$ is less than 5, p and q are independently selected from the maximum replaceable number of $R^4$ or $R^{11}$. For example, when ring $Q^1$ is pyridyl group, q is selected from 1, 2, 3, or 4.

X preferably includes $NR^5$ wherein $R^5$ is hydrogen atom or $C_{1-6}$ alkyl group which may be optionally substituted with the same or different 1 to 3 halogen atoms, and more preferably it is NH.

With regard to n and m, preferably n is 1 and m is 1; or n is 2 and m is 0. More preferably, n is 1 and m is 1.

The present compound may be in the forms of a hydrate and/or a solvate. Thus, the present compound also encompasses hydrate and/or solvate such as ethanol solvate. Furthermore, the present compound encompasses all types of crystal forms of the present compound.

Specific examples of the pharmaceutically acceptable salt of the compound of formula (1) include an inorganic acid salt such as hydrochloride, hydrobromide, sulfate, phosphate, and nitrate; and an organic acid salt such as acetate, propionate, oxalate, succinate, lactate, malate, tartrate, citrate, maleate, fumarate, methanesulfonate, p-toluenesulfonate, benzenesulfonate, and ascorbate.

The compound of formula (1) may be in the form of a tautomer. Thus, the present compound also encompasses the tautomer of the compound of formula (1).

The compound of formula (1) may contain one or more asymmetric carbon atoms. Thus, the present compound encompasses not only racemic forms of the compound of formula (1) but also optically-active forms thereof. When the compound of formula (1) contains two or more asymmetric carbon atoms, the compound can result in various stereoisomerisms. Thus, the present compound also encompasses the stereoisomer of the compound and a mixture or isolate thereof.

Also, the compound of formula (1) encompasses the compound wherein one or more of $^1H$ are replaced with $^2H(D)$ (i.e. deuterated form).

Preparations

The present compounds can be prepared according to processes shown below and according to the processes in combination with known compounds and known synthesis processes.

As appropriate, each compound used as a starting compound may be used in the salt form. The shown processes are just examples to prepare the compounds, and may be optionally modified by those skilled in the organic synthesis field.

In each process shown below, any functional groups which need to be protected may be optionally protected and then deprotected after the reaction or reactions are completed to give the desired compound even though the use of protective groups is not specifically described.

The protective group used herein includes any conventional groups described in various literatures, for example, T. W. Greene and P. G. M. Wuts, "Protective Groups in Organic Synthesis", 3rd Ed., John Wiley and Sons, inc., New York (1999). In more detail, specific examples of the protective groups for amino group include benzyloxycarbonyl, tert-butoxycarbonyl, acetyl, and benzyl, and specific examples of the protective groups for hydroxy group include trialkylsilyl, acetyl, and benzyl.

The protective groups can be introduced and cleaved according to commonly-used methods in synthetic organic chemistry (e.g. the method described in T. W. Greene and P. G. M. Nuts, "Protective Groups in Organic Synthesis", 3rd Ed., John Wiley and Sons, inc., New York (1999)) and similar methods thereto.

Preparation 1

One of the compounds of formula (1), the compound of formula (1-8) is prepared by linking each fragment in positions a, b and c, respectively:

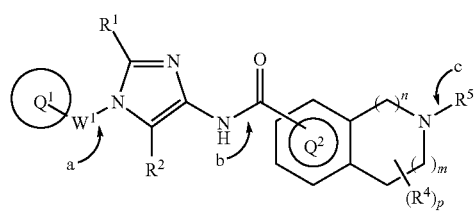

wherein $W^1$, $R^1$, $R^2$, $R^4$, $R^5$, n, m, p, ring $Q^1$, and ring $Q^2$ are as defined in the above [1].

The processes for forming each bond in positions a, b and c can be illustrated as follows, but the order of procedure for forming each bond may be optionally changed:

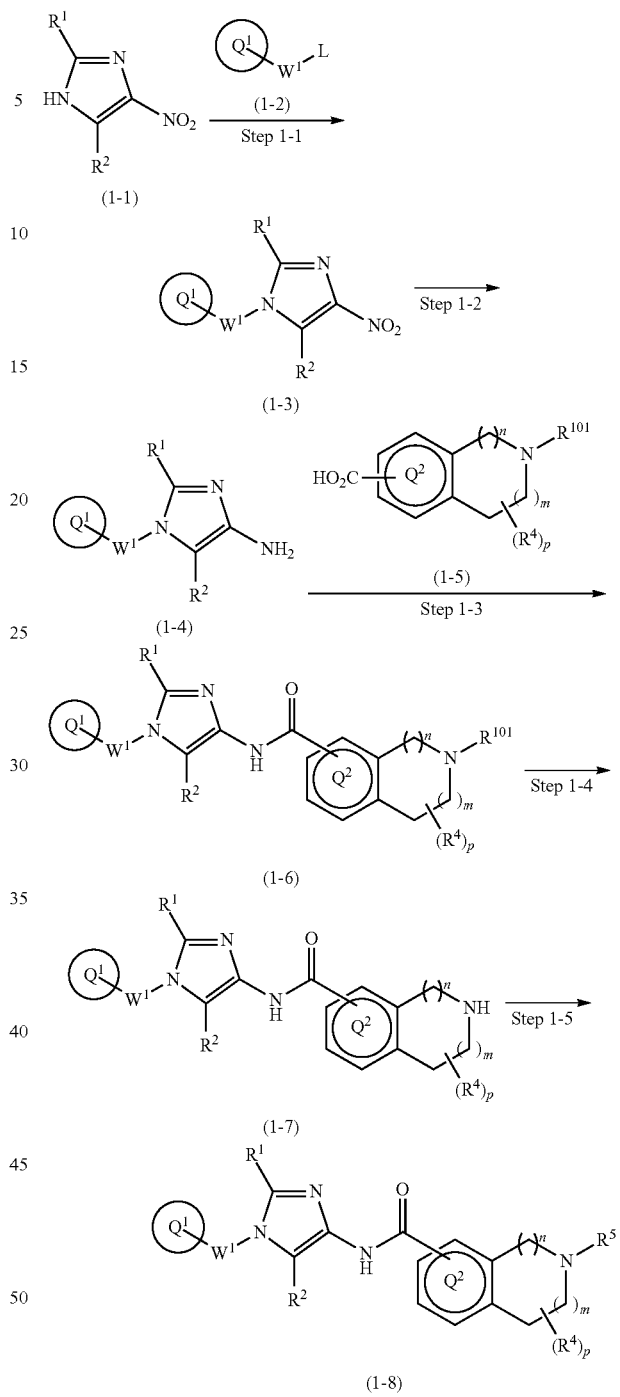

wherein $W^1$, $R^1$, $R^2$, $R^4$, $R^5$, n, m, p, ring $Q^1$, and ring $Q^2$ are as defined in the above [1]; L is a leaving group (such as iodine atom, bromine atom, chlorine atom and substituted sulfonyl group (e.g. methanesulfonyl group and p-toluenesulfonyl group)); and $R^{101}$ is benzyloxycarbonyl (Cbz) group, Boc group, benzyl group, 4-methoxybenzyl group, or 9-fluorenylmethyloxycarbonyl (Fmoc) group.

Compound (1-1) may be a commercially available product or be prepared according to known synthesis processes (e.g. New Version of Heterocyclic Compound (advanced level) edited by Kodansha Scientific Ltd.).

Step 1-1: Preparation Process of Compound (1-3)

Compound (1-3) is prepared by the alkylation reaction of compound (1-1) with compound (1-2) in an inert solvent in the presence of a base.

Specific examples of the base include an organic base such as triethylamine, diisopropylethylamine, and pyridine; an inorganic base such as potassium carbonate, sodium carbonate, cesium carbonate, potassium hydrogen carbonate, sodium hydrogen carbonate, potassium dihydrogen phosphate, dipotassium hydrogen phosphate, potassium phosphate, sodium dihydrogen phosphate, disodium hydrogen phosphate, sodium phosphate, potassium hydroxide, sodium hydroxide, and sodium hydride; and a metal alkoxide such as sodium methoxide and potassium tert-butoxide.

Specific examples of the inert solvent include a halogenated hydrocarbon such as chloroform and dichloromethane; an aromatic hydrocarbon such as toluene; an ether-type solvent such as diethyl ether, tetrahydrofuran (THF), and 1,4-dioxane; an aprotic polar solvent such as acetonitrile, acetone, methyl ethyl ketone, N,N-dimethylformamide, N-methyl-2-pyrrolidinone, and dimethylsulfoxide; a basic solvent such as pyridine; and a mixture thereof.

The reaction temperature is typically 0° C. to 150° C., preferably 20° C. to 100° C., but is not limited thereto. The reaction time is typically 30 minutes to 48 hours, preferably 30 minutes to 10 hours.

Step 1-2: Preparation Process of Compound (1-4)

Compound (1-4) is prepared by reducing the nitro group in compound (1-3). For example, reactions such as reduction under an acidic condition with a metal such as zinc, iron and tin or a metal salt such as tin (II) chloride; reduction with a sulfide such as sodium dithionite ($Na_2S_2O_4$); or catalytic hydrogenation with a metal catalyst such as palladium/carbon, Raney nickel, platinum oxide/carbon, and rhodium/carbon under hydrogen atmosphere are used.

In the reduction reaction with a metal or a metal salt, the amount of the metal or the metal salt to be used is typically about 1 mole to 100 moles, preferably about 10 moles to 30 moles per mole of compound (1-3). Also, the amount of the acid to be used is typically about 1 mole to 100 moles, preferably about 10 moles to 30 moles per mole of compound (1-3). The reduction reaction is typically carried out in a solvent which has no negative effect on the reaction (e.g. ethanol). The reaction temperature is typically 0° C. to 100° C., but is not limited thereto. The reaction time is typically 30 minutes to 8 hours.

In the catalytic hydrogenation reaction, the amount of the metal catalyst to be used for compound (1-3) is typically 0.1% by weight to 1000% by weight, preferably 1% by weight to 100% by weight. The reaction may be carried out in a solvent such as an alcohol such as methanol; an ether such as tetrahydrofuran; and an ester such as ethyl acetate. The hydrogen pressure is typically 1 atm to 100 atms, preferably 1 atm to 5 atms. The reaction temperature is typically 0° C. to 120° C., preferably 20° C. to 80° C., but is not limited thereto. The reaction time is typically 30 minutes to 72 hours, preferably 1 hour to 48 hours.

Also, the reaction may be carried out in the presence of an acid catalyst, as appropriate. For example, an organic acid such as formic acid, acetic acid and trifluoroacetic acid, and an inorganic acid such as sulfuric acid, hydrochloric acid and hydrobromic acid are used as the acid catalyst. The amount of the acid to be used is 0.1 mole or more per mole of compound (1-3).

Step 1-3: Preparation Process of Compound (1-6)

Compound (1-6) is prepared by reacting compound (1-4) with compound (1-5) in an inert solvent in the presence of a condensation agent.

The reaction may be carried out in the presence of a base, as appropriate. The reaction temperature is typically about −20° C. to the boiling point of the used solvent, but is not limited thereto. The reaction time is typically 10 minutes to 48 hours, which may vary according to various conditions such as a reaction temperature, a condensation agent, a starting material, and a solvent to be used.

Specific examples of the condensation agent include dicyclohexylcarbodiimide (DCC), diisopropylcarbodiimide (DIPC), 1-ethyl-3-(3-dimethylaminopropyl)-carbodiimide (WSC), benzotriazol-1-yl-tris(dimethylamino)phosphonium hexafluorophosphate (BOP), diphenylphosphoryl azide (DPPA), N,N-carbonyldiimidazole (CDI), O-(benzotriazol-1-yl)-N,N,N',N'-tetramethyluronium hexafluorophosphate (HBTU), and O-(7-azabenzotriazol-1-yl)-N,N,N',N'-tetramethyluronium hexafluorophosphate (HATU). As appropriate, the reaction may be carried out with the addition of an additive such as N-hydroxysuccinimide (HOSu), 1-hydroxybenzotriazole (HOBt), and 3-hydroxy-4-oxo-3,4-dihydro-1,2,3-benzotriazine (HOOBt).

Specific examples of the base include an organic base such as triethylamine, diisopropylethylamine and pyridine; an inorganic base such as potassium carbonate, sodium carbonate, cesium carbonate, potassium hydrogen carbonate, sodium hydrogen carbonate, potassium dihydrogen phosphate, dipotassium hydrogen phosphate, potassium phosphate, sodium dihydrogen phosphate, disodium hydrogen phosphate, sodium phosphate, potassium hydroxide, sodium hydroxide and sodium hydride; and a metal alkoxide such as sodium methoxide and potassium tert-butoxide.

Specific example of the inert solvent include a halogenated hydrocarbon such as chloroform and dichloromethane; an aromatic hydrocarbon such as toluene; an ether-type solvent such as diethyl ether, tetrahydrofuran (THF) and 1,4-dioxane; an aprotic polar solvent such as acetonitrile, acetone, methyl ethyl ketone, dimethylformamide, N-methyl-2-pyrrolidinone and dimethylsulfoxide; a basic solvent such as pyridine; and a mixture thereof.

Compound (1-6) is also prepared by reacting compound (1-4) with an acid halide or an acid anhydride derived from compound (1-5) in an inert solvent in the presence of a base.

Step 1-4: Preparation Process of Compound (1-7)

Compound (1-7) is prepared using compound (1-6) as the starting material according to a similar process to the process described in literatures (such as Protective Groups in Organic Synthesis $3^{rd}$ Edition (John Wiley & Sons, Inc.)).

Step 1-5: Preparation Process of Compound (1-8)

Compound (1-8) is prepared by the reductive amination of compound (1-7) with an alkylketone or an alkylaldehyde in an appropriate inert solvent in the presence of a reducing agent.

The reaction may be carried out in the presence of a base, an acid or other additives, as appropriate. The reaction temperature is typically about −20° C. to the boiling point of the used solvent. The reaction time is typically 10 minutes to 48 hours, which may vary according to various conditions such as a reaction temperature, a reducing agent, a starting material, and a solvent to be used.

Specific examples of the reducing agent include sodium cyanoborohydride, sodium triacetoxyborohydride, and sodium borohydride.

Specific examples of the base include an organic base such as triethylamine, diisopropylethylamine and pyridine; and an inorganic base such as potassium carbonate, sodium carbonate, cesium carbonate, potassium hydrogen carbonate, sodium hydrogen carbonate, potassium dihydrogen phosphate, dipotassium hydrogen phosphate, potassium phosphate, sodium dihydrogen phosphate, disodium hydrogen phosphate, sodium phosphate, potassium hydroxide, sodium hydroxide and sodium hydride.

Specific examples of the acid include an organic acid such as acetic acid, trifluoroacetic acid and methanesulfonic acid; and an inorganic acid such as hydrochloric acid and sulfuric acid.

Specific examples of the solvent include water; acetonitrile; a halogenated hydrocarbon such as chloroform and dichloromethane; an aromatic hydrocarbon such as benzene and toluene; an ether-type solvent such as 1,2-dimethoxyethane, tetrahydrofuran and 1,4-dioxane; an alcohol-type solvent such as methanol, ethanol and 2-propanol; an aprotic polar solvent such as dimethylformamide and N-methyl-2-pyrrolidinone; and a mixture thereof.

Preparation 2

The compound of formula (2-5) is prepared according to, for example, the following process.

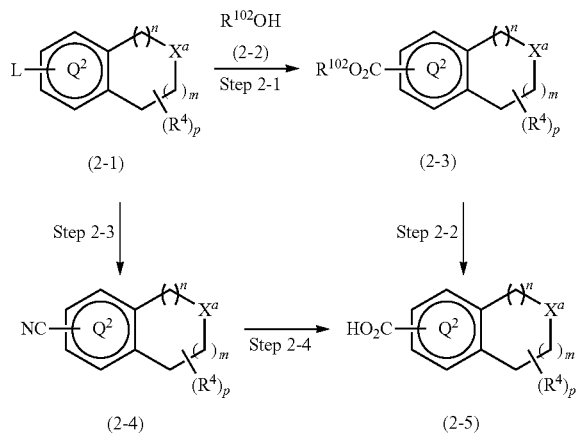

wherein $R^4$, n, m, p, and ring $Q^2$ are as defined in the above [1]; $X^a$ is O or $NR^{101}$; $R^{101}$ is Cbz group, Boc group, benzyl group, 4-methoxybenzyl group or Fmoc group; $R^{102}$ is $C_{1-6}$ alkyl group; and L is a leaving group (such as iodine atom, bromine atom, chlorine atom and substituted sulfonyl group (e.g. methanesulfonyl group and p-toluenesulfonyl group)).

Compound (2-1) may be a commercially available product or be prepared according to known synthesis processes (e.g. WO 2009/056556, WO 2006/065215).

Step 2-1: Preparation Process of Compound (2-3)

Compound (2-3) is prepared by introducing ester group to compound (2-1) under carbon monoxide atmosphere in the presence of palladium catalyst, phosphorus ligand, an alcohol of formula (2-2) in an inert solvent.

The pressure of carbon monoxide is selected according to various conditions such as a reaction temperature, a starting material, and a solvent to be used, as appropriate, and is typically 1 atm to 100 atms, preferably 1 atm to 5 atms. The reaction temperature is typically about −20° C. to the boiling point of the used solvent, preferably room temperature to the boiling point of the used solvent. The reaction may be carried out using a microwave reaction device. The reaction time is typically 10 minutes to 48 hours, which may vary according to various conditions such as a reagent, a reaction temperature, a starting material, and a solvent to be used.

Examples of the palladium catalyst include tetrakis(triphenylphosphine)palladium and di-tert-butylphosphinepalladium.

Examples of the inert solvent include N,N-dimethylformamide, N-methyl-2-pyrrolidinone, 1,4-dioxane and a mixture thereof.

In addition, an organic base such as N,N-diisopropylethylamine and triethylamine may be added thereto, as appropriate.

Step 2-2: Preparation Process of Compound (2-5)

Compound (2-5) is prepared by hydrolyzing compound (2-3) according to a similar process to a known process (e.g. Protective Groups in Organic Synthesis 3$^{rd}$ Edition (John Wiley & Sons, Inc.), Comprehensive Organic Transformation, by R. C. Larock et al., VCH publisher Inc., 1989).

Step 2-3: Preparation Process of Compound (2-4)

Compound (2-4) is prepared by the cyanation of compound (2-1) in an inert solvent in the presence of palladium catalyst, phosphorus ligand and a cyanating agent.

The reaction temperature is typically about −20° C. to the boiling point of the used solvent, preferably room temperature to the boiling point of the used solvent. The reaction may be carried out using a microwave reaction device. The reaction time is typically 10 minutes to 48 hours, which may vary according to various conditions such as a reaction temperature, a reagent, a starting material, and a solvent to be used.

Examples of the cyanating agent include sodium cyanide, potassium cyanide and zinc cyanide, preferably zinc cyanide.

Examples of the palladium catalyst include tetrakis(triphenylphosphine)palladium and di-tert-butylphosphinepalladium.

Examples of the inert solvent include N,N-dimethylformamide, N-methyl-2-pyrrolidinone, 1,4-dioxane and a mixture thereof.

Step 2-4: Preparation Process of Compound (2-5)

Compound (2-5) is prepared by hydrolyzing the cyano group in compound (2-4) in an appropriate solvent in the presence of a base.

The reaction temperature is typically about −20° C. to the boiling point of the used solvent, preferably room temperature to the boiling point of the used solvent. The reaction time is typically 10 minutes to 48 hours, which may vary according to various conditions such as a reaction temperature, a starting material, and a solvent to be used.

Examples of the base include sodium hydroxide and potassium hydroxide.

Examples of the solvent to be used include methanol, ethanol, 2-propanol, acetone, tetrahydrofuran, 1,4-dioxane, water and a mixture thereof.

Preparation 3

The compound of formula (3-6) is prepared by, for example, the following process.

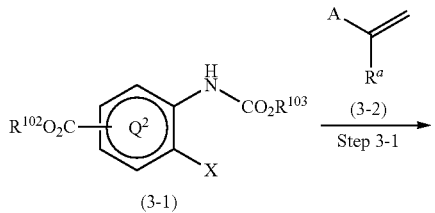

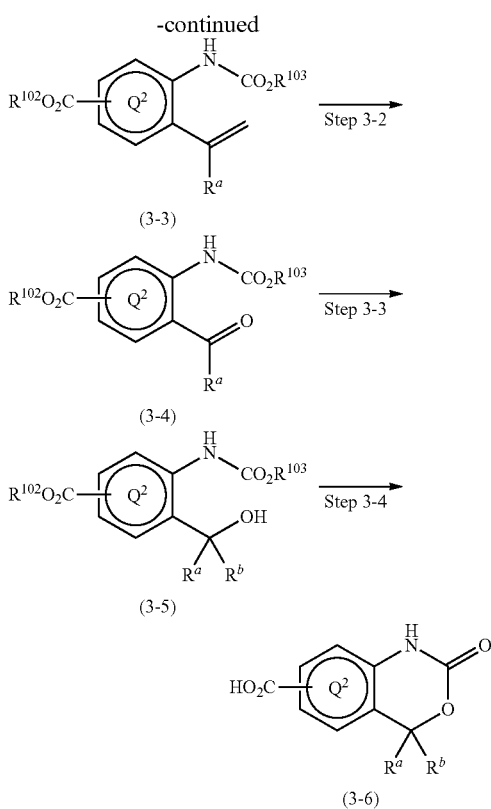

wherein ring $Q^2$ is as defined in the above [1]; A is boronic acid or boronate; $R^{102}$ is $C_{1-6}$ alkyl group, $R^{103}$ is $C_{1-6}$ alkyl group, benzyl group, allyl group, etc.; $R^a$ and $R^b$ are the same or different hydrogen atom or methyl group; and X is halogen atom.

Step 3-1: Preparation Process of Compound (3-3)

Compound (3-3) is prepared by reacting compound (3-1) with compound (3-2) in an inert solvent in the presence of palladium catalyst and a base.

Specific examples of the palladium catalyst include tetrakis(triphenylphosphine)palladium (0), bis(dibenzylideneacetone)palladium (0), tris(dibenzylideneacetone)dipalladium (0), bis(tri-tert-butylphosphine)palladium (0), [1,1'-bis(diphenylphosphino)ferrocene]palladium (II) dichloride.

Examples of the base include an inorganic base such as potassium carbonate, sodium carbonate, cesium carbonate, potassium phosphate, potassium hydroxide and sodium hydroxide.

Examples of the inert solvent include toluene, 1,2-dimethoxyethane, 1,4-dioxane, DMF and a mixture thereof.

The reaction temperature is typically about 50° C. to 150° C., preferably 80° C. to 120° C., but is not limited thereto.

Also, the reaction may be carried out under microwave irradiation. The reaction time is typically 1 hour to 24 hours, preferably 2 hours to 12 hours.

Step 3-2: Preparation Process of Compound (3-4)

Compound (3-4) is prepared by reacting compound (3-3) with osmium tetroxide or potassium osmate (IV) dihydrate in the presence of sodium periodate.

Examples of the solvent to be used include acetone, 1,4-dioxane, THF, tert-butanol, water and a mixture thereof.

The reaction temperature is typically about 0° C. to 100° C., preferably 25° C. to 50° C., but is not limited thereto. The reaction time is typically 1 hour to 72 hours, preferably 6 hours to 24 hours.

Also, compound (3-4) is prepared by treating compound (3-3) with oxygen currents including ozone and then reacting the treated compound with a reducing agent such as dimethyl sulfide at room temperature or −78° C. in a solvent such as dichloromethane, ethyl acetate and methanol. The reaction temperature is typically −78° C. to room temperature, but is not limited thereto. The reaction time is typically 1 hour to 72 hours, preferably 6 hours to 24 hours.

Step 3-3: Preparation Process of Compound (3-5)

Compound (3-5) is prepared by reacting compound (3-4) with an organometallic reagent or a hydride reducing agent.

Specific examples of the organometallic reagent include methyllithium reagent and methyl Grignard reagent.

Specific examples of the hydride reducing agent include sodium borohydride and sodium cyanoborohydride.

The solvent used in the reaction with the organometallic reagent includes THF, diethyl ether and a mixture thereof, and the solvent used in the reaction with the hydride reducing agent includes methanol, ethanol, dichloromethane, toluene and a mixture thereof.

The reaction temperature is typically −78° C. to 50° C., preferably 0° C. to 25° C., but is not limited thereto. The reaction time is typically 5 minutes to 12 hours, preferably 30 minutes to 6 hours.

Step 3-4: Preparation Process of Compound (3-6)

Compound (3-6) is prepared by reacting compound (3-5) with aqueous alkali solution.

Examples of the aqueous alkali solution include ageous sodium hydroxide solution, aqueous potassium hydroxide solution and aqueous lithium hydroxide solution, and the concentraton thereof is typically 1 to 10 mol/L, preferably 1 to 5 mol/L.

Examples of the solvent to be used include methanol, ethanol, 2-propanol, THF, 1,4-dioxane and a mixture threof.

The reaction temperature is typically 0° C. to 100° C., preferably 0° C. to 50° C., but is not limited thereto. The reaction time is typically 10 minutes to 24 hours, preferably 30 minutes to 12 hours.

Preparation 4

The compound of formula (4-1) may be a commercially available product or be prepared according to known synthesis processes (e.g. J. Med. Chem., 2004, 5167-5182, Bioorg. Med. Chem., 2006, 1309-1330.).

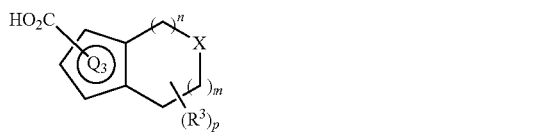

(4-1)

Preparation 5

One of the compounds of formula (1), the compound of formula (5-5) is prepared according to, for example, the following process.

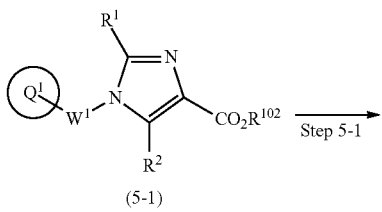

(5-1)

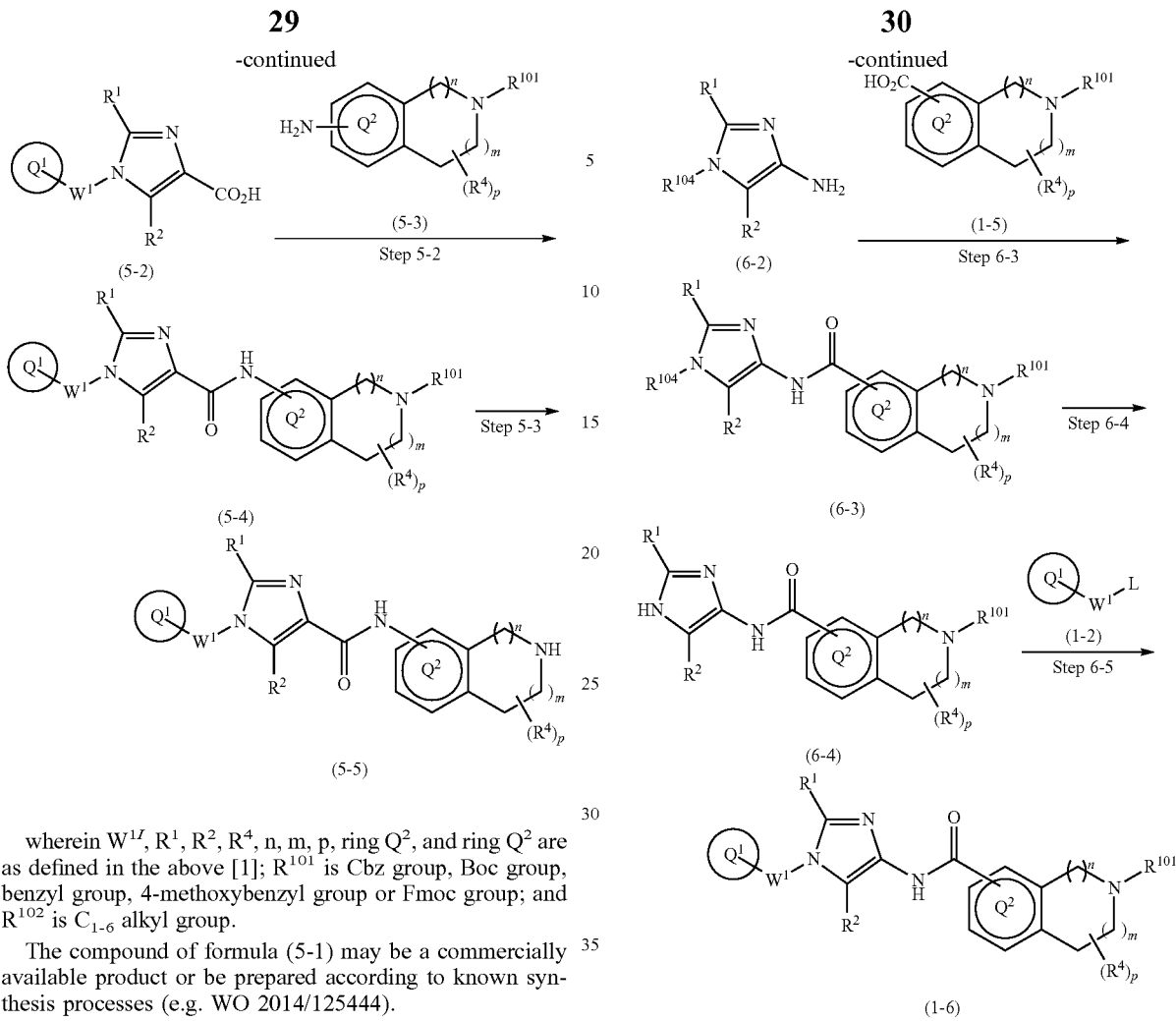

wherein $W^{1'}$, $R^1$, $R^2$, $R^4$, n, m, p, ring $Q^2$, and ring $Q^2$ are as defined in the above [1]; $R^{101}$ is Cbz group, Boc group, benzyl group, 4-methoxybenzyl group or Fmoc group; and $R^{102}$ is $C_{1-6}$ alkyl group.

The compound of formula (5-1) may be a commercially available product or be prepared according to known synthesis processes (e.g. WO 2014/125444).

Step 5-1: Preparation Process of Compound (5-2)

Compound (5-2) is prepared by hydrolyzing compound (5-1) according to a similar process to a known process (e.g. Protective Groups in Organic Synthesis $3^{rd}$ Edition (John Wiley & Sons, Inc.), Comprehensive Organic Transformation, by R. C. Larock et al., VCH publisher Inc., 1989).

Step 5-2: Preparation Process of Compound (5-4)

Compound (5-4) is prepared from compounds (5-2) and (5-3) according to the process of Step 1-3.

Step 5-3: Preparation Process of Compound (5-5)

Compound (5-5) is prepared using compound (5-4) as a starting material according to a simialr process to the process described in literatures (such as Protective Groups in Organic Synthesis $3^{rd}$ Edition (John Wiley & Sons, Inc.)).

Preparation 6

The compound of formula (1-6) is prpared by, for example, the following process.

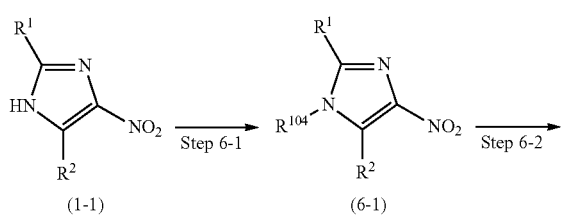

wherein $W^1$, $R^1$, $R^2$, $R^4$, n, m, p, ring $Q^1$, and ring $Q^2$ are as defined in the above [1]; L is a leaving group (such as iodine atom, bromine atom, chlorine atom and substituted sulfonyloxy group (e.g. methanesulfonyloxy group and p-toluenesulfonyloxy group)); and $R^{101}$ and $R^{104}$ are benzyloxycarbonyl (Cbz) group, Boc group, benzyl group, 4-methoxybenzyl group, 2-(trimethylsilyl)ethoxymethyl group or 9-fluorenylmethyloxycarbonyl (Fmoc) group.

Step 6-1: Preparation Process of Compound (6-1)

Compound (6-1) is prepared by introducing a protective group to N atom of the imidazole group in compound (1-1) in an inert solvent. Examples of the protective group include 2-(trimethylsilyl)ethoxymethyl, benzyloxycarbonyl, tert-butoxycarbonyl, acetyl and benzyl.

For example, when 2-(trimethylsilyl)ethoxymethyl group is introduced, compound (6-1) is prepared by reacting compound (1-1) with 2-(trimethylsilyl)ethoxymethyl chloride in an inert solvent in the presence of a base.

Examples of the base include potassium carbonate, sodium carbonate, cesium carbonate, potassium-tert-butoxide, sodium hydroxide, sodium bis(trimethylsilyl)amide, lithium bis(trimethylsilyl)amide, potassium bis(trimethylsilyl)amide and lithium diisopropylamide. Examples of the inert solvent include DMF, THF, acetonitrile and a mixture thereof.

The reaction temperature is typically 0° C. to 150° C., preferably 0° C. to 100° C., but is not limited thereto. The reaction time is typically 10 minutes to 24 hours, preferably 20 minutes to 6 hours.

Step 6-2: Preparation Process of Compound (6-2)
Compound (6-2) is prepared from compound (6-1) according to the process of Step 1-2.
Step 6-3: Preparation Process of Compound (6-3)
Compound (6-3) is prepared from compounds (6-2) and (1-5) according to the process of Step 1-3.
Step 6-4: Preparation Process of Compound (6-4)
Compound (6-4) is prepared by cleaving the protective group for nitrogen atom of the imidazole group in compound (6-3) in an inert solvent.

For example, when 2-(trimethylsilyl)ethoxymethyl group is cleaved, compound (6-4) is prepared by reacting compound (6-3) with an acid or a fluorinating reagent in an inert solvent.

Examples of the acid include TFA, formic acid, hydrochloric acid, sulfuric acid, p-toluenesulfonic acid, methanesulfonic acid and (±) 10-camphorsulfonic acid.

Examples of the fluorinating reagent include tetrabutylammonium fluoride.

Examples of the solvent to be used include dichloromethane, 1,2-dichloroethane, 1,4-dioxane, THF, toluene, ethyl acetate, methanol, ethanol, 2-propanol and a mixture thereof.

The reaction temperature is typically 0° C. to 150° C., preferably 0° C. to 50° C., but is not limited thereto. The reaction time is typically 5 minutes to 24 hours, preferably 1 hour to 9 hours.

In Step 6-4, when $R^{101}$ is cleaved simultaneously with cleaving the protective group for nitrogen atom of the imidazole group, compound (6-4) is prepared by reintroducing a protecting group to $R^{101}$.

Step 6-5: Preparation Process of Compound (1-6)
Compound (1-6) is prepared from compounds (6-4) and (1-2) according to the process of Step 1-1.

Preparation 7

One of the compounds of formula (1-5), the compound of formula (7-4) is prepared according to, for example, the following process:

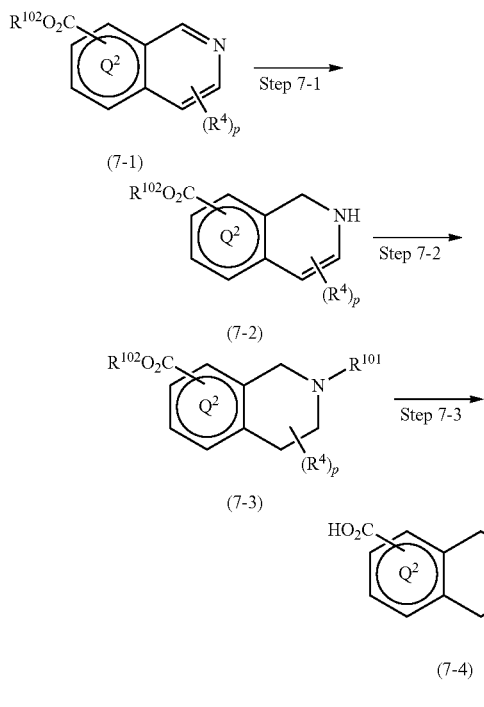

wherein $R^4$, p, and ring $Q^2$ are as defined in the above [1]; $R^{101}$ is Cbz group, Boc group, benzyl group, 4-methoxybenzyl group, or Fmoc group; and $R^{102}$ is $C_{1-6}$ alkyl group.

Compound (7-1) may be a commercially available product or be prepared according to Preparation 8.

Step 7-1: Preparation Process of Compound (7-2)
Compound (7-2) is prepared by reacting compound (7-1) with a hydride reducing agent in an inert solvent.

Specific examples of the hydride reducing agent include sodium borohydride, sodium cyanoborohydride, borane and lithium aluminium hydride.

Examples of the solvent to be used in the reaction with the hydride reducing agent include methanol, ethanol, dichloromehane, toluene, tetrahydrofuran and a mixture thereof.

The reaction temperature is typically −78° C. to 100° C., preferably 0° C. to 50° C., but is not limited thereto. The reaction time is typically 5 minutes to 12 hours, preferably 30 minutes to 6 hours.

Step 7-2: Preparation Process of Compound (7-3)
Compound (7-3) is prepared by reducing olefin in compound (7-2) with a reagent for introducing a protective group. For example, reactions such as catalytic hydrogenation reaction with a metal catalyst such as palladium/carbon, Raney nickel, platinum oxide/carbon and rhodium/carbon under hydrogen atmosphere in the presence of $Boc_2O$ are used.

In the catalytic hydrogenation reaction, the amount of the metal catalyst to be used for compound (7-2) is typically 0.1% by weight to 1000% by weight, preferably 1% by weight to 100% by weight. The reaction may be carried out in a solvent such as an alcohol such as methanol; an ether such as tetrahydrofuran; and an ester such as ethyl acetate. The hydrogen pressure is typically atm to 100 atms, preferably 1 atm to 5 atms. The reaction temperature is typically 0° C. to 120° C., preferably 20° C. to 80° C., but is not limited thereto. The reaction time is typically 30 minutes to 72 hours, preferably 1 hour to 48 hours.

When $R^{101}$ is benzyl group, 4-methoxybenzyl group, etc., compound (7-3) can be directly prepared through a pyridinium salt intermediate of compound (7-1). For example, compound (7-3) is prepared by reducing the pyridinium salt of compound (7-1) synthesized by reacting compound (7-1) with a reagent such as benzyl bromide. Reduction reactions such as reduction with a hydride reducing agent and catalytic hydrogenation with a metal catalyst such as palladium/carbon, Raney nickel, platinum oxide/carbon, and rhodium/carbon under hydrogen atmosphere are used.

Step 7-3: Preparation Process of Compound (7-4)
Compound (7-4) is prepared by hydrolyzing compound (7-3) according to a similar process to a known process (e.g. Protective Groups in Organic Synthesis 3$^{rd}$ Edition (John Wiley & Sons, Inc.), Comprehensive Organic Transformation, by R. C. Larock et al., VCH publisher Inc., 1989).

Preparation 8

One of the compounds of formula (7-1), the compound of formula (8-3) is prepared according to, for example, the following process:

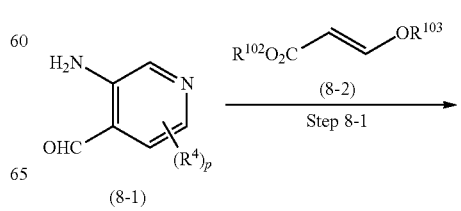

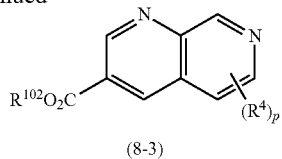

(8-3)

wherein $R^4$ and p are as defined in the above [1]; and $R^{102}$ and $R^{103}$ are $C_{1-6}$ alkyl group.

Step 8-1: Preparation Process of Compound (8-3)

Compound (8-3) is prepared by reacting compound (8-1) with compound (8-2) under an acidic condition in an inert solvent.

Examples of the acid used include trifluoroacetic acid, hydrochloric acid and sulfuric acid.

The reaction temperature is typically 0° C. to 150° C., preferably 0° C. to 100° C., but is not limited thereto. The reaction time is typically 5 minutes to 72 hours, preferably 30 minutes to 12 hours.

Examples of the inert solvent include dichloromethan, 1,2-dichloroethane, chloroform, THF, toluene, ethyl acetate and a mixture thereof.

The intermediates and desired compounds in the above preparations may be isolated and purified by a conventional purification method in organic synthetic chemistry such as neutralization, filtration, extraction, washing, drying, concentration, recrystallization, and each type of chromatography. The intermediates may be also used in the next reaction without any specific purification.

An optically-active product of the present compound can be prepared from an optically-active starting material or intermediate, or by the optical resolution of the racemate of a final product. The optical resolution method includes a physical separation method with optically-active column, and a chemical separation method such as a fractional crystallization method. A diastereomer of the present compound can be prepared by, for example, a fractional crystallization method.

The pharmaceutically acceptable salt of the compound of formula (1) can be prepared by, for example, mixing the compound of formula (1) with a pharmaceutically acceptable acid in a solvent such as water, methanol, ethanol, and acetone.

The present compound is used as, for example, an anti-tumor agent (anti-cancer agent). The applicable cancer type includes hematopoietic tumor and solid cancer, but is not limited thereto. Specific examples of the hematopoietic tumor include acute leukemia, chronic lymphatic leukemia, chronic myelocytic leukemia, polycythemia vera, malignant lymphoma, and myeloma, and specific examples of the solid cancer include brain tumor, head and neck cancer, esophageal cancer, thyroid cancer, small-cell lung cancer, non-small cell lung cancer, breast cancer, stomach cancer, gallbladder or bile duct cancer, liver cancer, pancreatic cancer, colon cancer, rectal cancer, ovarian cancer, chorioepithelioma, endometrial cancer, cervical cancer, urothelial cancer, renal cell cancer, prostate cancer, testicular tumor, Wilms' tumor, malignant melanoma, neuroblastoma, osteosarcoma, Ewing's sarcoma, and soft tissue sarcoma.

The anti-tumor agent is used for the prophylaxis and/or treatment of a cancer, and is expected to produce the reduction or disappearance of carcinoma or inhibit the growth of carcinoma down to a certain level. The "prophylaxis" used herein means the administration of the active ingredient of the present invention to a healthy subject who does not develop a disease. For example, the prophylaxis is intended to prevent the development of a disease. The "treatment" used herein means the administration of the active ingredient of the present invention to a person diagnosed with the development of a disease by a doctor (i.e. a patient). For example, the treatment is intended to alleviate a disease or symptom thereof, inhibit the growth of carcinoma, or improve the condition of a patient to the previous condition before a disease is developed. Also, even if an anti-tumor agent is administered for the purpose of preventing the worsening of a disease or symptom thereof or the growth of carcinoma, the administration is referred to as "treatment" when the subject to be administered is a patient.

The present compound has any remarkable effects for inhibiting self-renewal ability of CSCs, and thus is expected to be useful as a novel anti-tumor agent for inhibiting the persistent proliferation, metastasis, and recurrence of malignant tumors derived from CSCs.

The present compound may be formulated into a suitable dosage form and administered orally or parenterally. Examples of the dosage form include a tablet, a capsule, a powder, a granule, a solution, a suspension, an injection, a patch, and a poultice, but are not limited thereto. The preparation is formulated using pharmaceutically acceptable additive(s) according to a known method.

As appropriate, an additive such as an excipient, a disintegrant, a binder, a fluidizer, a lubricant, a coating agent, a solubilizer, a solubilizing agent, a thickening agent, a dispersant, a stabilizing agent, a sweetening agent, and a flavor may be used. Specific examples thereof include lactose, mannitol, crystalline cellulose, low substituted hydroxypropylcellulose, corn starch, partly pregelatinized starch, carmellose calcium, croscarmellose sodium, hydroxypropylcellulose, hydroxypropylmethylcellulose, polyvinylalcohol, magnesium stearate, sodium stearyl fumarate, polyethylene glycol, propylene glycol, titanium oxide, and talc.

The present compound may be used in combination with another drug(s) to enhance the therapeutic effect thereof and/or reduce side effects thereof. Specifically, the present compound can be used in combination with a drug such as a hormone therapeutic drug, a chemotherapeutic drug, an immunotherapeutic drug or a cell growth factor and a drug for inhibiting a receptor effect thereof. Hereinafter, a drug which can be used in combination with the present compound is referred to as "combined medicine".

Examples of the combined medicine include an anticancer alkylating agent, an anticancer antimetabolite, an anticancer antibiotic, a plant-based anti-cancer agent, an anticancer platinum coordination compound, an anticancer camptothecin derivative, an anticancer tyrosine kinase inhibitor, a serine-threonine kinase inhibitor, a phospholipid kinase inhibitor, a monoclonal antibody, an interferon, a biological response modifier, a hormone preparation, an immune checkpoint inhibitor, an epigenetics-related molecule inhibitor, a post-translational protein modification inhibitor, and an anti-cancer agent other than the foregoings.

The administration timing of the present compound and a combined medicine is not necessarily limited, and they may be administered simultaneously or administered with time-interval to a subject. In addition, the present compound and a combined medicine may be used in the form of a combination drug. The dosage of the combined medicine may be optionally determined based on the dosage in the clinical use. Also, the mixing ratio of the present compound and a combined medicine may be optionally determined depending on the subject to be administered, the administration route, the disease to be treated, the symptom, and a combination thereof. For example, when the subject is human, the combined medicine may be used in an amount of 0.01 to 100 parts by weight relative to 1 part by weight of the present compound. In addition, a drug (a combined medicine) such as an antiemetic, a sleep inducing agent, and an anticonvulsant may be used in combination with the present compound to inhibit side effects thereof.

The dosage can vary according to each compound and various conditions such as patient's disease, age, body weight, sex, symptom, and administration route. Typically, the present compound is administered to an adult (body weight: 50 kg) at a dose of 0.1 to 1000 mg/day, preferably at a dose of 0.1 to 300 mg/day, which may be administered once a day or 2 or 3 times a day. In addition, the present compound may be administered once in several days to several weeks.

EXAMPLES

Hereinafter, the invention is illustrated in more detail with Reference Examples, Examples, and Test Examples, but the invention should not be limited thereto. The compound names as shown in the following Reference Examples and Examples do not necessarily follow the IUPAC nomenclature system.

The following abbreviations may be used herein.
THF: tetrahydrofuran
TFA: trifluoroacetic acid
$(Boc)_2O$: di-tert-butyl dicarbonate
DMF: N,N-dimethylformamide
DIEA: N,N-diisopropylethylamine
EDCI: 1-(3-dimethylaminopropyl)-3-ethylcarbodiimide
EDCI.HCl: 1-(3-dimethylaminopropyl)-3-ethylcarbodiimide hydrochloride
HOBt: 1-hydroxybenzotriazole
$HOBt.H_2O$: 1-hydroxybenzotriazole monohydrate
Me: methyl
Et: ethyl
Ac: acetyl
Boc: tert-butoxycarbonyl
SEM: 2-(trimethylsilyl)ethoxymethyl
DMAP: N,N-dimethyl-4-aminopyridine
Rt: retention time
LC/MS analysis condition in the compound identification is as follows.
LC/MS measurement:
Detection device: ACQUITY® SQ deteceter (Waters)
HPLC: ACQUITY UPLC® system
Column: Waters ACQUITY UPLC® BEH C18 (1.7 μm, 2.1 mm×30 mm)
Solvent: A solution: 0.06% formic acid/$H_2O$, B solution: 0.06% formic acid/MeCN
Gradient condition: 0.0-1.3 min Linear gradient from B 2% to 96%
Flow rate: 0.8 mL/min
UV: 220 nm and 254 nm
The compounds of Examples 38 to 41 were identified under the following LC/MS analysis condition.
LC/MS measurement:
Detection device: detector Perkin-Elmer Sciex API 150EX Mass spectrometer (40 eV)
HPLC: Shimadzu LC 10ATVP
Column: Shiseido CAPCELL PAK C18 ACR (S-5 μm, 4.6 mm×50 mm)
Solvent: A solution: 0.035% TFA/MeCN, B solution: 0.05% TFA/$H_2O$ Gradient condition: 0.0-0.5 min A 10%, 0.5-4.8 min Linear gradient from A 10% to 99%, 4.8-5.0 min A 99%
Flow rate: 3.5 mL/min
UV: 220 nm and 254 nm Reference Example 1-1

Methyl 1-(3,4,5-trifluorobenzyl)-1H-imidazole-4-carboxylate

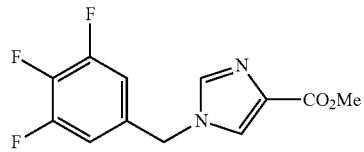 [SMILES: COC(=O)c1cn(Cc2cc(F)c(F)c(F)c2)cn1]

To a solution of methyl 4-imidazole-carboxylate (14.0 g) in acetonitrile (200 mL) were added potassium carbonate (19.9 g) and potassium iodide (0.092 g), and then 3,4,5-trifluorobenzyl bromide (14.6 mL) was added dropwise thereto at room temperature. The mixture was stirred at 70° C. for 6 hours and then cooled to room temperature, and to the reaction mixture was added water, and then the mixture was extracted with ethyl acetate. The organic layer was dried over anhydrous magnesium sulfate, filtered, and then concentrated in vacuo. The resulting crude product was washed with hexane/ethyl acetate (1/2, 60 mL) to give the title compound (14.0 g).

LC-MS ([M+H]$^+$/Rt (min)): 271.4/0.725

Reference Example 1-2

1-(3,4,5-Trifluorobenzyl)-1H-imidazole-4-carboxylic acid

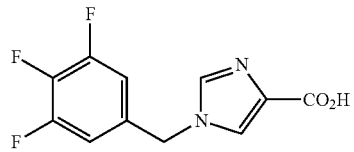 [SMILES: O=C(O)c1cn(Cc2cc(F)c(F)c(F)c2)cn1]

To a solution of the compound of Reference Example 1-1 (4.75 g) in methanol/THF (50 mL/50 mL) was added 2 mol/L aqueous sodium hydroxide solution (13.2 mL), and the mixture was stirred at 50° C. for 5 hours. The reaction mixture was concentrated in vacuo, and the residue was dissolved in water, and then aqueous hydrochloric acid solution was added thereto to adjust pH to 5. The resulting precipitate was collected on a filter, washed with water and hexane, and then dried at 50° C. in vacuo to give the title compound (4.52 g).

LC-MS ([M+H]$^+$/Rt (min)): 257.1/0.513

Reference Example 2

1-(3,4-Difluorobenzyl)-1H-imidazole-4-carboxylic acid

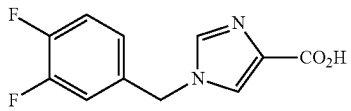

According to the processes of Reference Example 1-1 and Reference Example 1-2, the title compound was prepared from 3,4-difluorobenzyl bromide.

LC-MS ([M+H]$^+$/Rt (min)): 239.1/0.460

Reference Example 3 tert-Butyl 7-fluoro-6-({[1-(3,4,5-trifluorobenzyl)-1H-imidazol-4-yl]carbonyl}amino)-3,4-dihydroisoquinoline-2(1H)-carboxylate

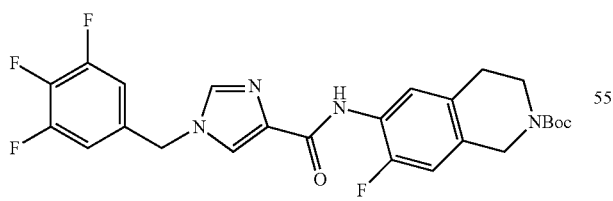

To a solution of the compound of Reference Example 1-2 (897 mg) in DMF (15 mL) were added tert-butyl 6-amino-7-fluoro-3,4-dihydroisoquinoline-2(1H)-carboxylate (932 mg), EDCI.HCl (805 mg), HOBt (567 mg) and N,N-diisopropylethylamine (1.22 mL), and the mixture was stirred at 80° C. for 7 hours. To the reaction mixture was added water and then aqueous sodium hydroxide, and the mixture was extracted with chloroform. The organic layer was washed with brine, dried over magnesium sulfate, filtered, and then concentrated in vacuo. The residue was purified by silica gel column chromatography (chloroform/methanol) to give the title compound (1.50 g).

LC-MS ([M+H]$^+$/Rt (min)): 505.3/1.137

Reference Examples 4 to 6

According to the process of Reference Example 3, the compounds of Reference Examples 4 to 6 were prepared from the corresponding starting compounds.

| Reference Example | Chemical Structural Formula | LC-MS: [M + H]$^+$/ Rt (min) |
|---|---|---|
| 4 | ![structure] | 487.6/1.084 |
| 5 | ![structure] | 487.0/1.112 |
| 6 | ![structure] | 488.3/1.006 |

Reference Example 7 tert-Butyl 6-{[(trifluoromethyl)sulfonyl]oxy}-3,4-dihydro-2,7-naphthyridine-2(1H)-carboxylate

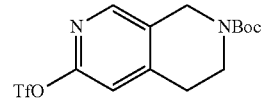

To a solution of tert-butyl 6-hydroxy-1,2,3,4-tetrahydro-2,7-naphthyridine-2-carboxylate (1.73 g) in pyridine (20 mL) was added trifluoromethanesulfonic anhydride (1.28 mL) with ice-cooling, and the mixture was stirred at room temperature for 2 hours. The reaction mixture was concentrated in vacuo, and the residue was purified by silica gel column chromatography (hexane/ethyl acetate) to give the title compound (1.72 g). LC-MS ([M+H]$^+$/Rt (min)): 383.2/1.112

Reference Example 8 tert-Butyl 6-bromo-5-fluoro-3,4-dihydroisoquino-line-2(1H)-carboxylate

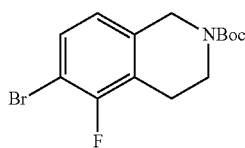 [SMILES: CC(C)(C)OC(=O)N1CCc2c(ccc(Br)c2F)C1]

To acetic acid (15 mL) was added sodium borohydride (340 mg) at room temperature. To the reaction solution was added 6-bromo-5-fluoroisoquinoline (1.0 g), and the mixture was stirred at room temperature for 15 hours. To the reaction solution was added sodium borohydride (345 mg) at room temperature for 1 hour. The reaction mixture was concentrated in vacuo, and the residue was dissolved in THF (20 mL). Di-tert-butyl dicarbonate (2.04 g) and triethylamine (3.1 mL) were added thereto, and the mixture was stirred at room temperature for 2 hours. To the reaction mixture was added water, and the mixture was extracted with ethyl acetate. The organic layer was washed with brine, dried over sodium sulfate, filtered, and then concentrated in vacuo. The residue was purified by silica gel column chromatography (hexane/ethyl acetate) to give the title compound (1.17 g).

LC-MS ([M+H]$^+$/Rt (min)): 330.2/1.213

Reference Examples 9 to 10

According to the process of Reference Example 8, the compounds of Reference Examples 9 to 10 were prepared from the corresponding starting compounds.

| Reference Example | Chemical Structural Formula | LC-MS: [M + H]$^+$/ Rt (min) |
|---|---|---|
| 9 | 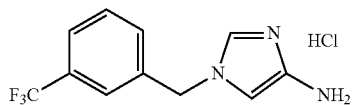 | 330.1/1.244 |
| 10 | 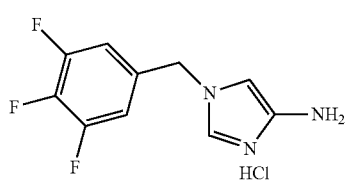 | 330.4/1.217 |

Reference Example 11-1

4-Nitro-1-[3-(trifluoromethyl)benzyl]-1H-imidazole

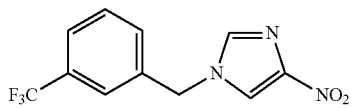

4-Nitro-1H-imidazole (35.8 g), 3-trifluoromethylbenzyl bromide (75.7 g), potassium iodide (0.131 g), potassium carbonate (48.1 g) and acetonitrile (270 mL) were mixed, and the mixture was stirred at 80° C. for 5 hours. To the reaction mixture was added water, and the mixture was extracted with ethyl acetate. The organic layer was washed with brine, dried over magnesium sulfate, filtered, and then concentrated in vacuo. To the resulting solid was added diisopropyl ether (300 mL), and the mixture was stirred at room temperature for 1 hour. The resulting precipitate was collected on a filter, washed with diisopropyl ether, and then dried at 50° C. in vacuo to give the title compound (69.0 g).

LC-MS ([M+H]$^+$/Rt (min)): 272.1/0.835

Reference Example 11-2

1-[3-(Trifluoromethyl)benzyl]-1H-imidazole-4-amine hydrochloride

To a solution of the compound of Reference Example 11-1 (34.0 g) in ethyl acetate (330 mL) was added rhodium-activated carbon (5%, 17.0 g), and the mixture was stirred under hydrogen atmosphere at room temperature for 14 hours.

The reaction mixture was filtered through Celite®, washed with ethyl acetate (50 mL×4), and then to the filtrate was added hydrogen chloride (4 mol/L in ethyl acetate, 38.0 mL). The filtrate was concentrated in vacuo, and then to the resulting crude product were added ethyl acetate (200 mL) and hexane (200 mL), and the mixture was stirred at room temperature for 10 minutes. The resulting precipitate was collected on a filter and washed with hexane/ethyl acetate (1/1, 20 mL×3), and then the resulting solid was dried at 40° C. in vacuo to give the title compound (31.4 g).

LC-MS ([M+H]$^+$/Rt (min)): 242.1/0.548

Reference Example 12

1-(3,4,5-Trifluorobenzyl)-1H-imidazole-4-amine hydrochloride

According to the processes of Reference Examples 11-1 and 11-2, the title compound was prepared from 3,4,5-trifluorobenzyl bromide.

LC-MS ([M+H]$^+$/Rt (min)): 228.1/0.473

Reference Example 13-1 tert-Butyl 6-cyano-8-fluoro-3,4-dihydroisoquino-line-2(1H)-carboxylate

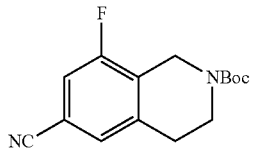 [SMILES: CC(C)(C)OC(=O)N1CCc2cc(Br)cc(F)c2C1]

To a solution of the compound of Reference Example 9 (124 mg) in DMF (1 mL) were added tetrakis(triphenylphosphine)palladium (45 mg) and zinc cyanide (57 mg), and the mixture was stirred at 120° C. for 8 hours. The reaction mixture was concentrated in vacuo, and then the residue was purified by silica gel column chromatography (hexane/ethyl acetate) to give the title compound (48 mg).
LC-MS ([M+H]$^+$/Rt (min)): 277.2/1.048

Reference Example 13-2-1

2-(tert-Butoxycarbonyl)-8-fluoro-1,2,3,4-tetrahydroisoquinoline-6-carboxylic acid

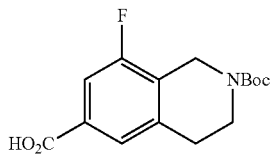

To a solution of the compound of Reference Example 13-1 (2.13 g) in 2-propanol (40 mL) were added water (10 mL) and sodium hydroxide (5 g), and the mixture was stirred at 110° C. for 11 hours. The reaction mixture was concentrated in vacuo, and the residue was extracted with saturated aqueous sodium bicarbonate solution. The aqueous layer was acidified with sodium hydrogen sulfate and extracted with chloroform. The resulting organic layer was dried over sodium sulfate and concentrated in vacuo to give the title compound (2.54 g).
LC-MS ([M+H]$^+$/Rt (min)): 296.2/0.907

Reference Examples 13-2-2 to 13-2-4

According to the processes of Reference Example 13-1 and 13-2-1, the compounds of Reference Example 13-2-2 to 13-2-4 were prepared from the corresponding starting compounds.

| Reference Example | Chemical Structural Formula | LC-MS: [M + H]$^+$/ Rt (min) |
|---|---|---|
| 13-2-2 | | 296.2/0.867 |
| 13-2-3 | | 296.1/0.864 |
| 13-2-4 | | 279.0/0.537 |

Reference Example 13-3 tert-Butyl 8-fluoro-6-{[1-(3,4,5-trifluorobenzyl)-1H-imidazol-4-yl]carbamoyl}-3,4-dihydroisoquinoline-2(1H)-carboxylate

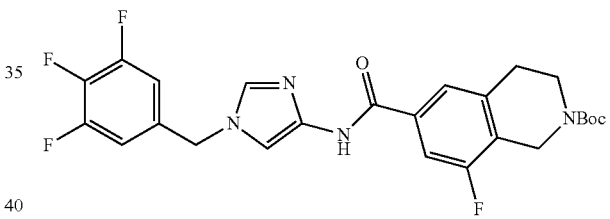

According to the process of Reference Example 3, the title compound was prepared from the compounds of Reference Example 13-2-1 and Reference Example 12.
LC-MS ([M+H]$^+$/Rt (min)): 505.3/1.084

Reference Examples 14 to 31

According to the process of Reference Example 3, the compounds of Reference Examples 14 to 31 were prepared from the corresponding starting compounds.

| Reference Example | Chemical Structural Formula | LC-MS: [M + H]$^+$/ Rt (min) |
|---|---|---|
| 14 | | 505.3/1.076 |

-continued

| Reference Example | Chemical Structural Formula | LC-MS: [M + H]⁺/ Rt (min) |
|---|---|---|
| 15 | 3,4,5-trifluorobenzyl-imidazole-carboxamide-tetrahydronaphthyridine-NBoc | 488.3/1.019 |
| 16 | 3-(trifluoromethyl)benzyl-imidazole-carboxamide-tetrahydronaphthyridine-NBoc | 501.9/1.048 |
| 17 | 3-(trifluoromethyl)benzyl-imidazole-carboxamide-tetrahydronaphthyridine-NBoc | 502.0/1.033 |
| 18 | 3,4,5-trifluorobenzyl-imidazole-carboxamide-tetrahydronaphthyridine-NBoc | 488.0/1.012 |
| 19 | 3,4,5-trifluorobenzyl-imidazole-carboxamide-tetrahydronaphthyridine-NBoc | 488.3/0.955 |
| 20 | 3-(trifluoromethyl)benzyl-imidazole-carboxamide-tetrahydronaphthyridine-NBoc | 502.2/0.951 |
| 21 | 3,4,5-trifluorobenzyl-imidazole-carboxamide-fluoro-tetrahydroisoquinoline-NBoc | 505.3/1.071 |
| 22 | 3-(trifluoromethyl)benzyl-imidazole-carboxamide-fluoro-tetrahydroisoquinoline-NBoc | 519.3/1.098 |
| 23 | 3-(trifluoromethyl)benzyl-imidazole-carboxamide-tetrahydroisoquinoline-NBoc | 502.3/1.042 |
| 24 | 3-(trifluoromethyl)benzyl-imidazole-carboxamide-tetrahydroisoquinoline-NBoc | 502.3/1.031 |

| Reference Example | Chemical Structural Formula | LC-MS: [M + H]+/ Rt (min) |
|---|---|---|
| 25 | | 507.9/1.077 |
| 26 | | 515.3/1.149 |
| 27 | | 515.3/0.966 |
| 28 | | 487.4/1.014 |
| 29 | | 501.4/1.070 |
| 30 | | 487.3/1.023 |
| 31 | | 529.6/1.147 |

Reference Example 32-1

Methyl 5-[(tert-butoxycarbonyl)amino]-6-chloro-nicotinate

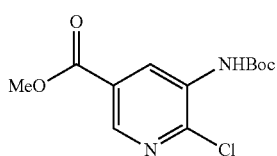 [SMILES: COC(=O)c1cnc(Cl)c(NC(=O)OC(C)(C)C)c1]

To a solution of methyl 5-amino-6-chloro-nicotinate (325 mg) in THF (10 mL) were added di-tert-butyl dicarbonate (760 mg) and DMAP (11 mg), and the mixture was stirred at room temperature for 15.5 hours. Additionally, di-tert-butyl dicarbonate (38 mg) was added thereto, and the mixture was stirred at 60° C. for 45 minutes. The mixture was cooled to room temperature, and the solvent therein was removed. To the residue were added methanol (5 mL) and potassium carbonate (481 mg), and the mixture was stirred at room temperature for 2.5 hours. Saturated aqueous ammonium chloride solution was added thereto, and the mixture was extracted with ethyl acetate. The organic layer was washed with brine, dried over anhydrous sodium sulfate, filtered, and then concentrated in vacuo. The residue was purified by silica gel column chromatography (hexane/ethyl acetate) to give the title compound (321 mg).

LC-MS ([M+H]+/Rt (min)): 287.1/0.985

Reference Example 32-2

Methyl 5-[(tert-butoxycarbonyl)amino]-6-ethenyl-nicotinate

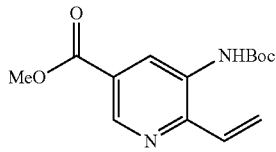

To a solution of the compound of Reference Example 32-1 (321 mg) in a mixture of 1,2-dimethoxyethane (9 mL)/water (0.9 mL) were added pinacol vinylboronate (0.575 mL), tetrakis(triphenylphosphine)palladium (129 mg) and potassium carbonate (465 mg), and the mixture was stirred under microwave irradiation at 120° C. for 1 hour. The mixture was cooled to room temperature, and to the reaction mixture was added water, and then the mixture was extracted with ethyl acetate. The organic layer was washed with brine, dried over sodium sulfate, filtered, and then concentrated. The residue was purified by silica gel column chromatography (hexane/ethyl acetate) to give the title compound (207 mg).

LC-MS ([M+H]$^+$/Rt (min)): 279.5/0.885

Reference Example 32-3

Methyl 5-[(tert-butoxycarbonyl)amino]-6-formyl-nicotinate

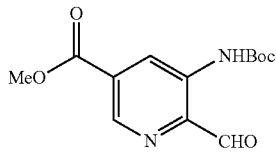 [SMILES: COC(=O)c1cnc(C=O)c(NC(=O)OC(C)(C)C)c1]

To a solution of the compound of Reference Example 32-2 (207 mg) in a mixture of acetone (8 mL)/water (4 mL) were added sodium periodate (659 mg) and osmium tetraoxide (2.5 wt % in tert-butanol, 0.71 mL), and the mixture was stirred at room temperature for 3 hours. To the reaction mixture were added saturated aqueous sodium thiosulfate solution and water, and the mixture was extracted with ethyl acetate. The organic layer was washed with brine, dried over sodium sulfate, filtered, and then concentrated in vacuo. The residue was purified by silica gel column chromatography (hexane/ethyl acetate) to give the title compound (110 mg).

LC-MS ([M+H]$^+$/Rt (min)): 281.2/1.037

Reference Example 32-4

Methyl 5-[(tert-butoxycarbonyl)amino]-6-(hydroxymethyl)-nicotinate

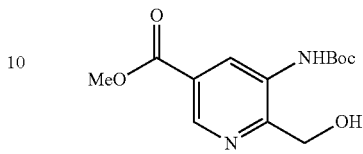

To a solution of the compound of Reference Example 32-3 (110 mg) in methanol was added sodium borohydride, and the mixture was stirred at room temperature for 1 hour. To the reaction mixture were added saturated aqueous ammonium chloride solution and water, and the mixture was extracted with ethyl acetate. The organic layer was washed with brine, dried over sodium sulfate, filtered, and then concentrated in vacuo to give the title compound (111 mg).

LC-MS ([M+H]$^+$/Rt (min)): 282.8/0.761

Reference Example 32-5

2-Oxo-1,4-dihydro-2H-pyrido[3,2-d][1,3]oxazine-7-carboxylic acid

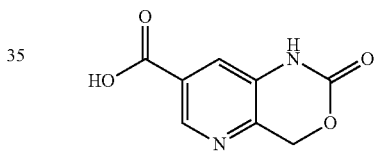

To a solution of the compound of Reference Example 32-4 (111 mg) in THF (2 mL)/methanol (4 mL) was added 2 mol/L aqueous sodium hydroxide solution (0.39 mL), and the mixture was stirred at room temperature for 16 hours. To the reaction mixture was added 2 mol/L hydrochloric acid (0.25 mL) to adjust pH to 7. The reaction mixture was concentrated in vacuo to give the title compound (76 mg).

LC-MS ([M+H]$^+$/Rt (min)): 195.1/0.325

Reference Example 33

According to the process of Reference Example 3, the compound of Reference Example 33 was prepared from the corresponding starting compound.

| Reference Example | Chemical Structural Formula | LC-MS: [M + H]$^+$/ Rt (min) |
|---|---|---|
| 33 | ![structure] | 470.3/0.976 |

Reference Example 34

According to the process of Reference Example 11-1, the compound of Reference Example 34 was prepared from the corresponding starting compound.

| Reference Example | Chemical Structural Formula | LC-MS: [M + H]+/ Rt (min) |
|---|---|---|
| 34 | 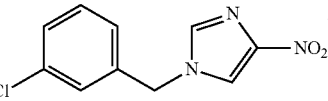 | 238.1/0.776 |

Reference Example 35

According to the process of Reference Example 11-2, the compound of Reference Example 35 was prepared from the compound of Reference Example 34.

| Reference Example | Chemical Structural Formula | LC-MS: [M + H]+/ Rt (min) |
|---|---|---|
| 35 | 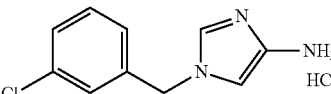 | 208.1/0.460 |

Reference Examples 36 to 38

According to the process of Reference Example 3, the compounds of Reference Examples 36 to 38 were prepared from the compound of Reference Example 35 and the corresponding starting compounds.

| Reference Example | Chemical Structural Formula | LC-MS: [M + H]+/ Rt (min) |
|---|---|---|
| 36 | 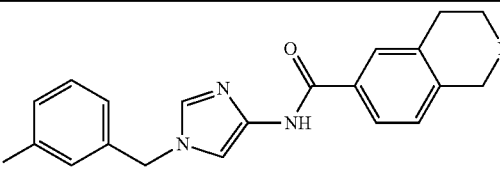 | 467.4/1.033 |
| 37 | 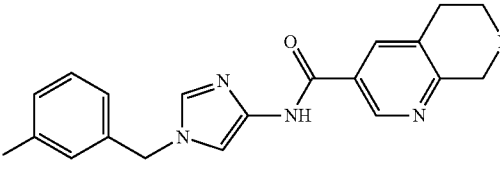 | 468.4/0.940 |
| 38 | 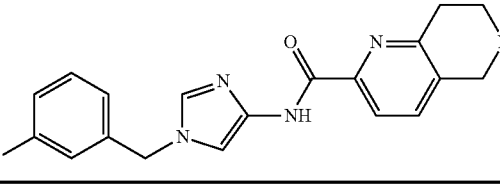 | 468.4/1.020 |

Reference Example 39-1

3-Aminopyridine-4-carboaldehyde

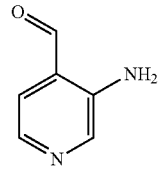

A solution of (3-aminopyridin-4-yl)-methanol (10.4 g) and manganese dioxide (50.3 g) in chloroform (100 mL) was stirred at room temperature for 18 hours. The reaction solution was filtered through Celite and concentrated to give the title compound (10.1 g).

LC-MS ([M+H]+/Rt (min)): 123.0/0.218

Reference Example 39-2

Ethyl 1,7-naphthyridine-3-carboxylate hydrochloride

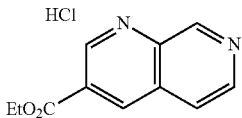

To a solution of the compound of Reference Example 39-1 (10.1 g) and ethyl 3-ethoxyacrylate (13.8 mL) in chloroform (100 mL) was added TFA (63.9 mL) with ice-cooling, and the mixture was stirred for 1 hour with heating under reflux. The reaction solution was concentrated, and the residue was dissolved in ethyl acetate, washed with saturated aqueous sodium bicarbonate solution and brine, dried over anhydrous sodium sulfate, filtered, and then concentrated in vacuo. The resulting crude product was dissolved in ethyl acetate (350 mL), and then 4 mol/L hydrochloric acid-ethyl acetate solution (42 mL) was added thereto, and the mixture was stirred for 1 hour. The resulting solid was filtered to give the title compound (16.8 g).

LC-MS ([M+H]$^+$/Rt (min)): 203.1/0.619

Reference Example 39-3

Ethyl 7,8-dihydro-1,7-naphthyridine-3-carboxylate

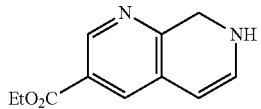

To a solution of the compound of Reference Example 39-2 (3.13 g) in methanol (60 mL) was added sodium borohydride (1.49 g) with ice-cooling, and the mixture was stirred at room temperature for 30 minutes. Additionally, to the reaction solution was added sodium borohydride (0.8 g) with ice-cooling, and the mixture was stirred for 30 minutes. The reaction solution was concentrated, and then the residue was dissolved in ethyl acetate, washed with brine, dried over anhydrous sodium sulfate, filtered, and concentrated to give the title compound (2.68 g).

LC-MS ([M+H]$^+$/Rt (min)): 205.1/0.420

Reference Example 39-4

7-tert-Butyl 3-ethyl 5,8-dihydro-1,7-naphthyridine-3,7(6H)-dicarboxylate

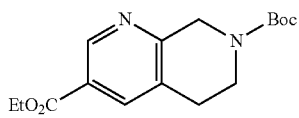

A solution of the compound of Reference Example 39-3 (2.68 g), Boc$_2$O (12.6 g) and palladium/carbon (1.6 g) in THF (100 mL) was stirred under hydrogen atmosphere at room temperature for 18 hours. The reaction solution was filtered through Celite® and concentrated. The resulting residue was purified by silica gel column chromatography to give the title compound (1.51 g).

LC-MS ([M+H]$^+$/Rt (min)): 307.47/0.967

Reference Example 39-5

Sodium 7-(tert-butoxycarbonyl)-5,6,7,8-tetrahydro-1,7-naphthyridine-3-carboxylate

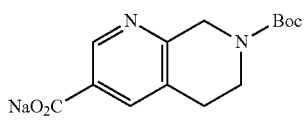

To a solution of the compound of Reference Example 39-4 (1.51 g) in THF (20 mL) were added water (5 mL) and 5 mol/L aqueous sodium hydroxide solution (1.5 mL) with ice-cooling, and the mixture was stirred at room temperature for 7 hours. The reaction solution was washed with diethyl ether, and then the aqueous phase was concentrated to give the title compound (1.51 g).

LC-MS ([M+H]$^+$/Rt (min)): 279.2/0.707

Reference Example 40-1

4-Nitro-1-{[2-(trimethylsilyl)ethoxy]methyl}-1H-imidazole

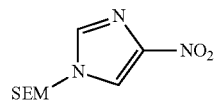 [SMILES: C[Si](C)(C)CCOCn1cnc([N+](=O)[O-])c1]

A solution of 4-nitroimidazole in DMF (50 mL) was added dropwise to a solution of sodium hydride (10.3 g) in DMF (50 mL) with ice-cooling, and the mixture was stirred with ice-cooling for 30 minutes. 2-(Trimethylsilyl)ethoxymethyl chloride (17.5 mL) was added dropwise thereto with ice-cooling, and the mixture was stirred at room temperature for 1 hour. To the reaction solution were added methanol (30 mL) and ice, and the aqueous layer was extracted with hexane/ethyl acetate=1/1. The organic phase was dried over anhydrous magnesium sulfate, filtered, and then concentrated in vacuo. The resulting crude product was purified by silica gel column chromatography (hexane/ethyl acetate) to give the title compound (19.4 g).

LC-MS ([M+H]$^+$/Rt (min)): 244.1/0.929

Reference Example 40-2 tert-Butyl 6-[(1-{([2-(trimethylsilyl)ethoxy]methyl}-1H-imidazol-4-yl)carbamoyl]-3,4-dihydroisoquinoline-2(1H)-carboxylate

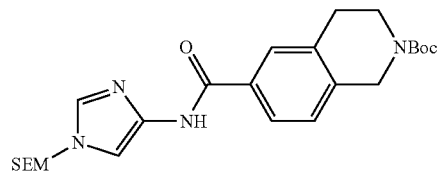 [SMILES: CC(C)(C)OC(=O)N1CCc2cc(C(=O)Nc3cn(COCC[Si](C)(C)C)cn3)ccc2C1]

A solution of the compound of Reference Example 40-1 (3.01 g) and palladium/carbon (1.57 g) in ethyl acetate (30 mL) was stirred under hydrogen atmosphere at room temperature for 6 hours. The reaction solution was filtered through Celite®. To the resulting filtrate were added WSC (2.48 g), 2-(tert-butoxycarbonyl)-1,2,3,4-tetrahydroisoquinoline-6-carboxylic acid (2.29 g) and DIEA (4.33 mL), and the mixture was stirred at room temperature for 18 hours. The reaction solution was washed with saturated aqueous sodium bicarbonate solution and brine, dried over sodium hydrogen sulfate, filtered, and then concentrated. The resulting residue was purified by silica gel column chromatography (hexane/ethyl acetate) to give the title compound (2.95 g).

LC-MS ([M+H]$^+$/Rt (min)): 473.4/1.106

Reference Example 40-3 tert-Butyl 6-{[1-(tert-butoxycarbonyl)-1H-imidazol-4-yl]carbamoyl}-3,4-dihydroisoquinoline-2(1H)-carboxylate

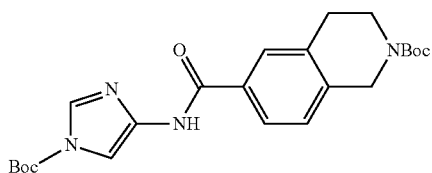 [SMILES: CC(C)(C)OC(=O)N1CCc2cc(C(=O)Nc3cn(C(=O)OC(C)(C)C)cn3)ccc2C1]

A solution of the compound of Reference Example 40-2 (1.08 g) in 4 mol/L dioxane hydrochloride (50 mL) was stirred for 8 hours with heating under reflux. The reaction solution was concentrated, and then to a solution of the resulting residue in tetrahydrofuran (50 mL) were added (Boc)$_2$O (2.11 g) and triethylamine (1.6 mL), and the mixture was stirred at room temperature for 24 hours. The reaction solution was concentrated, and then the resulting crude product was purified by silica gel column chromatography (hexane/ethyl acetate) to give the title compound (0.35 g).
LC-MS ([M+H]$^+$/Rt (min)): 443.4/1.085

Reference Example 40-4 tert-Butyl 6-(1H-imidazol-4-ylcarbamoyl)-3,4-dihydroisoquinoline-2(1H)-carboxylate

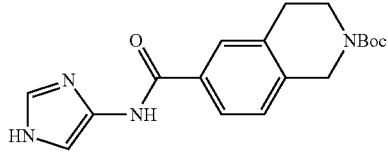 [SMILES: CC(C)(C)OC(=O)N1CCc2cc(C(=O)Nc3c[nH]cn3)ccc2C1]

To a solution of the compound of Reference Example 40-3 (0.35 g) in tetrahydrofuran (10 mL) was added 5 mol/L aqueous sodium hydroxide solution (0.5 mL) with ice-cooling, and the mixture was stirred at room temperature for 24 hours. The reaction solution was concentrated, and then the resulting residue was dissolved in ethyl acetate and washed with water and brine. The resulting organic phase was dried over anhydrous magnesium sulfate, filtered, and then concentrated in vacuo to give the title compound (0.26 g).
LC-MS ([M+H]$^+$/Rt (min)): 343.2/0.697

Reference Example 40-5 tert-Butyl 6-[(1-benzyl-1H-imidazol-4-yl)carbamoyl]-3,4-dihydroisoquinoline-2(1H)-carboxylate

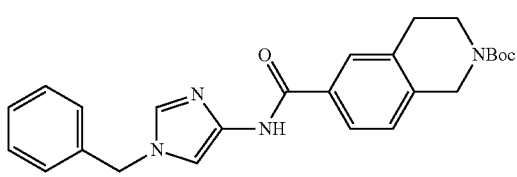 [SMILES: CC(C)(C)OC(=O)N1CCc2cc(C(=O)Nc3cn(Cc4ccccc4)cn3)ccc2C1]

To a solution of the compound of Reference Example 40-4 (0.07 g) in DMF (1 mL) were added sodium carbonate (0.03 g) and benzyl bromide (0.04 g), and the mixture was stirred at 100° C. for 4 hours. The reaction solution was concentrated, and then the resulting crude product was purified by silica gel column chromatography (hexane/ethyl acetate) to give the title compound (0.03 g).
LC-MS ([M+H]$^+$/Rt (min)): 433.4/0.903

Reference Examples 41 to 62

According to the process of Reference Example 40-5, the compounds of Reference Examples 41 to 62 were prepared from the compound of Reference Example 40-4 and the corresponding starting compounds.

| Reference Example | Q$^1$—W$^1$— | LC-MS: [M + H]$^+$/ Rt (min) |
|---|---|---|
| 41 | 2-F-benzyl | 451.3/0.981 |
| 42 | 3,4-diF-benzyl | 469.4/1.014 |
| 43 | 3,5-diF-benzyl | 469.4/1.019 |
| 44 | 4-F$_3$CO-benzyl | 517.4/1.096 |
| 45 | 2-Me-benzyl | 447.3/1.020 |
| 46 | 3-F-benzyl | 451.3/0.988 |
| 47 | 3-MeO-benzyl | 463.3/1.001 |
| 48 | 4-F-benzyl | 451.3/1.013 |

| Reference Example | Q¹—W¹— | LC-MS: [M + H]⁺/ Rt (min) |
|---|---|---|
| 49 | 3-methylbenzyl | 447.3/1.057 |
| 50 | 4-methylbenzyl | 447.1/1.093 |
| 51 | 2-(trifluoromethyl)benzyl | 501.4/1.128 |
| 52 | 4-(trifluoromethyl)benzyl | 501.4/1.139 |
| 53 | 4-methoxybenzyl | 463.4/1.019 |
| 54 | cyclohexylmethyl | 439.4/0.960 |
| 55 | 2-cyclohexylethyl | 453.4/1.021 |
| 56 | 4-chlorobenzyl | 467.3/1.006 |
| 57 | 3-cyanobenzyl | 458.3/0.896 |
| 58 | 3-phenoxybenzyl | 525.4/1.094 |
| 59 | 4-chloro-3-fluorobenzyl | 485.3/1.028 |
| 60 | 3-chloro-5-fluorobenzyl | 485.3/1.040 |
| 61 | 4-fluoro-3-(trifluoromethyl)benzyl | 519.3/1.049 |
| 62 | 4-chloro-3-(trifluoromethyl)benzyl | 535.3/1.200 |

Reference Example 63-1 tert-Butyl 3-[(1-{[2-(trimethylsilyl)ethoxy]methyl}-1H-imidazol-4-yl)carbamoyl]-5,8-dihydro-1,7-naphthyridine-7(6H)-carboxylate According to the process of Reference Example 40-2, the title compound was prepared from the compounds of Reference Examples 39-5 and 40-1.

LC-MS ([M+H]⁺/Rt (min)): 474.4/1.012

Reference Example 63-2 tert-Butyl 3-{[1-(tert-butoxycarbonyl)-1H-imidazol-4-yl]carbamoyl}-5,8-dihydro-1,7-naphthyridine-7(6H)-carboxylate According to the process of Reference Example 40-3, the title compound was prepared from the compound of Reference Example 63-1.

Reference Example 63-3 tert-Butyl 3-(1H-imidazol-4-ylcarbamoyl)-5,8-dihydro-1,7-naphthyridine-7(6H)-carboxylate

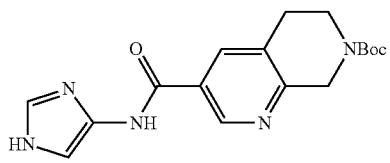

According to the process of Reference Example 40-4, the title compound was prepared from the compound of Reference Example 63-2.

LC-MS ([M+H]$^+$/Rt (min)): 344.2/0.572

Reference Examples 64 to 88

According to the process of Reference Example 40-5, the compounds of Reference Examples 64 to 88 were prepared from the compound of Reference Example 63-3 and the corresponding starting compounds.

| Reference Example | Q¹—W¹— | LC-MS: [M + H]⁺/ Rt (min) |
|---|---|---|
| 64 | 2-F-C₆H₄-CH₂- | 452.4/0.851 |
| 65 | 2,4-diF-C₆H₃-CH₂- | 470.3/0.890 |
| 66 | 3,4-diF-C₆H₃-CH₂- | 470.3/0.897 |
| 67 | 3-F₃CO-C₆H₄-CH₂- | 518.3/0.987 |
| 68 | 3-PhO-C₆H₄-CH₂- | 526.4/1.038 |
| 69 | 4-Cl-3-F-C₆H₃-CH₂- | 486.3/0.951 |
| 70 | 3-Cl-5-F-C₆H₃-CH₂- | 466.3/0.953 |
| 71 | 3-F₃C-4-F-C₆H₃-CH₂- | 520.3/0.971 |
| 72 | 4-Cl-3-F₃C-C₆H₃-CH₂- | 536.3/1.022 |
| 73 | cyclohexyl-CH₂- | 440.4/0.931 |
| 74 | cyclohexyl-CH₂CH₂- | 454.4/1.010 |
| 75 | pyridin-3-yl-CH₂- | 435.4/0.635 |
| 76 | 3-MeO-C₆H₄-CH₂- | 464.3/0.863 |
| 77 | C₆H₅-CH₂- | 434.3/0.850 |
| 78 | 2-Me-C₆H₄-CH₂- | 448.3/0.895 |
| 79 | 4-F-C₆H₄-CH₂- | 452.4/0.866 |

-continued

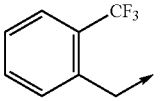

| Reference Example | Q¹—W¹— | LC-MS: [M + H]⁺/ Rt (min) |
|---|---|---|
| 80 | 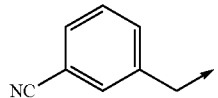 | 502.3/0.960 |
| 81 | 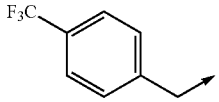 | 459.3/0.819 |
| 82 | 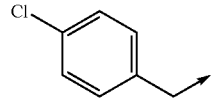 | 502.3/0.969 |
| 83 | 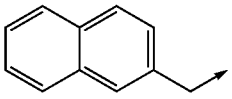 | 468.3/0.933 |
| 84 | 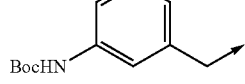 | 484.4./0.966 |
| 85 | 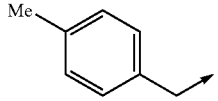 | 549.4/0.951 |
| 86 | 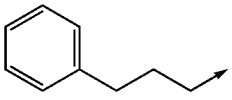 | 448.3/0.909 |
| 87 | 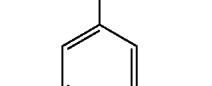 | 462.4./0.906 |
| 88 | 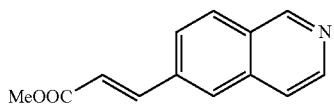 | 552.3/1.067 |

Reference Example 89-1

Methyl (2E)-3-(isoquinolin-6-yl)prop-2-enoate

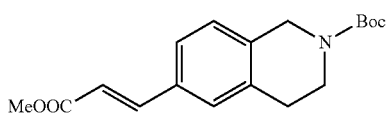 [SMILES: COC(=O)/C=C/c1ccc2c(c1)CCN(C(=O)OC(C)(C)C)C2]

To a solution of 6-(4,4,5,5-tetramethyl-1,3,2-dioxaborolan-2-yl)isoquinoline (0.98 g) in DMF (10 mL) were added palladium acetate (0.09 g), copper acetate (1.40 g), lithium acetate dihydrate (0.78 g) and methyl acrylate (334 µL), and the mixture was stirred at 100° C. for 4 hours. The reaction solution was concentrated, and the residue was purified by silica gel column chromatography (hexane/ethyl acetate) to give the title compound (0.46 g).

LC-MS ([M+H]⁺/Rt (min)): 214.1/0.475

Reference Example 89-2 tert-Butyl 6-[(1E)-3-methoxy-3-oxoprop-1-en-1-yl]-3,4-dihydroisoquinoline-2(1H)-carboxylate

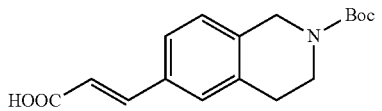 [SMILES: CC(C)(C)OC(=O)N1CCc2cc(/C=C/C(=O)O)ccc2C1]

To a solution of the compound of Reference Example 89-1 (0.46 g) in acetic acid (1 mL) was added sodium borohydride (0.10 g), and the mixture was stirred at room temperature for 30 minutes. The reaction solution was basified with saturated aqueous sodium hydrogen carbonate solution, THF (10 mL) and Boc₂O (0.49 g) were added thereto, and then the mixture was stirred at room temperature for 16 hours. The reaction solution was diluted with ethyl acetate, washed with water and brine, dried over anhydrous sodium sulfate, filtered, and then concentrated. The residue was purified by silica gel column chromatography (hexane/ethyl acetate) to give the title compound (0.03 g).

LC-MS ([M+H]⁺/Rt (min)): 318.2/1.103

Reference Example 89-3

(2E)-3-[2-(tert-Butoxycarbonyl)-1,2,3,4-tetrahydroisoquinolin-6-yl]prop-2-enoic acid To a solution of the compound of Reference Example 89-2 (0.03 g) in THF (4 mL) and water (1 mL) was added lithium hydroxide (0.01 g) with ice-cooling, and the mixture was stirred at room temperature for 13 hours. The reaction solution was diluted with saturated aqueous sodium hydrogen carbonate solution and washed with diethyl ether. The resulting aqueous phase was acidified with sodium hydrogen sulfate and then extracted with chloroform. The organic layer was dried over anhydrous sodium sulfate and then concentrated to give the title compound (0.03 g).

LC-MS ([M−H]⁻/Rt (min)): 302.5/0.916

Reference Example 89-4 tert-Butyl 6-[(1E)-3-oxo-3-{[1-(3,4,5-trifluorobenzyl)-1H-imidazol-4-yl]amino}prop-1-en-1-yl]-3,4-dihydroisoquinoline-2(1H)-carboxylate

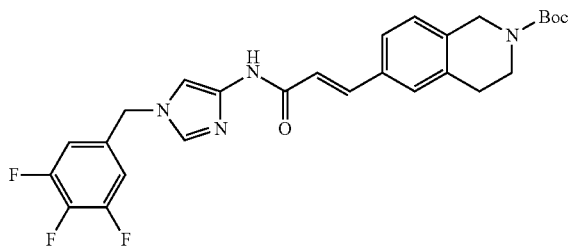 [SMILES: CC(C)(C)OC(=O)N1CCc2cc(/C=C/C(=O)Nc3cn(Cc4cc(F)c(F)c(F)c4)cn3)ccc2C1]

According to the process of Reference Example 3, the title compound was prepared from the corresponding starting compound.

LC-MS ([M+H]⁺/Rt (min)): 513.0/1.084

Reference Examples 90 to 98

According to the process of Reference Example 40-5, the compounds of Reference Examples 90 to 98 were prepared from the compound of Reference Example 63-3 and the corresponding starting compounds.

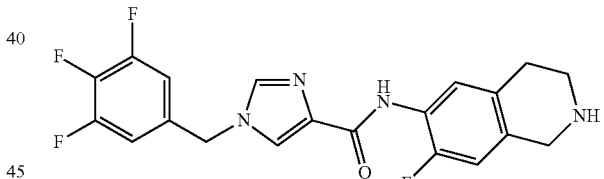

| Reference Example | Q¹—W¹— | LC-MS: [M + H]⁺/Rt (min) |
|---|---|---|
| 90 | EtO₂C-phenyl-CH₂- | 493.3/0.879 |
| 91 | MeO₂S-phenyl-CH₂- | 512.3/0.779 |
| 92 | phenyl-(CH₂)₃- | 477.4/1.031 |
| 93 | phenyl-O-CH₂-CH₂- | 465.4/0.902 |
| 94 | phenyl-O-(CH₂)₃- | 479.3/0.934 |
| 95 | tetrahydropyran-4-yl-CH₂- | 442.4/0.858 |
| 96 | benzo[1,3]dioxol-5-yl-CH₂- | 479.3/0.867 |
| 97 | 3-F-phenyl-CH₂- | 453.3/1.060 |
| 98 | 3-Me-phenyl-CH₂- | 448.4/1.200 |

Example 1

N-(7-Fluoro-1,2,3,4-tetrahydroisoquinolin-6-yl)-1-(3,4,5-trifluorobenzyl)-1H-imidazole-4-carboxamide To a solution of the compound of Reference Example 3 (1.5 g) in methanol (40 mL) was added 4 mol/L dioxane hydrochloride (2.97 mL), and the mixture was stirred at room temperature overnight. The reaction mixture was concentrated in vacuo, and then water and 2 mol/L aqueous sodium hydroxide solution were added thereto. The resulting precipitate was collected on a filter, washed with water and hexane/ethyl acetate (2/1), and dried in vacuo to give the title compound (0.89 g).

LC-MS ([M+H]⁺/Rt (min)): 405.2/0.665

¹H-NMR (400 MHz, DMSO-d₆): δ 9.27 (1H, s), 7.96-7.93 (2H, m), 7.69 (1H, d, J=8.0 Hz), 7.43-7.34 (2H, m), 6.91 (1H, d, J=11.6 Hz), 5.23 (2H, s), 3.75 (2H, s), 2.90-2.86 (2H, m), 2.62-2.57 (2H, m).

Examples 2 to 3

According to the process of Example 1, the compounds of Examples 2 to 3 were prepared from the corresponding compounds of each Reference Example.

| Example | Chemical Structural Formula | Instrumental Analysis Data |
|---|---|---|
| 2 | | $^1$H-NMR (400 MHz, DMSO-$d_6$): 9.28 (1H, s), 7.96-7.93 (2H, m), 7.71 (1H, d, J = 7.6 Hz), 7.53-7.42 (2H, m), 7.22-7.18 (1H, m), 6.93 (1H, d, J = 10.8 Hz), 5.24 (2H, s), 3.78 (2H, s), 2.93-2.89 (2H, m), 2.65-2.59 (2H, m). LC-MS: [M + H]$^+$/Rt (min): 387.0/0.660 |
| 3 | | $^1$H-NMR (400 MHz, DMSO-$d_6$): 9.30 (1H, s), 8.02 (1H, s), 7.97 (1H, s), 7.96 (1H, s), 7.88 (1H, s), 7.43-7.37 (2H, m), 5.23 (2H, s), 3.78 (2H, s), 2.92-2.88 (2H, m), 2.71-2.66 (2H, m). LC-MS: [M + H]$^+$/Rt (min): 388.2/0.601 |

Example 4

N-(1,2,3,4-Tetrahydroisoquinolin-6-yl)-1-(3,4,5-trifluorobenzyl)-1H-imidazole-4-carboxamide dihydrochloride

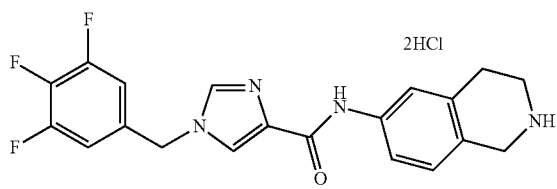 [SMILES: O=C(Nc1ccc2c(c1)CCNC2)c1cn(Cc2cc(F)c(F)c(F)c2)cn1]

To a solution of the compound of Reference Example 4 (75 mg) in methanol (5 mL) was 4 mol/L dioxane hydrochloride (0.12 mL), and the mixture was stirred at 80° C. The resulting precipitate was collected on a filter, washed with diisopropyl ether, and then dried in vacuo to give the title compound (35.8 mg).

LC-MS ([M+H]$^-$/Rt (min)): 387.2/0.615

Examples 5 to 15

According to the process of Example 4, the compounds of Examples 5 to 15 were prepared from the corresponding compounds of each Reference Example.

| Example | Chemical Structural Formula | Instrumental Analysis Data |
|---|---|---|
| 5 | | $^1$H-NMR (400 MHz, CD$_3$OD): 8.94 (1H, d, J = 1.6 Hz), 7.78 (1H, s), 7.65 (1H, d, J = 9.2 Hz), 7.58 (1H, d, J = 2.0 Hz), 7.33-7.30 (2H, m), 5.44 (2H, s), 4.46 (2H, s), 3.56 (2H, t, J = 6.4 Hz), 3.24 (2H, t, J = 6.0 Hz). LC-MS ([M + H]$^+$/Rt (min)): 405.2/0.645 |
| 6 | | $^1$H-NMR (400 MHz, CD$_3$OD): 8.89 (1H, d, J = 2.0 Hz), 7.87 (2H, m), 7.55 (1H, d, J = 2.0 Hz), 7.42 (1H, d, J = 8.4 Hz), 7.33-7.27 (2H, m), 5.43 (2H, s), 4.46 (2H, s), 3.56 (2H, t, J = 6.4 Hz), 3.22 (2H, t, J = 6.4 Hz). LC-MS ([M + H]$^+$/Rt (min)): 387.2/0.635 |
| 7 | | $^1$H-NMR (400 MHz, CD$_3$OD): 7.77 (1H, d, J = 6.8 Hz), 7.58 (1H, s), 7.27-7.22 (4H, m), 5.37 (2H, s), 4.44 (2H, s), 3.54 (2H, t, J = 6.4 Hz), 3.16 (2H, t, J = 6.4 Hz). LC-MS([M + 2H]$^{2+}$/Rt (min)): 203.1/0.620 |

| Example | Chemical Structural Formula | Instrumental Analysis Data |
|---|---|---|
| 8 | 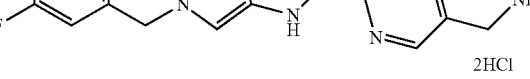 | $^1$H-NMR (400 MHz, CD$_3$OD): 8.90 (1H, d, J = 1.6 Hz), 8.61 (1H, s), 8.17 (1H, s), 7.65 (1H, d, J = 1.6 Hz), 7.35-7.28 (2H, m), 5.43 (2H, s), 4.54 (2H, s), 3.58 (2H, t, J = 6.4 Hz), 3.26 (2H, t, J = 6.4 Hz). LC-MS ([M + H]$^+$/Rt (min)): 388.2/0.554 |
| 9 | 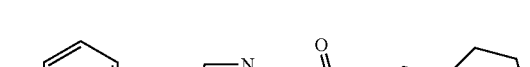 | $^1$H-NMR (400 MHz, CD$_3$OD): 8.94 (1H, s), 8.60 (1H, s), 8.12 (1H, s), 7.82 (1H, s), 7.76-7.65 (4H, m), 5.55 (2H, s), 4.53 (2H, s), 3.58 (2H, t, J = 5.2 Hz), 3.26 (2H, t, J = 6.4 Hz) LC-MS [M + 2H]$^{2+}$/Rt (min)): 201.7/0.659 |
| 10 | 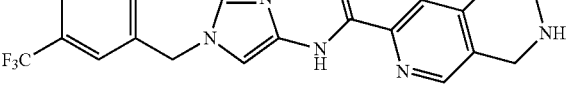 | $^1$H-NMR (400 MHz, CD$_3$OD): 8.84 (1H, s), 8.12 (1H, d, J = 8.4 Hz), 7.91 (1H, d, J = 8.4 Hz), 7.81 (1H, s), 7.75-7.64 (4H, m), 5.54 (2H, s), 4.53 (2H, s), 3.69 (2H, t, J = 6.4 Hz), 3.36 (2H, t, J = 6.4 Hz). LC-MS ([M + 2H]$^{2+}$/Rt (min)): 201.7/0.620 |
| 11 |  | $^1$H-NMR (400 MHz, CD$_3$OD): 8.80 (1H, d, J = 1.6 Hz), 8.13 (1H, d, J = 8.0 Hz), 7.92 (1H, d, J = 8.4 Hz), 7.67 (1H, d, J = 2.0 Hz), 7.33-7.26 (2H, m), 5.42 (2H, s), 4.54 (2H, s), 3.70 (2H, t, J = 6.4 Hz), 3.37 (2H, t, J = 6.4 H). LC-MS: [M + 2H]$^{2+}$/Rt (min): 194.7/0.636 |
| 12 | 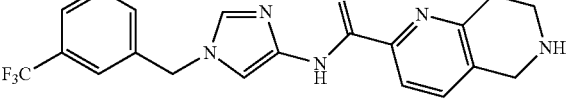 | $^1$H-NMR (400 MHz, CD$_3$OD): 9.03 (1H, s), 9.00 (1H, s), 8.31 (1H, s), 7.61 (1H, s), 7.32 (2H, t, J = 7.2 Hz), 5.44 (2H, s), 4.50 (2H, s), 3.61 (2H, t, J = 6.4 Hz), 3.26 (2H, t, J = 6.4 Hz). LC-MS: [M + 2H]$^{2+}$/Rt (min): 194.7/0.624 |
| 13 |  | $^1$H-NMR (400 MHz, CD$_3$OD): 9.00 (1H, d, J = 2.4 Hz), 8.76 (1H, s), 8.26 (1H, d, J = 1.6 Hz), 7.78-7.57 (4H, m), 7.56 (1H, d, J = 0.8 Hz), 5.51 (2H, s), 4.48 (2H, s), 3.60 (2H, t, J = 6.4 Hz), 3.24 (2H, t, J = 6.4 Hz). LC-MS: [M + H]$^+$/Rt (min): 402.3/0.590 |
| 14 | 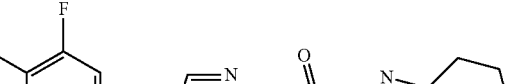 | $^1$H-NMR (400 MHz, CD$_3$OD): 8.72 (1H, s), 7.77 (1H, t, J = 7.6 Hz), 7.59 (1H, d, J = 1.2 Hz), 7.29-7.24 (3H, m), 5.39 (2H, s), 4.47 (2H, s), 3.58 (2H, t, J = 6.4 Hz), 3.15 (2H, t, J = 6.4 Hz). LC-MS: [M + 2H]$^{2+}$/Rt (min): 203.1/0.650 |
| 15 | 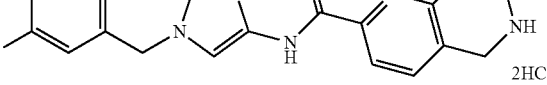 | $^1$H-NMR (400 MHz, CD$_3$OD): 8.83 (1H, s), 7.80-7.61 (5H, m), 7.59 (1H, d, J = 1.2 Hz), 7.24 (1H, d, J = 7.6 Hz), 5.52 (2H, s), 4.47 (2H, s), 3.58 (2H, t, J = 6.4 Hz), 3.15 (2H, t, J = 6.4 Hz). LC-MS: [M + 2H]$^{2+}$/Rt (min): 210.1/0.708 |

Examples 16 to 17

According to the process of Reference Example 3, the corresponding intermediates of Examples 16 to 17 were synthesized, and then the compounds of Examples 16 to 17 were prepared from the corresponding intermediates according to the process of Example 4 without purification.

| Example | Chemical Structural Formula | Instrumental Analysis Data |
|---|---|---|
| 16 | 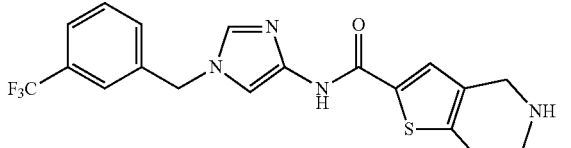 | LC-MS: $[M + 2H]^{2+}$/Rt (min): 204.2/0.632 |
| 17 | 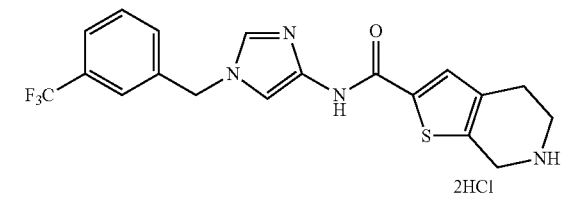 [SMILES: O=C(Nc1cn(Cc2cccc(C(F)(F)F)c2)cn1)c1cc2c(s1)CNCC2] | LC-MS: $[M + 2H]^{2+}$/Rt (min): 204.2/0.634 |

Examples 18 to 22

According to the process of Example 4, the compounds of Examples 18 to 22 were prepared from the corresponding compounds of each Reference Example.

| Example | Chemical Structural Formula | Instrumental Analysis Data |
|---|---|---|
| 18 | 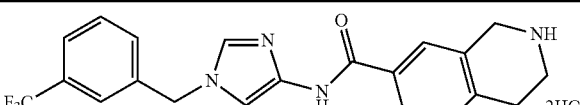 | LC-MS: $[M + H]^{+}$/Rt (min): 401.3/0.588 |
| 19 | 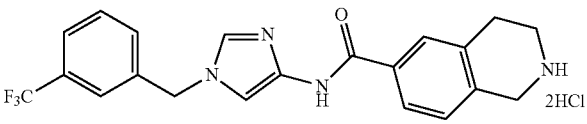 [SMILES: O=C(Nc1cn(Cc2cccc(C(F)(F)F)c2)cn1)c1ccc2c(c1)CCNC2] | LC-MS: $[M + 2H]^{2+}$/Rt (min): 201.2/0.663 |
| 20 | 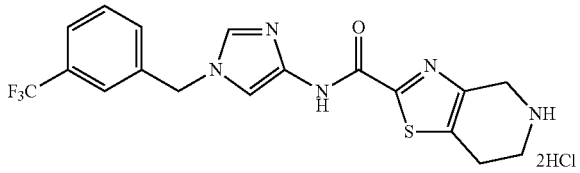 [SMILES: O=C(Nc1cn(Cc2cccc(C(F)(F)F)c2)cn1)c1nc2c(s1)CCNC2] | LC-MS: $[M + H]^{+}$/Rt (min): 408.2/0.603 |
| 21 | 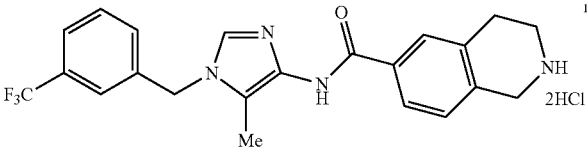 | $^1$H-NMR (400 MHz, CD$_3$OD): 8.93 (1H, s), 7.91-7.88 (2H, m), 7.78-7.60 (4H, m), 7.42 (1H, d, J = 8.0 Hz), 5.57 (2H, s), 4.47 (2H, s), 3.56 (2H, t, J = 6.4 Hz), 3.22 (2H, t, J = 6.4 Hz), 2.21 (3H, d, J = 1.2 Hz). LC-MS: $[M + 2H]^{2+}$/Rt (min): 208.2/0.668 |
| 22 |  | $^1$H-NMR (400 MHz, CD$_3$OD): 7.88-7.85 (2H, m), 7.75-7.73 (2H, m), 7.68-7.60 (2H, m), 7.42-7.38 (2H, m), 5.49 (2H, s), 4.46 (2H, s), 3.55 (2H, t, J = 6.4 Hz), 3.21 (2H, t, J = 6.0 Hz), 2.68 (3H, d, J = 2.4 Hz). LC-MS: $[M + 2H]^{2+}$/Rt (min): 208.2/0.583 |

Examples 23 to 24

According to the process of Reference Example 3, the compounds of Examples 23 to 24 were prepared from the corresponding compounds of each Reference Example and the corresponding starting compounds.

| Example | Chemical Structural Formula | LC-MS: [M + H]⁺/Rt (min) |
|---|---|---|
| 23 | | 401.9/0.844 |
| 24 | | 418.2/0.711 |

Example 25

N-[1-(3,4,5-Trifluorobenzyl)-1H-imidazol-4-yl]-(1,2,3,4-tetrahydroisoquinoline-6-carboxamide ditrifluoroacetate

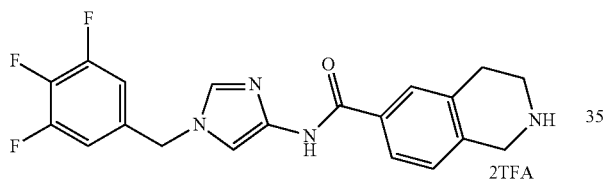

To a solution of the compound of Reference Example 28 (103 mg) in chloroform (9 mL) was added trifluoroacetic acid (1 mL), and the mixture was stirred at room temperature for 5 hours. The reaction mixture was concentrated in vacuo, to the residue was added a mixed solvent of hexane-ethyl acetate, and the mixture was stirred at room temperature for 1 hour. The resulting precipitate was collected on a filter and dried in vacuo to give the title compound (91 mg).

LC-MS ([M+2H]$^{2-}$/Rt (min)): 194.1/0.580

$^{1}$H-NMR (400 MHz, CDCl$_3$): δ 7.94 (1H, d, J=1.6 Hz), 7.85-7.83 (2H, m), 7.47 (d, 1H, J=2.0 Hz), 7.38 (d, 1H, J=8.4 Hz), 7.14 (dd, 2H, J=8.4, 6.8 Hz), 5.26 (s, 2H), 4.44 (s, 2H), 3.55 (t, 2H, J=6.4 Hz), 3.20 (t, 2H, J=6.4 Hz).

Examples 26 to 29

According to the process of Example 25, the compounds of Examples 26 to 29 were prepared from the corresponding compounds of each Reference Example.

| Example | Chemical Structural Formula | Instrumental Analysis Data |
|---|---|---|
| 26 | | LC-MS: [M + H]⁺/Rt (min): 401.3/0.588 |
| 27 | | LC-MS: [M + H]⁺/Rt (min): 401.3/0.899 |
| 28 | | LC-MS: [M + 2H]$^{2+}$/Rt (min): 194.5/0.601 |

| Example | Chemical Structural Formula | Instrumental Analysis Data |
|---|---|---|
| 29 | F$_3$C-benzyl-imidazole-CONH-(4,4-dimethyl-tetrahydroisoquinoline), 2TFA | LC-MS:<br>[M + H]$^+$/Rt (min):<br>429.3/0.706 |

Example 30

2-Methyl-N-{1-[3-(trifluoromethyl)benzyl]-1H-imidazol-4-yl}-1,2,3,4-tetrahydroisoquinoline-6-carboxamide

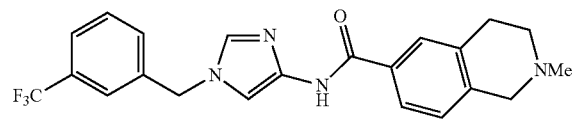 [SMILES: CN1CCc2cc(C(=O)Nc3cn(Cc4cccc(C(F)(F)F)c4)cn3)ccc2C1]

To a solution of the compound of Example 26 (33 mg) in THF (1 mL) were added aqueous formaldehyde solution (1 mL) and sodium triacetoxyborohydride (23 mg), and the mixture was stirred at room temperature for 19 hours. The reaction mixture was concentrated in vacuo, and the residue was dissolved in chloroform, washed with saturated aqueous sodium bicarbonate solution and brine, dried over anhydrous sodium sulfate, filtered, and then concentrated in vacuo. The resulting residue was purified by silica gel column chromatography (chloroform/methanol) to give the title compound (12 mg).
LC-MS ([M+H]$^+$/Rt (min)): 415.6/0.575

Example 31

N-[1-(3,4,5-Trifluorobenzyl)-1H-imidazol-4-yl]-1,2,3,4-tetrahydroisoquinoline-6-carboxamide

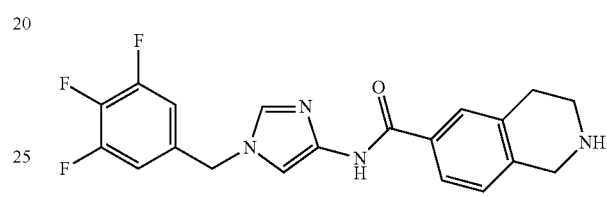

A suspension of the compound of Example 25 (80 mg) in ethyl acetate (100 mL) was washed with saturated aqueous sodium bicarbonate solution, and the resulting organic layer was dried over anhydrous sodium sulfate and then concentrated in vacuo to give the title compound (50 mg).
LC-MS ([M+2H]$^{2+}$/Rt (min)): 194.1/0.580

Examples 32 to 34

According to the process of Example 31, the compounds of Examples 32 to 34 were prepared from the corresponding compounds of each Reference Example.

| Example | Chemical Structural Formula | Instrumental Analysis Data |
|---|---|---|
| 32 | F$_3$C-benzyl-imidazole-CONH-(4,4-dimethyl-tetrahydroisoquinoline) | LC-MS:<br>[M + H]$^+$/Rt (min):<br>429.3/0.706 |
| 33 | F$_3$C-benzyl-imidazole-CONH-(isoindoline) | LC-MS:<br>[M + 2H]$^{2+}$/Rt (min):<br>194.5/0.601 |
| 34 | F$_3$C-benzyl-imidazole-CONH-(tetrahydroisoquinoline) | LC-MS:<br>[M + 2H]$^{2+}$/Rt (min):<br>201.2/0.617 |

Example 35

1-(3,4-Difluorobenzyl)-N-(5,6,7,8-tetrahydro-2,7-naphthyridin-3-yl)-1H-imidazole-4-carboxamide

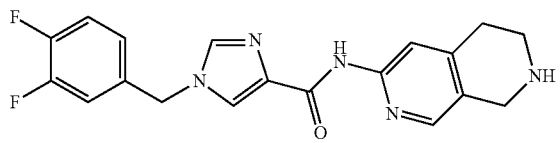 [SMILES: O=C(Nc1cc2c(cn1)CNCC2)c1cn(Cc2ccc(F)c(F)c2)cn1]

To a solution of the compound of Reference Example 33 (111 mg) in methanol (4 mL) was added 4 mol/L dioxane hydrochloride (1.66 mL), and the mixture was stirred at room temperature overnight. The mixture was then stirred at 50° C. for 6 hours. The reaction mixture was concentrated in vacuo, and then water and 2 mol/L aqueous sodium hydroxide solution were added thereto. The resulting precipitate was collected on a filter and washed with water and hexane/ethyl acetate (2/1). The resulting crude product was purified by amino silica gel column chromatography (chloroform/methanol) to give the title compound (29.5 mg).

LC-MS ([M+H]$^+$/Rt (min)): 370.2/0.618
$^1$H-NMR (400 MHz, DMSO-$d_6$): 9.31 (1H, s), 8.02-7.97 (3H, m), 7.90 (1H, s), 7.57-7.41 (2H, m), 7.25-7.21 (2H, m), 5.26 (2H, s), 3.79 (2H, s), 2.93-2.89 (2H, m), 2.72-2.68 (2H, m).

Examples 36 to 42

According to the process of Reference Example 3, the compounds of Examples 36 to 42 were prepared from the corresponding compounds of each Reference Example.

| Example | Chemical Structural Formula | LC-MS: [M + H]$^+$/Rt (min) |
|---|---|---|
| 36 | | 416.3/0.754 |
| 37 | | 401.2/0.715 |
| 38 | | 382.1/3.23 |
| 39 | | 396.1/3.21 |
| 40 | | 418.0/3.58 |
| 41 | | 380.2/3.23 |

-continued

| Example | Chemical Structural Formula | LC-MS: [M + H]⁺/Rt (min) |
|---|---|---|
| 42 | 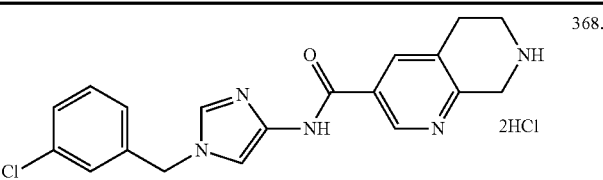 | 404.9/0.781 |

Examples 43 to 70

According to the process of Example 4, the compounds of Examples 43 to 70 were prepared from the corresponding compounds of each Reference Example.

| Example | Chemical Structural Formula | LC-MS: [M + H]⁺/Rt (min) |
|---|---|---|
| 43 |  | 368.2/0.563 |
| 44 | 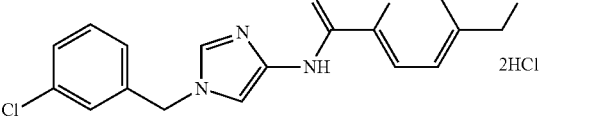 | 368.2/0.577 |
| 45 | 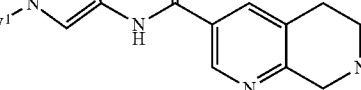 | 367.2/0.569 |

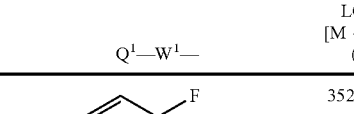

| Reference Example | Q¹—W¹— | LC-MS: [M + H]⁺/Rt (min) |
|---|---|---|
| 46 | 2-F-benzyl | 352.2/0.491 |
| 47 | 3,5-diF-benzyl | 370.3/0.524 |

-continued

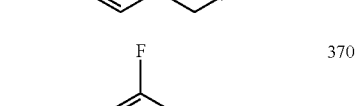

| Reference Example | Q¹—W¹— | LC-MS: [M + H]⁺/Rt (min) |
|---|---|---|
| 48 | 3,4-diF-benzyl | 379.3/0.523 |

-continued

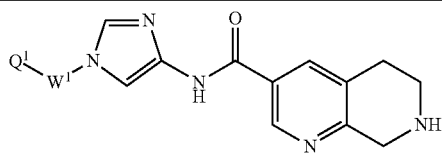

| Reference Example | Q¹—W¹— | LC-MS: [M + H]⁺/Rt (min) |
|---|---|---|
| 49 | 3-(F₃CO)-C₆H₄-CH₂- | 418.3/0.641 |
| 50 | 3-(PhO)-C₆H₄-CH₂- | 426.3/0.664 |
| 51 | 3-F,4-Cl-C₆H₃-CH₂- | 386.2/0.584 |
| 52 | 3-F,5-Cl-C₆H₃-CH₂- | 386.2/0.580 |
| 53 | 4-F,3-(F₃C)-C₆H₃-CH₂- | 420.3/0.616 |
| 54 | 4-Cl,3-(F₃C)-C₆H₃-CH₂- | 436.2/0.661 |
| 55 | cyclohexyl-CH₂- | 340.3/0.520 |
| 56 | cyclohexyl-CH₂CH₂- | 354.4/0.617 |
| 57 | pyridin-3-yl-CH₂- | 335.3/0.280 |
| 58 | 3-(MeO)-C₆H₄-CH₂- | 364.4/0.498 |
| 59 | C₆H₅-CH₂- | 334.3/0.466 |

-continued

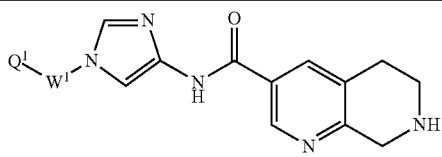

| Reference Example | Q¹—W¹— | LC-MS: [M + H]⁺/Rt (min) |
|---|---|---|
| 60 | 2-Me-C₆H₄-CH₂- | 348.4/0.534 |
| 61 | 4-F-C₆H₄-CH₂- | 352.3/0.487 |
| 62 | 2-(CF₃)-C₆H₄-CH₂- | 402.4/0.595 |
| 63 | 3-NC-C₆H₄-CH₂- | 359.3/0.443 |
| 64 | 4-(F₃C)-C₆H₄-CH₂- | 402.3/0.610 |
| 65 | 4-Cl-C₆H₄-CH₂- | 368.3/0.567 |
| 66 | naphthalen-2-yl-CH₂- | 384.4/0.618 |
| 67 | 3-(H₂N)-C₆H₄-CH₂- | 349.3/0.324 |
| 68 | 4-Me-C₆H₄-CH₂- | 348.3/0.536 |
| 69 | C₆H₅-CH₂CH₂CH₂- | 362.3/0.531 |
| 70 | 3-(OCF₃),5-Cl-C₆H₃-CH₂- | 452.3/0.687 |

Examples 71 to 93

According to the process of Example 1, the compounds of Examples 71 to 93 were prepared from the corresponding compounds of each Reference Example (Example).

| Example | Q¹—W¹— | LC-MS: [M + H]⁺/Rt (min) |
|---|---|---|
| 71 | benzyl | 333.2/0.558 |
| 72 | 2-fluorobenzyl | 351.3/0.581 |
| 73 | 3,4-difluorobenzyl | 369.2/0.633 |
| 74 | 3,5-difluorobenzyl | 369.2/0.626 |
| 75 | 4-(trifluoromethoxy)benzyl | 417.3/0.744 |
| 76 | 2-methylbenzyl | 347.3/0.626 |
| 77 | 3-fluorobenzyl | 351.2/0.593 |
| 78 | 3-methoxybenzyl | 363.3/0.660 |
| 79 | 4-fluorobenzyl | 351.2/0.668 |
| 80 | 3-methylbenzyl | 347.3/0.739 |
| 81 | 4-methylbenzyl | 347.2/0.551 |
| 82 | 2-(trifluoromethyl)benzyl | 401.3/0.609 |
| 83 | 4-(trifluoromethyl)benzyl | 401.3/0.627 |
| 84 | 4-methoxybenzyl | 363.2/0.494 |
| 85 | cyclohexylmethyl | 339.2/0.568 |
| 86 | 2-cyclohexylethyl | 353.3/0.633 |
| 87 | 4-chlorobenzyl | 367.1/0.562 |
| 88 | 3-cyanobenzyl | 358.4/0.444 |
| 89 | 3-phenoxybenzyl | 425.3/0.691 |
| 90 | 4-chloro-3-fluorobenzyl | 385.3/0.587 |
| 91 | 3-chloro-5-fluorobenzyl | 385.2/0.590 |

81
-continued

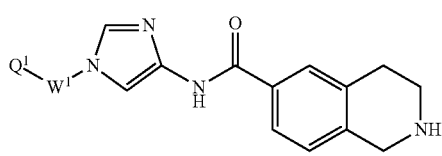

| Example | Q¹—W¹— | LC-MS: [M + H]⁺/Rt (min) |
|---|---|---|
| 92 | (F, F₃C-phenyl-CH₂-) | 419.3/0.629 |

82
-continued

| Example | Q¹—W¹— | LC-MS: [M + H]⁺/Rt (min) |
|---|---|---|
| 93 | (Cl, F₃C-phenyl-CH₂-) | 435.2/0.663 |

Examples 94 to 107

According to process of Example 1 or 4, the compounds of Examples 94 to 107 were prepared from the corresponding compounds of each Reference Example.

| Example | Chemical Structural Formula | Instrumental Analysis Data |
|---|---|---|
| 94 | 3,5-(MeO)₂-benzyl-imidazole-tetrahydroisoquinoline carboxamide · 2HCl | LC-MS ([M + 2H]²⁺/ Rt (min)): 197.3/0.510 |
| 95 | 3-Cl-4-F-benzyl-imidazole-tetrahydroisoquinoline carboxamide · 2HCl | LC-MS ([M + 2H]²⁺/ Rt (min)): 193.2/0.575 |
| 96 | 3,5-Br₂-benzyl-imidazole-tetrahydroisoquinoline carboxamide · 2HCl | LC-MS ([M + 2H]²⁺/ Rt (min)): 246.1/0.669 |
| 97 | 3-CF₃-4-Me-benzyl-imidazole-tetrahydroisoquinoline carboxamide · 2HCl | LC-MS ([M + 2H]²⁺/ Rt (min)): 208.2/0.656 |
| 98 | 3-CF₃-5-OMe-benzyl-imidazole-tetrahydroisoquinoline carboxamide · 2HCl | LC-MS ([M + 2H]²⁺/ Rt (min)): 216.3/0.638 |

-continued

| Example | Chemical Structural Formula | Instrumental Analysis Data |
|---|---|---|
| 99 | 3-CF₃, 5-F-benzyl imidazole tetrahydroisoquinoline carboxamide, 2HCl | LC-MS ([M + 2H]²⁺/ Rt (min)): 210.2/0.658 |
| 100 | 3-OCF₃, 5-Cl-benzyl imidazole tetrahydroisoquinoline carboxamide, 2HCl | LC-MS ([M + 2H]²⁺/ Rt (min)): 226.2/0.740 |
| 101 | 3,5-dichlorobenzyl imidazole tetrahydroisoquinoline carboxamide, 2HCl | LC-MS ([M + H]⁺/ Rt (min)): 401.2/0.656 |
| 102 | 3,4-dichlorobenzyl imidazole tetrahydroisoquinoline carboxamide | LC-MS ([M + 2H]²⁺/ Rt (min)): 201.2/0.630 |
| 103 | naphthalen-2-ylmethyl imidazole tetrahydroisoquinoline carboxamide | LC-MS ([M + 2H]²⁺/ Rt (min)): 192.2/0.607 |
| 104 | (5-CF₃-furan-2-yl)methyl imidazole tetrahydroisoquinoline carboxamide | LC-MS ([M + 2H]²⁺/ Rt (min)): 196.2/0.574 |
| 105 | 3-(dimethylamino)benzyl imidazole tetrahydroisoquinoline carboxamide | LC-MS ([M + H]⁺/ Rt (min)): 376.3/0.426 |
| 106 | pyridin-3-ylmethyl imidazole tetrahydroisoquinoline carboxamide | LC-MS ([M + H]⁺/ Rt (min)): 334.2/0.296 |

| Example | Chemical Structural Formula | Instrumental Analysis Data |
|---|---|---|
| 107 | 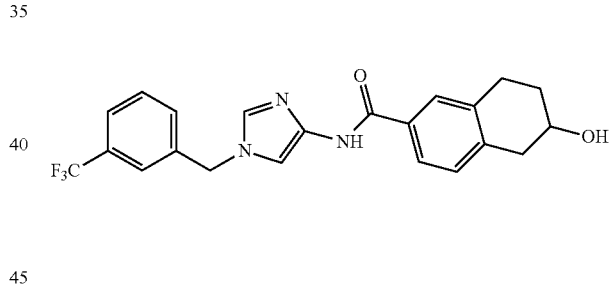 | LC-MS ([M + H]$^+$/Rt (min)): 349.2/0.416 |

Example 108

2-Acetyl-N-{1-[3-(trifluoromethyl)benzyl]-1H-imidazol-4-yl}-1,2,3,4-tetrahydroisoquinoline-6-carboxamide trifluoroacetate

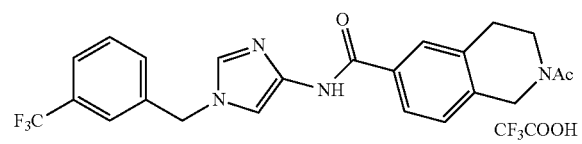

To a solution of the compound of Example 26 (0.03 g) in THF (1 mL) were added pyridine (25 μL) and acetic anhydride (12 μL), and the mixture was stirred at room temperature for 3 hours. The reaction solution was concentrated, and then the residue was purified by reverse-phase HPLC (mobile phase: 0.05% TFA/water and 0.035% TFA/acetonitrile) to give the title compound (0.02 g).

LC-MS ([M+H]$^+$/Rt (min)): 443.3/0.825

Example 109

N-{1-[3-(Trifluoromethyl)benzyl]-1H-imidazol-4-yl}-3',4'-dihydro-1'H-spiro[1,3-dioxolane-2,2'-naphthalene]-6'-carboxamide

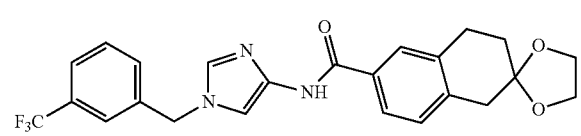 [SMILES: O=C(Nc1cn(Cc2cccc(C(F)(F)F)c2)cn1)c1ccc2c(c1)CCC1(C2)OCCO1]

According to the process of Reference Example 3, the title compound was prepared from the compound of Reference Example 11-2 and the compound described in U.S. Pat. No. 5,786,356.

LC-MS ([M+H]$^+$/Rt (min)): 458.4/0.870

Example 110

6-Oxo-N-{1-[3-(trifluoromethyl)benzyl]-1H-imidazol-4-yl}-5,6,7,8-tetrahydronaphthalene-2-carboxamide

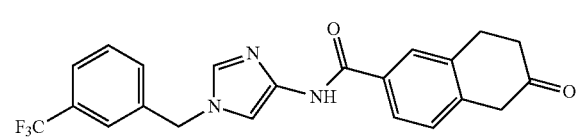

A solution of the compound of Example 109 (0.20 g) in a mixed solvent of 4 mol/L dioxane hydrochloride (4 mL) and water (1 mL) was stirred at room temperature for 20 hours. The reaction solution was diluted with ethyl acetate, and then washed with saturated aqueous sodium hydrogen carbonate and brine. The organic phase was dried over anhydrous sodium sulfate, filtered, and then concentrated in vacuo. The resulting residue was purified by silica gel column chromatography (chloroform/methanol) to give the title compound (0.15 g).

LC-MS ([M+H]$^+$/Rt (min)): 414.2/0.805

Example 111

6-Hydroxy-N-{1-[3-(trifluoromethyl)benzyl]-1H-imidazol-4-yl}-5,6,7,8-tetrahydronaphthalene-2-carboxamide To a solution of the compound of Example 110 (0.06 g) in methanol was added sodium borohydride (0.01 g) with ice-cooling, and then the mixture was stirred at room temperature for 1 hour. The reaction solution was diluted with ethyl acetate and then washed with water and brine. The organic phase was dried over anhydrous sodium sulfate, filtered, and then concentrated in vacuo. The resulting residue was purified by silica gel column chromatography (chloroform/methanol) to give the title compound (0.06 g).

LC-MS ([M+H]$^+$/Rt (min)): 416.3/0.754

Examples 112 to 121

According to the process of Example 4, the compounds of Examples 112 to 121 were prepared from the corresponding compounds of each Reference Example.

| Example | Chemical Structural Formula | Instrumental Analysis Data |
|---------|----------------------------|----------------------------|
| 112 | (structure with trifluorobenzyl imidazole, acrylamide, tetrahydroisoquinoline, 2HCl) | LC-MS ([M + 2H]$^{2+}$/Rt (min)): 207.2/0.649 |

| Reference Example | Q$^1$—W$^1$— | LC-MS: [M + H]$^+$/Rt (min) |
|------|---------|--------|
| 113 | EtO$_2$C-phenyl-CH$_2$— | 392.3/0.562 |
| 114 | MeO$_2$S-phenyl-CH$_2$— | 412.3/0.472 |
| 115 | phenyl-(CH$_2$)$_3$— | 477.4/1.031 |
| 116 | phenyl-O-CH$_2$CH$_2$— | 364.3/0.572 |
| 117 | phenyl-O-(CH$_2$)$_3$— | 378.3/0.579 |
| 118 | tetrahydropyran-4-yl-CH$_2$— | 342.3/0.430 |
| 119 | benzo[1,3]dioxol-5-yl-CH$_2$— | 378.3/0.517 |
| 120 | 3-F-phenyl-CH$_2$— | 352.3/0.615 |
| 121 | 3-Me-phenyl-CH$_2$— | 348.3/0.647 |

Test Example 1: Test for Inhibiting Sphere-Forming Ability of Cancer Cells

The reliable methods established for measuring the self-renewal ability of cells which is one of the CSC's properties include a method for measuring the sphere-forming ability of cancer cells in non-adherent condition in the absence of serum (Cancer Res 65, 5506-5511 (2005)). HCT-116 cells were available from the American Type Culture Collection (ATCC). HCT-116 cells were cultured at 37° C. and 5% $CO_2$ using the McCoy's 5a medium containing 10% fetal bovine serum (FBS) and 1% penicillin/streptomycin. HCT-116 cells were seeded in a 384 Well Black Clear Bottom Ultra-Low Attachment Microplate (Corning Cat. No. 3827) in an amount of 350-800 cells/well using the DMEM/F12 medium containing 2% B27 supplement (GIBCO), 20 ng/mL epidermal growth factor (EGF) (peprotech), 10 ng/mL basic fibroblast growth factor (bFGF) (peprotech), 5 μg/mL insulin (Sigma), and 1% penicillin/streptomycin. The test compounds were added into each well to adjust the final concentration of DMSO to 0.1%, and the cells were cultured for 4 days. The number of viable cells in each well was then measured with CellTiter-Glo® Luminescent Cell Viability Assay (Promega) to calculate the concentration of each test compound for 50% inhibition of cell proliferation (Sphere $IC_{50}$ value; μmol/L).

The experiment of Test Example 1 was performed for the compounds of each Example. The concentrations of each test compound for 50% inhibition of cell profeliration (Sphere $IC_{50}$ value; μmol/L) are shown in the following Table.

| Example | $IC_{50}$ (μmol/L) |
|---------|---------------------|
| 1 | 0.08 |
| 2 | 0.66 |
| 3 | 0.06 |
| 4 | 0.66 |
| 5 | 0.07 |
| 6 | 0.06 |
| 7 | 0.39 |
| 8 | 0.09 |
| 9 | 0.07 |
| 10 | 0.04 |
| 11 | 0.05 |
| 12 | 0.07 |
| 13 | 0.03 |
| 14 | 0.43 |
| 15 | 0.36 |
| 16 | 5.85 |
| 17 | 0.62 |
| 18 | 0.67 |
| 20 | 65.15 |
| 21 | 6.20 |
| 22 | 0.20 |
| 23 | 4.94 |
| 24 | 0.52 |

-continued

| Example | IC$_{50}$ (μmol/L) |
|---|---|
| 25 | 0.06 |
| 26 | 0.08 |
| 27 | 0.69 |
| 30 | 6.16 |
| 32 | 72.29 |
| 33 | 1.48 |
| 35 | 0.08 |
| 36 | 6.32 |
| 37 | 0.09 |
| 38 | 0.07 |
| 39 | 0.91 |
| 40 | 0.08 |
| 41 | 0.01 |
| 43 | 0.72 |
| 44 | 0.78 |
| 45 | 0.82 |
| 46 | 0.75 |
| 47 | 0.08 |
| 48 | 0.08 |
| 49 | 0.07 |
| 50 | 0.05 |
| 51 | 0.06 |
| 52 | 0.06 |
| 53 | 0.06 |
| 54 | <0.01 |
| 55 | 0.08 |
| 56 | 0.07 |
| 58 | 0.18 |
| 59 | 0.61 |
| 60 | 0.25 |
| 61 | 0.37 |
| 62 | 0.71 |
| 63 | 3.59 |
| 64 | 0.09 |
| 65 | 0.08 |
| 66 | 0.70 |
| 68 | 0.56 |
| 69 | 0.76 |
| 70 | 0.04 |
| 71 | 0.92 |
| 72 | 3.45 |
| 73 | 0.61 |
| 74 | 0.49 |
| 75 | 0.40 |
| 76 | 0.68 |
| 77 | 0.62 |
| 78 | 0.56 |
| 79 | 0.55 |
| 80 | 0.62 |
| 81 | 0.95 |
| 82 | 3.79 |
| 83 | 0.72 |
| 84 | 6.78 |
| 85 | 0.61 |
| 86 | 0.47 |
| 87 | 0.60 |
| 88 | 5.03 |
| 89 | 0.07 |
| 90 | 0.07 |
| 91 | 0.07 |
| 92 | 0.07 |
| 93 | <0.01 |
| 94 | 6.99 |
| 95 | 0.08 |
| 96 | 0.06 |
| 97 | 0.07 |
| 98 | 0.50 |
| 99 | 0.06 |
| 100 | 0.06 |
| 101 | 0.07 |
| 102 | 0.06 |
| 103 | 4.18 |
| 104 | 0.62 |
| 105 | 5.90 |
| 108 | 6.63 |
| 109 | 7.07 |
| 110 | 0.68 |

-continued

| Example | IC$_{50}$ (μmol/L) |
|---|---|
| 111 | 0.69 |
| 112 | 0.71 |
| 113 | 0.76 |
| 115 | 0.57 |
| 116 | 5.99 |
| 117 | 6.81 |
| 119 | 0.73 |
| 120 | 0.08 |
| 121 | 0.08 |

Test Example 2: Test for Inhibiting Sphere-Forming Ability of Cancer Cells (in the Presence of BSA)

HCT-116 cells were available from the American Type Culture Collection (ATCC). HCT-116 cells were cultured at 37° C. and 5% CO$_2$ using the McCoy's 5a medium containing 10% fetal bovine serum (FBS) and 1% penicillin/streptomycin. HCT-116 cells were seeded in a 384 Well Black Clear Bottom Ultra-Low Attachment Microplate (Corning Cat. No. 3827) in an amount of 350-800 cells/well using the DMEM/F12 medium containing 2% B27 supplement (GIBCO), 20 ng/mL epidermal growth factor (EGF) (peprotech), 10 ng/mL basic fibroblast growth factor (bFGF) (peprotech), 5 μg/mL insulin (Sigma), 5% bovine serum albumin (BSA), and 1% penicillin/streptomycin. The test compounds were added into each well to adjust the final concentration of DMSO to 0.1%, and the cells were cultured for 4 days. The number of viable cells in each well was then measured with CellTiter-Glo® Luminescent Cell Viability Assay (Promega) to calculate the concentration of each test compound for 50% inhibition of cell proliferation (Sphere IC$_{50}$ value; μmol/L).

The experiment of Test Example 2 was performed for the compounds of each Example. The concentrations of each test compound for 50% inhibition of cell profeliration (Sphere IC$_{50}$ value; μmol/L) are shown in the following Table.

| Example | IC$_{50}$ (μmol/L) |
|---|---|
| 1 | 0.17 |
| 2 | 0.49 |
| 3 | 0.03 |
| 4 | 0.56 |
| 5 | 0.06 |
| 6 | 0.05 |
| 7 | 0.61 |
| 8 | 0.44 |
| 9 | 0.50 |
| 10 | 0.05 |
| 11 | 0.05 |
| 12 | 0.06 |
| 13 | 0.06 |
| 14 | 0.46 |
| 15 | 0.55 |
| 16 | 6.00 |
| 17 | 0.72 |
| 18 | 0.70 |
| 21 | 6.19 |
| 22 | 0.58 |
| 24 | 0.67 |
| 25 | 0.09 |
| 26 | 0.10 |
| 27 | 6.01 |
| 35 | 0.05 |
| 37 | 0.59 |
| 38 | 0.09 |

-continued

| Example | IC$_{50}$ (μmol/L) |
|---|---|
| 39 | 0.79 |
| 40 | 0.07 |
| 41 | 0.02 |
| 43 | 0.54 |
| 44 | 0.58 |
| 45 | 0.66 |
| 46 | 0.44 |
| 47 | 0.05 |
| 48 | 0.06 |
| 49 | 0.07 |
| 50 | 0.66 |
| 51 | 0.05 |
| 52 | 0.06 |
| 53 | 0.06 |
| 54 | 0.03 |
| 55 | 0.05 |
| 56 | 0.16 |
| 58 | 0.08 |
| 59 | 0.37 |
| 60 | 0.10 |
| 61 | 0.06 |
| 62 | 0.59 |
| 63 | 0.71 |
| 64 | 0.17 |
| 65 | 0.38 |
| 66 | 5.49 |
| 67 | 8.52 |
| 68 | 0.65 |
| 69 | 0.68 |
| 70 | 0.06 |
| 71 | 0.77 |
| 72 | 5.46 |
| 73 | 0.54 |
| 74 | 0.49 |
| 75 | 0.61 |
| 76 | 0.59 |
| 77 | 0.60 |
| 78 | 0.56 |
| 79 | 0.49 |
| 80 | 0.60 |
| 81 | 6.22 |
| 82 | 4.90 |
| 83 | 0.54 |
| 85 | 0.59 |
| 86 | 0.56 |
| 87 | 0.58 |
| 88 | 0.95 |
| 89 | 0.64 |
| 90 | 0.10 |
| 91 | 0.08 |
| 92 | 0.09 |
| 93 | 0.07 |
| 94 | 6.11 |
| 95 | 0.09 |
| 96 | 0.20 |
| 97 | 0.59 |
| 98 | 0.51 |
| 99 | 0.06 |
| 100 | 0.07 |
| 101 | 0.06 |
| 102 | 0.06 |
| 103 | 6.10 |
| 104 | 0.53 |
| 105 | 5.12 |
| 107 | 6.34 |
| 110 | 0.58 |
| 111 | 0.98 |
| 112 | 6.34 |
| 113 | 0.58 |
| 115 | 0.54 |
| 116 | 1.97 |
| 117 | 5.68 |
| 118 | 6.18 |
| 119 | 0.63 |
| 120 | 0.07 |
| 121 | 0.07 |

Test Example 3: Pharmacokinetic Assay in Mouse

A 7-week-old mouse (BALB/cAnNCrlCrlj, female, CHARLES RIVER LABORATORIES JAPAN, INC.) receives single oral administration of each compound suspended in 0.5% methylcellulose solution in a dose of 10 mg/kg or 100 mg/kg. Blood is collected from the mouse 0.5, 1, 2, 4, 8 and 24 hours after the administration, and plasma from the blood is collected by centrifugation. The area under the plasma concentration-time curve (AUC) is calculated on the basis of the concentration changes to calculate the bioavailability of each compound according to the following formula:

Bioavailabity (%)=AUC after oral administration/
AUC after intravenous administration×100

Plasma is deproteinized by adding methanol at the final concentration of 80%, centrifuging the methanol solution, and filtrating the contrifuged solution, and then the present compound in the deproteinized plasma is detected and quantified with an LC-MS/MS (API4000, AB SCIEX). When the present compound is quantified, a calibration curve is prepared based on the mouse plasma added with a given amount of the compound. Bezafibrate is used as internal standard.

Test Example 4: Anti-Tumor Effect to HCT-116 Tumor-Bearing Mouse

The present compound can be used to evaluate the anti-tumor effect thereof. A 4 to 7-week-old nude mouse (BALB/cAnNCrj-nu/nu, female, CHARLES RIVER LABORATORIES JAPAN, INC.) received intradermal transplantation of HCT-116 cells (ATCC) in an amount of $3\times10^6$ cells/mouse around the ventral portion. The engraftment of HCT-116 cells was observed 5 to 14 days after the transplantation, and then each compound suspended in a solvent such as 0.5% methylcellulose solution was orally administrated to the mouse in a dose of 1 to 100 mg/kg one to twice daily. The tumor volume was measured over time after the administration to evaluate the effect for reducing the tumor volume by the administration of each compound. The tumor volume can be calculated from the minor axis and the major axis of the tumor measured with a digital caliper (Mitutoyo) according to the following formula:

Tumor volume [mm$^3$]=0.5×minor axis [mm]×(major axis [mm])$^2$

The tumor volume in control administration group treated with only a solvent such as 0.5% methylcellulose solution was compared with that of the present compound administration group, and T/C value was calculated according the following formula to evaluate the anti-tumor effect of the present compound.

T/C(%)=(the tumor volume at the end of administration in the present compound administration group−the tumor volume at the start of administration in the present compound administration group)/(the tumor volume at the end of administration in the control administration group−the tumor volume at the start of administration in the the control administration group)×100

The T/C values (%) of the present compound on each dosage and administration period in the HCT-116 tumor-bearing mouse are shown below.

| Examples | dosage (mg/kg) | administration period (day) | T/C (%) |
|---|---|---|---|
| 3 | 10 | 17 | 90 |
| 3 | 30 | 17 | 79 |
| 5 | 30 | 17 | 71 |
| 5 | 100 | 17 | 42 |
| 6 | 30 | 17 | 73 |
| 10 | 30 | 17 | 55 |
| 10 | 100 | 17 | 49 |
| 11 | 30 | 17 | 62 |
| 11 | 100 | 17 | 46 |
| 12 | 30 | 17 | 79 |
| 12 | 100 | 17 | 73 |
| 13 | 30 | 17 | 62 |
| 13 | 100 | 17 | 59 |

INDUSTRIAL APPLICABILITY

The present compound has a potent inhibitory effect on sphere-forming ability of cancer cells, and is useful as an orally-available anti-cancer agent.

The invention claimed is:
1. A compound of formula (1):

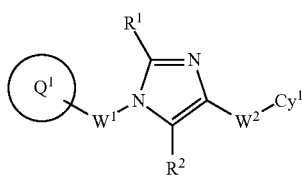

(1)

or a pharmaceutically acceptable salt thereof, wherein ring $Q^1$ is optionally-substituted $C_{6-10}$ aryl group, optionally-substituted $C_{3-10}$ cycloalkyl group, or optionally-substituted 5- to 10-membered heteroaryl group, wherein the substituents of the $C_{6-10}$ aryl group, the $C_{3-10}$ cycloalkyl group, or 5- to 10-membered heteroaryl group are selected from the group consisting of:
(a) halogen;
(b) $C_{1-6}$ alkyl which is optionally substituted with 1 to 3 groups independently selected from the group consisting of halogen, hydroxy, and $C_{1-6}$ alkoxy;
(c) $C_{1-6}$ alkoxy which is optionally substituted with 1 to 3 groups independently selected from the group consisting of halogen, hydroxy, and $C_{1-6}$ alkoxy;
(d) cyano;
(e) $C_{6-10}$ aryl which is optionally substituted with 1 to 4 groups independently selected from the group consisting of halogen, $C_{1-6}$ alkyl, and $C_{1-6}$ alkoxy;
(f) 5- or 6-membered heteroaryl which is optionally substituted with 1 to 4 groups independently selected from the group consisting of halogen, $C_{1-6}$ alkyl, and $C_{1-6}$ alkoxy;
(g) $C_{6-10}$ aryloxy which is optionally substituted with 1 to 4 groups independently selected from the group consisting of halogen, $C_{1-6}$ alkyl, and $C_{1-6}$ alkoxy;
(h) hydroxy,
(i) amino which is optionally substituted with 1 to 2 independently selected $C_{1-6}$ alkyl groups;
(j) aminocarbonyl, wherein the amino moiety is optionally substituted with 1 to 2 independently selected $C_{1-6}$ alkyl groups;
(k) $C_{1-6}$ alkoxy-carbonyl, wherein the alkoxy moiety is optionally substituted with 1 to 3 groups independently selected from the group consisting of halogen, hydroxy, and $C_{1-6}$ alkoxy;
(l) $C_{1-6}$ alkyl-carbonyl, wherein the alkyl moiety is optionally substituted with 1 to 3 groups independently selected from the group consisting of halogen, hydroxy, and $C_{1-6}$ alkoxy;
(m) $C_{1-6}$ alkylsulfonyl, wherein the alkyl moiety is optionally substituted with 1 to 3 groups independently selected from the group consisting of halogen, hydroxy, and $C_{1-6}$ alkoxy;
(n) $C_{1-6}$ alkyl-carbonylamino, wherein the alkyl moiety is optionally substituted with 1 to 3 groups independently selected from the group consisting of halogen, hydroxy, and $C_{1-6}$ alkoxy;
(o) $C_{1-6}$ alkylsulfonylamino, wherein the alkyl moiety is optionally substituted with 1 to 3 groups independently selected from the group consisting of halogen, hydroxy, and $C_{1-6}$ alkoxy;
(p) $C_{1-6}$ alkoxy-carbonylamino, wherein the alkoxy moiety is optionally substituted 1 to 3 groups independently selected from the group consisting of halogen, hydroxy, and $C_{1-6}$ alkoxy;
(q) $C_{1-6}$ alkyl-carbonyloxy, wherein the alkyl moiety is optionally substituted with 1 to 3 groups independently selected from the group consisting of halogen, hydroxy, and $C_{1-6}$ alkoxy;
(r) aminosulfonyl, wherein the amino moiety is optionally substituted with 1 to 2 independently selected $C_{1-6}$ alkyl groups; and
(s) $C_{3-10}$ cycloalkyl, which is optionally substituted with 1 to 4 groups independently selected from the group consisting of halogen, hydroxy, and $C_{1-6}$ alkoxy;
$R^1$ and $R^2$ are independently hydrogen, halogen, or $C_{1-6}$ alkyl which is optionally substituted with 1 to 3 independently selected halogen groups;
$W^1$ is optionally-substituted $C_{1-4}$ alkylene group, wherein the substituents of $C_{1-4}$ alkylene group are selected from the group consisting of halogen, hydroxy, and $C_{1-6}$ alkoxy;
$W^2$-$Cy^1$ is —$NR^{3a}C(O)$-$Cy^1$, —$NR^{3a}C(O)O$-$Cy^1$, —$NR^{3a}C(O)OCH_2$-$Cy^1$, —$NR^{3a}C(O)NR^{3b}$-$Cy^1$, —$NR^{3a}C(O)NR^{3b}CH_2$-$Cy^1$, —$NR^{3a}C(O)CH_2O$-$Cy^1$, —$NR^{3a}C(O)CH_2$-$Cy^1$, —$NR^{3a}C(O)CH_2CH_2$-$Cy^1$, —$C(O)NR^{3a}$-$Cy^1$, —$C(O)NR^{3a}CH_2$-$Cy^1$, —$C(O)NR^{3a}CH_2CH_2$-$Cy^1$, or —$NR^{3a}C(O)$—$CR^{3c}$=$CR^{3d}$-$Cy^1$ wherein $R^{3a}$ and $R^{3b}$ are independently hydrogen or $C_{1-6}$ alkyl; and $R^{3c}$ and $R^{3d}$ are independently hydrogen, fluorine, or $C_{1-6}$ alkyl; and
$Cy^1$ is a group of the following formula (11), (12), (13), or (15):

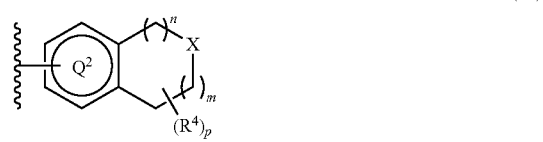

(11)

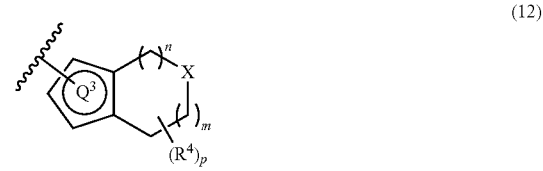

(12)

-continued

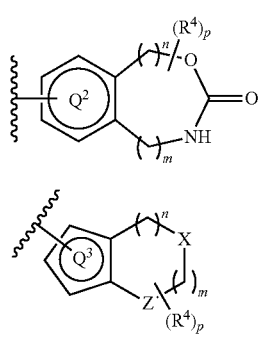

(13)

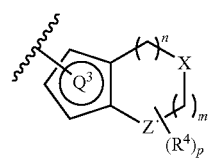

(15)

wherein ring $Q^2$ is an optionally-substituted benzene ring, an optionally-substituted pyridine ring, an optionally-substituted pyrimidine ring, an optionally-substituted pyridazine ring, or an optionally-substituted pyrazine ring, wherein the substituents of the benzene ring, pyridine ring, pyrimidine ring, pyridazine ring, or pyrazine ring are selected from the group consisting of:
(a) halogen,
(b) $C_{1-6}$ alkyl which is optionally substituted with 1 to 3 groups independently selected from the group consisting of halogen, hydroxy, and $C_{1-6}$ alkoxy;
(c) $C_{1-6}$ alkoxy which is optionally substituted with 1 to 3 groups independently selected from the group consisting of halogen, hydroxy, and $C_{1-6}$ alkoxy;
(d) cyano,
(e) $C_{6-10}$ aryl which is optionally substituted with 1 to 4 groups independently selected from the group consisting of halogen, $C_{1-6}$ alkyl, and $C_{1-6}$ alkoxy;
(f) 5- or 6-membered heteroaryl which is optionally substituted with 1 to 4 groups independently selected from the group consisting of halogen, $C_{1-6}$ alkyl, and $C_{1-6}$ alkoxy;
(g) $C_{6-10}$ aryloxy which is optionally substituted with 1 to 4 groups independently selected from the group consisting of halogen, $C_{1-6}$ alkyl, and $C_{1-6}$ alkoxy;
(h) hydroxy;
(i) amino which is optionally substituted with 1 to 2 independently selected $C_{1-6}$ alkyl groups;
(j) aminocarbonyl, wherein the amino moiety is optionally substituted with 1 to 2 independently selected $C_{1-6}$ alkyl groups;
(k) $C_{1-6}$ alkoxy-carbonyl, wherein the alkoxy moiety is optionally substituted with 1 to 3 groups independently selected from the group consisting of halogen, hydroxy, and $C_{1-6}$ alkoxy;
(l) $C_{1-6}$ alkyl-carbonyl, wherein the alkyl moiety is optionally substituted with 1 to 3 groups independently selected from the group consisting of halogen, hydroxy, and $C_{1-6}$ alkoxy;
(m) $C_{1-6}$ alkylsulfonyl, wherein the alkyl moiety is optionally substituted with 1 to 3 groups independently selected from the group consisting of halogen, hydroxy, and $C_{1-6}$ alkoxy;
(n) $C_{1-6}$ alkyl-carbonylamino, wherein the alkyl moiety is optionally substituted with 1 to 3 groups independently selected from the group consisting of halogen, hydroxy, and $C_{1-6}$ alkoxy;
(o) $C_{1-6}$ alkylsulfonylamino, wherein the alkyl moiety is optionally substituted with 1 to 3 groups independently selected from the group consisting of halogen, hydroxy, and $C_{1-6}$ alkoxy;
(p) $C_{1-6}$ alkoxy-carbonylamino, wherein the alkoxy moiety is optionally substituted with 1 to 3 groups independently selected from the group consisting of halogen, hydroxy, and $C_{1-6}$ alkoxy;
(q) $C_{1-6}$ alkyl-carbonyloxy, wherein the alkyl moiety is optionally substituted with 1 to 3 groups independently selected from the group consisting of halogen, hydroxy, and $C_{1-6}$ alkoxy;
(r) aminosulfonyl, wherein the amino moiety is optionally substituted with 1 to 2 independently selected $C_{1-6}$ alkyl groups; and
(s) $C_{3-10}$ cycloalkyl which is optionally substituted with 1 to 4 groups independently selected from the group consisting of halogen, hydroxy, and $C_{1-6}$ alkoxy;
ring $Q^3$ is an optionally-substituted 5-membered heteroaryl ring;
n and m are independently 0, 1 or 2, provided that n and m are not simultaneously 0;
X and Z are independently $NR^5$, $-NR^{3e}C(O)-$, $-C(O)NR^{3e}-$, or O wherein $R^5$ is hydrogen or $C_{1-6}$ alkyl which is optionally substituted with 1 to 3 independently selected halogen groups; and $R^{3e}$ is hydrogen or $C_{1-6}$ alkyl;
p is 1, 2, 3, 4 or 5; and
$R^4$ is, independently when two or more exist, hydrogen, halogen, hydroxy, oxo, a $C_{1-6}$ alkyl group which optionally substituted with 1 to 3 independently selected halogen groups, or a $C_{1-6}$ alkoxy group which is optionally substituted with 1 to 3 independently selected halogen groups; or
when two $R^4$ are attached to the same carbon atom or adjacent carbon atoms on the ring, they may be combined with the carbon atom(s) to form
(1) a 5- to 8-membered saturated or partially-unsaturated carbocyclic ring which is optionally substituted with 1 to 4 groups independently selected from the group consisting of halogen, hydroxy, $C_{1-6}$ alkyl, and $C_{1-6}$ alkoxy, or
(2) a 5- to 8-membered saturated or partially-unsaturated heterocyclic ring which is optionally substituted with 1 to 4 groups independently selected from the group consisting of halogen, hydroxy, $C_{1-6}$ alkyl, and $C_{1-6}$ alkoxy.

2. A compound of formula (1):

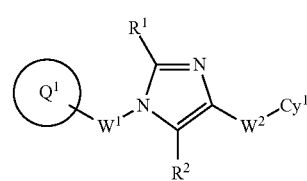

(1)

or a pharmaceutically acceptable salt thereof, wherein ring $Q^1$ is an optionally-substituted $C_{6-10}$ aryl group, an optionally-substituted $C_{3-10}$ cycloalkyl group, or an optionally-substituted 5- to 10-membered heteroaryl group, wherein the substituents of the $C_{6-10}$ aryl group, $C_{3-10}$ cycloalkyl group, or 5- to 10-membered heteroaryl group are selected from the group consisting of
(a) halogen;
(b) $C_{1-6}$ alkyl which is optionally substituted with 1 to 3 groups independently selected from the group consisting of halogen, hydroxy, and $C_{1-6}$ alkoxy;

(c) $C_{1-6}$ alkoxy which is optionally substituted with 1 to 3 groups independently selected from the group consisting of halogen, hydroxy, and $C_{1-6}$ alkoxy;
(d) cyano,
(e) $C_{6-10}$ aryl which is optionally substituted with 1 to 4 groups independently selected from the group consisting of halogen, $C_{1-6}$ alkyl, and $C_{1-6}$ alkoxy;
(f) 5- or 6-membered heteroaryl which is optionally substituted with 1 to 4 groups independently selected from the group consisting of halogen, $C_{1-6}$ alkyl, and $C_{1-6}$ alkoxy;
(g) $C_{6-10}$ aryloxy which is optionally substituted with 1 to 4 groups independently selected from the group consisting of halogen, $C_{1-6}$ alkyl, and $C_{1-6}$ alkoxy;
(h) hydroxy,
(i) amino which is optionally substituted with 1 to 2 independently selected $C_{1-6}$ alkyl groups;
(j) aminocarbonyl, wherein the amino moiety is optionally substituted with 1 to 2 independently selected $C_{1-6}$ alkyl groups;
(k) $C_{1-6}$ alkoxy-carbonyl, wherein the alkoxy moiety is optionally substituted with 1 to 3 groups independently selected from the group consisting of halogen, hydroxy, and $C_{1-6}$ alkoxy;
(l) $C_{1-6}$ alkyl-carbonyl, wherein the alkyl moiety is optionally substituted with 1 to 3 groups independently selected from the group consisting of halogen, hydroxy, and $C_{1-6}$ alkoxy;
(m) $C_{1-6}$ alkylsulfonyl, wherein the alkyl moiety is optionally substituted with 1 to 3 groups independently selected from the group consisting of halogen, hydroxy, and $C_{1-6}$ alkoxy;
(n) $C_{1-6}$ alkyl-carbonylamino, wherein the alkyl moiety is optionally substituted with 1 to 3 groups independently selected from the group consisting of halogen, hydroxy, and $C_{1-6}$ alkoxy;
(o) $C_{1-6}$ alkylsulfonylamino, wherein the alkyl moiety is optionally substituted with 1 to 3 groups independently selected from the group consisting of halogen, hydroxy, and $C_{1-6}$ alkoxy;
(p) $C_{1-6}$ alkoxy-carbonylamino, wherein the alkoxy moiety is optionally substituted with 1 to 3 groups independently selected from the group consisting of halogen, hydroxy, and $C_{1-6}$ alkoxy;
(q) $C_{1-6}$ alkyl-carbonyloxy, wherein the alkyl moiety is optionally substituted with 1 to 3 groups independently selected from the group consisting of halogen, hydroxy, and $C_{1-6}$ alkoxy;
(r) aminosulfonyl, wherein the amino moiety is optionally substituted with 1 to 2 independently selected $C_{1-6}$ alkyl groups; and
(s) $C_{3-10}$ cycloalkyl which is optionally substituted with 1 to 4 groups independently selected from the group consisting of halogen, hydroxy, and $C_{1-6}$ alkoxy;
$R^1$ and $R^2$ are independently hydrogen, halogen, or a $C_{1-6}$ alkyl group which is optionally substituted with 1 to 3 independently selected halogen groups;
$W^1$ is an optionally-substituted $C_{1-4}$ alkylene group, wherein, the substituents of the $C_{1-4}$ alkylene group are selected from the group consisting of halogen, hydroxy, and $C_{1-6}$ alkoxy;
$W^2$-$Cy^1$ is —$NR^{3a}C(O)$-$Cy^1$, —$NR^{3a}C(O)O$-$Cy^1$, —$NR^{3a}C(O)OCH_2$-$Cy^1$, —$NR^{3a}C(O)NR^{3b}$-$Cy^1$, —$NR^{3a}C(O)NR^{3b}CH_2$-$Cy^1$, —$NR^{3a}C(O)CH_2$-$Cy^1$, —$NR^{3a}C(O)CH_2CH_2$-$Cy^1$, —$C(O)NR^{3a}$-$Cy^1$, —$C(O)NR^{3a}CH_2$-$Cy^1$, or —$C(O)NR^{3a}CH_2CH_2$-$Cy^1$ wherein $R^{3a}$ and $R^{3b}$ are independently hydrogen or $C_{1-6}$ alkyl; and
$Cy^1$ is a group of the following formula (11), (12), or (13):

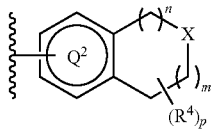
(11)

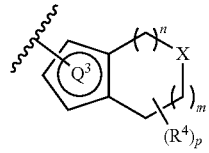
(12)

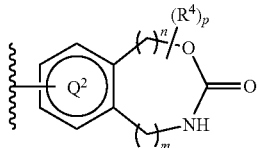
(13)

wherein ring $Q^2$ is an optionally-substituted benzene ring, an optionally-substituted pyridine ring, an optionally-substituted pyrimidine ring, an optionally-substituted pyridazine ring, or an optionally-substituted pyrazine ring, wherein the substituents of the benzene ring, pyridine ring, pyrimidine ring, pyridazine ring, or pyrazine ring are selected from the group consisting of:
(a) halogen;
(b) $C_{1-6}$ alkyl which is optionally substituted with 1 to 3 groups independently selected from the group consisting of halogen, hydroxy, and $C_{1-6}$ alkoxy;
(c) $C_{1-6}$ alkoxy which is optionally substituted with 1 to 3 groups independently selected from the group consisting of halogen, hydroxy, and $C_{1-6}$ alkoxy;
(d) cyano,
(e) $C_{6-10}$ aryl which is optionally substituted with 1 to 4 groups independently selected from the group consisting of halogen, $C_{1-6}$ alkyl, and $C_{1-6}$ alkoxy;
(f) 5- or 6-membered heteroaryl which is optionally substituted with 1 to 4 groups independently selected from the group consisting of halogen, $C_{1-6}$ alkyl, and $C_{1-6}$ alkoxy;
(g) $C_{6-10}$ aryloxy which is optionally substituted with 1 to 4 groups independently selected from the group consisting of halogen, $C_{1-6}$ alkyl, and $C_{1-6}$ alkoxy;
(h) hydroxy,
(i) amino which is optionally substituted with 1 to 2 independently selected $C_{1-6}$ alkyl groups;
(j) aminocarbonyl, wherein the amino moiety is optionally substituted with 1 to 2 independently selected $C_{1-6}$ alkyl groups;
(k) $C_{1-6}$ alkoxy-carbonyl, wherein the alkoxy moiety is optionally substituted with 1 to 3 groups independently selected from the group consisting of halogen, hydroxy, and $C_{1-6}$ alkoxy;
(l) $C_{1-6}$ alkyl-carbonyl, wherein the alkyl moiety is optionally substituted with 1 to 3 groups independently selected from the group consisting of halogen, hydroxy, and $C_{1-6}$ alkoxy;

(m) $C_{1-6}$ alkylsulfonyl, wherein the alkyl moiety is optionally substituted with 1 to 3 groups independently selected from the group consisting of halogen, hydroxy, and $C_{1-6}$ alkoxy;
(n) $C_{1-6}$ alkyl-carbonylamino, wherein the alkyl moiety is optionally substituted with 1 to 3 groups independently selected from the group consisting of halogen, hydroxy, and $C_{1-6}$ alkoxy;
(o) $C_{1-6}$ alkylsulfonylamino, wherein the alkyl moiety is optionally substituted with 1 to 3 groups independently selected from the group consisting of halogen, hydroxy, and $C_{1-6}$ alkoxy;
(p) $C_{1-6}$ alkoxy-carbonylamino, wherein the alkoxy moiety is optionally substituted with 1 to 3 groups independently selected from the group consisting of halogen, hydroxy, and $C_{1-6}$ alkoxy;
(q) $C_{1-6}$ alkyl-carbonyloxy, wherein the alkyl moiety is optionally substituted with 1 to 3 groups independently selected from the group consisting of halogen, hydroxy, and $C_{1-6}$ alkoxy;
(r) aminosulfonyl, wherein the amino moiety is optionally substituted with 1 to 2 independently selected $C_{1-6}$ alkyl groups; and
(s) $C_{3-10}$ cycloalkyl which is optionally substituted with 1 to 4 groups independently selected from the group consisting of halogen, hydroxy, and $C_{1-6}$ alkoxy;
ring $Q^3$ is an optionally-substituted 5-membered heteroaryl ring;
n and m are independently 0, 1 or 2, provided that n and m are not simultaneously 0;
X is $NR^5$ or O wherein $R^5$ is hydrogen or $C_{1-6}$ alkyl which is optionally substituted with 1 to 3 independently selected halogen groups;
p is 1, 2, 3, 4 or 5; and
$R^4$ is, independently when two or more exist, hydrogen, halogen, or a $C_{1-6}$ alkyl group which is optionally substituted with 1 to 3 independently selected halogen groups.

3. The compound according to claim 1 or a pharmaceutically acceptable salt thereof, wherein ring $Q^1$ is
(1) $C_{6-10}$ aryl group which is optionally substituted with 1 to 5 groups independently selected from the group consisting of:
(a) halogen,
(b) $C_{1-6}$ alkyl which is optionally substituted with 1 to 3 groups independently selected from the group consisting of halogen, hydroxy, and $C_{1-6}$ alkoxy,
(c) $C_{1-6}$ alkoxy which is optionally substituted with 1 to 3 groups independently selected from the group consisting of halogen, hydroxy, and $C_{1-6}$ alkoxy,
(d) cyano,
(e) $C_{6-10}$ aryl which is optionally substituted with 1 to 4 groups independently selected from the group consisting of halogen, $C_{1-6}$ alkyl, and $C_{1-6}$ alkoxy,
(f) 5- or 6-membered heteroaryl which is optionally substituted with 1 to 4 groups independently selected from the group consisting of halogen, $C_{1-6}$ alkyl, and $C_{1-6}$ alkoxy,
(g) $C_{6-10}$ aryloxy which is optionally substituted with 1 to 4 groups independently selected from the group consisting of halogen, $C_{1-6}$ alkyl, and $C_{1-6}$ alkoxy,
(h) hydroxy,
(i) amino which is optionally substituted with 1 to 2 independently selected $C_{1-6}$ alkyl groups,
(j) aminocarbonyl wherein the amino moiety thereof is optionally substituted with 1 to 2 independently selected $C_{1-6}$ alkyl groups,
(k) $C_{1-6}$ alkoxy-carbonyl wherein the alkoxy moiety is optionally substituted with 1 to 3 groups independently selected from the group consisting of halogen, hydroxy, and $C_{1-6}$ alkoxy,
(l) $C_{1-6}$ alkyl-carbonyl wherein the alkyl moiety is optionally substituted with 1 to 3 groups independently selected from the group consisting of halogen, hydroxy, and $C_{1-6}$ alkoxy,
(m) $C_{1-6}$ alkylsulfonyl wherein the alkyl moiety is optionally substituted with 1 to 3 groups independently selected from the group consisting of halogen, hydroxy, and $C_{1-6}$ alkoxy,
(n) $C_{1-6}$ alkyl-carbonylamino wherein the alkyl moiety is optionally substituted with 1 to 3 groups independently selected from the group consisting of halogen, hydroxy, and $C_{1-6}$ alkoxy,
(o) $C_{1-6}$ alkylsulfonylamino wherein the alkyl moiety is optionally substituted with 1 to 3 groups independently selected from the group consisting of halogen, hydroxy, and $C_{1-6}$ alkoxy,
(p) $C_{1-6}$ alkoxy-carbonylamino wherein the alkoxy moiety is optionally substituted with 1 to 3 groups independently selected from the group consisting of halogen, hydroxy, and $C_{1-6}$ alkoxy,
(q) $C_{1-6}$ alkyl-carbonyloxy wherein the alkyl moiety is optionally substituted with 1 to 3 groups independently selected from the group consisting of halogen, hydroxy, and $C_{1-6}$ alkoxy,
(r) aminosulfonyl wherein the amino moiety is optionally substituted with 1 to 2 independently selected $C_{1-6}$ alkyl groups, and
(s) $C_{3-10}$ cycloalkyl which is optionally substituted with 1 to 4 groups independently selected from the group consisting of halogen, hydroxy, and $C_{1-6}$ alkoxy,
(2) $C_{3-10}$ cycloalkyl group which is optionally substituted with 1 to 5 groups independently selected from the group consisting of (a) to (s) defined in the above group (1), or
(3) 5- to 10-membered heteroaryl group which is optionally substituted with 1 to 5 groups independently selected from the group consisting of (a) to (s) defined in the above group (1);
$W^1$ is a $C_{1-4}$ alkylene group which is optionally substituted with 1 to 4 groups independently selected from the group consisting of halogen, hydroxy, and $C_{1-6}$ alkoxy;
ring $Q^2$ is a benzene ring, pyridine ring, pyrimidine ring, pyridazine ring, or pyrazine ring wherein the benzene ring, pyridine ring, pyrimidine ring, pyridazine ring, and pyrazine ring are each optionally substituted with 1 to 3 groups independently selected from the group consisting of:
(1) halogen,
(2) $C_{1-6}$ alkyl which is optionally substituted with 1 to 4 groups independently selected from the group consisting of halogen, hydroxy, and $C_{1-6}$ alkoxy,
(3) $C_{1-6}$ alkoxy which is optionally substituted with 1 to 3 halogen groups,
(4) hydroxyl, and
(5) cyano;
ring $Q^3$ is a 5-membered heteroaryl ring which is optionally substituted with halogen or $C_{1-6}$ alkyl which is optionally substituted with 1 to 4 groups independently selected from the group consisting of halogen, hydroxy, and $C_{1-6}$ alkoxy.

4. The compound according to claim 3 or a pharmaceutically acceptable salt thereof, wherein ring $Q^1$ is (1) phenyl group which is optionally substituted with 1 to 5 groups selected from the group consisting of:
  (a) halogen atom,
  (b) $C_{1-6}$ alkyl which is optionally substituted with 1 to 3 groups independently selected from the group consisting of halogen, hydroxy and $C_{1-6}$ alkoxy,
  (c) $C_{1-6}$ alkoxy which is optionally substituted with 1 to 3 groups independently selected from the group consisting of halogen, hydroxy and $C_{1-6}$ alkoxy,
  (d) cyano,
  (e) phenyl which is optionally substituted with 1 to 4 groups independently selected from the group consisting of halogen, $C_{1-6}$ alkyl and $C_{1-6}$ alkoxy,
  (f) 5- or 6-membered heteroaryl which is optionally substituted with 1 to 4 groups independently selected from the group consisting of halogen, $C_{1-6}$ alkyl and $C_{1-6}$ alkoxy, and
  (g) phenoxy which is optionally substituted with 1 to 4 groups independently selected from the group consisting of halogen, $C_{1-6}$ alkyl and $C_{1-6}$ alkoxy,
(2) $C_{3-7}$ cycloalkyl group which is optionally substituted with 1 to 4 groups independently selected from the group consisting of (a) to (g) defined in the above group (1), or
(3) pyridyl group which is optionally substituted with 1 to 4 groups independently selected from the group consisting of (a) to (g) defined in the above group (1).

5. The compound according to claim 4 or a pharmaceutically acceptable salt thereof, wherein ring $Q^1$ is phenyl group which is optionally substituted with 1 to 5 groups independently selected from the group consisting of:
  (a) halogen,
  (b) $C_{1-6}$ alkyl which is optionally substituted with 1 to 3 independently selected halogen groups, and
  (c) $C_{1-6}$ alkoxy which is optionally substituted with 1 to 3 independently selected halogen groups.

6. The compound according to claim 1 or a pharmaceutically acceptable salt thereof, wherein $W^1$ is methylene group which is optionally substituted with 1 to 2 independently selected halogen groups, or ethylene which is optionally substituted with 1 to 4 independently selected halogen groups.

7. The compound according to claim 1 or a pharmaceutically acceptable salt thereof, wherein $W^2$-$Cy^1$ is —$NR^{3a}C(O)$-$Cy^1$ or —$C(O)NR^{3a}$-$Cy^1$, wherein $R^{3a}$ is hydrogen or $C_{1-6}$ alkyl.

8. The compound according to claim 7 or a pharmaceutically acceptable salt thereof, wherein $W^2$-$Cy^1$ is —$NR^{3a}C(O)$-$Cy^1$, wherein $R^{3a}$ is hydrogen or $C_{1-6}$ alkyl.

9. The compound according to claim 1 represented by formula (1a):

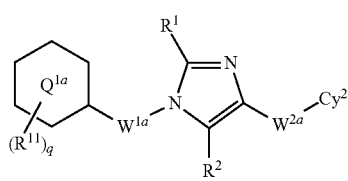

(1a)

or a pharmaceutically acceptable salt thereof, wherein ring $Q^{1a}$ is phenyl, pyridyl, or cyclohexyl;
q is 1, 2, 3, 4 or 5;
$R^{11}$ is, independently when two or more exist,
(1) hydrogen,
(2) halogen,
(3) a $C_{1-6}$ alkyl group which is optionally substituted with 1 to 3 independently selected halogen groups, or
(4) a $C_{1-6}$ alkoxy group which is optionally substituted with 1 to 3 independently selected halogen groups;
$R^1$ and $R^2$ are independently hydrogen, halogen, or $C_{1-6}$ alkyl group which is optionally substituted with 1 to 3 independently selected halogen groups;
$W^{1a}$ is methylene which is optionally substituted with 1 to 2 independently selected halogen groups, or ethylene which is optionally substituted with 1 to 4 independently selected halogen groups;
$W^{2a}$-$Cy^2$ is —$NR^{3a}C(O)$-$Cy^2$ or —$C(O)NR^{3a}$-$Cy^2$ wherein $R^{3a}$ is hydrogen or $C_{1-6}$ alkyl; and
$Cy^2$ is a group of the following formula (21), (22), or (23):

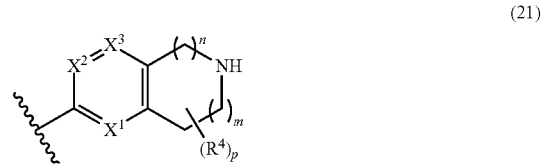

(21)

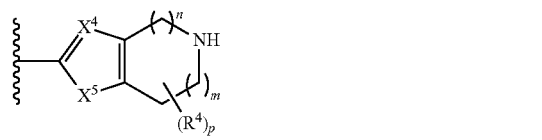

(22)

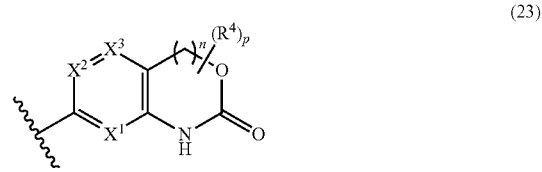

(23)

wherein $X^1$ is N or $CR^{12}$;
$X^2$ is N or $CR^{13}$;
$X^3$ is N or $CR^{14}$;
$X^4$ is N or $CR^{15}$;
$X^5$ is S, O or NH;
provided that $X^1$, $X^2$ and $X^3$ are not simultaneously N;
$R^{12}$, $R^{13}$, $R^{14}$ and $R^{15}$ are independently
(1) hydrogen,
(2) halogen,
(3) a $C_{1-6}$ alkyl group which is optionally substituted with 1 to 3 independently selected halogen groups, or
(4) a $C_{1-6}$ alkoxy group which is optionally substituted with 1 to 3 independently selected halogen groups;
n and m are independently 0, 1 or 2, provided that n and m are not simultaneously 0;
p is 1, 2, 3, 4 or 5; and
$R^4$ is, independently when two or more exist, hydrogen, halogen, or a $C_{1-6}$ alkyl group which is optionally substituted with 1 to 3 independently selected halogen groups.

10. The compound according to claim 9 or a pharmaceutically acceptable salt thereof, wherein ring $Q^{1a}$ is phenyl.

11. The compound according to claim 9 or a pharmaceutically acceptable salt thereof, wherein $W^{2a}$-$Cy^2$ is —$NHC(O)$-$Cy^2$.

12. The compound according to claim 9 or a pharmaceutically acceptable salt thereof, wherein $W^{2a}$-$Cy^2$ is —$C(O)NH$-$Cy^2$.

13. The compound according to claim 9 or a pharmaceutically acceptable salt thereof, wherein Cy² is a group of formula (21) or (23).

14. The compound according to claim 9 or a pharmaceutically acceptable salt thereof, wherein Cy² is a group of formula (22); X⁴ is N or CH; and X⁵ is S.

15. The compound according to claim 1 or a pharmaceutically acceptable salt thereof, wherein R¹ and R² are each hydrogen.

16. The compound according to claim 1 represented by formula (1b):

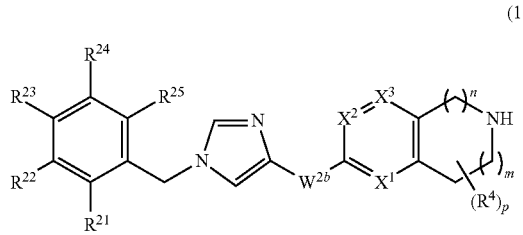

(1b)

or a pharmaceutically acceptable salt thereof, wherein X¹ is N or CR¹²;
X² is N or CR¹³;
X³ is N or CR¹⁴;
provided that X¹, X² and X³ are not simultaneously N;
W²ᵇ is —NHC(O)—, or —C(O)NH—;
R¹², R¹³, R¹⁴, R²¹, R²², R²³, R²⁴, and R²⁵ are independently
(1) hydrogen,
(2) halogen,
(3) a C₁₋₆ alkyl group which optionally substituted with 1 to 3 independently selected halogen groups, or
(4) a C₁₋₆ alkoxy group which optionally substituted with 1 to 3 independently selected halogen groups;
n and m are independently 0, 1 or 2, provided that n and m are not simultaneously 0;
p is 1, 2, 3, 4 or 5; and
R⁴ is, independently when two or more exist, hydrogen, halogen, or a C₁₋₆ alkyl group which is optionally substituted with 1 to 3 independently selected halogen groups.

17. The compound according to claim 16 or a pharmaceutically acceptable salt thereof, wherein R²² is halogen or a C₁₋₆ alkyl group which optionally substituted with 1 to 3 independently selected halogen groups.

18. The compound according to claim 16 or a pharmaceutically acceptable salt thereof, wherein R²² is halogen.

19. The compound according to claim 16 or a pharmaceutically acceptable salt thereof, wherein R²¹, R²³, R²⁴ and R²⁵ are independently
(1) hydrogen,
(2) halogen, or
(3) a C₁₋₆ alkyl group which is optionally substituted with 1 to 3 independently selected halogen groups.

20. The compound according to claim 16 or a pharmaceutically acceptable salt thereof, wherein W²ᵇ is —NHC(O)—.

21. The compound according to claim 16 or a pharmaceutically acceptable salt thereof, wherein W²ᵇ is —C(O)NH—.

22. The compound according to claim 9 or a pharmaceutically acceptable salt thereof, wherein only one of X¹, X² and X³ is N.

23. The compound according to claim 1 or a pharmaceutically acceptable salt thereof, wherein R⁴ is hydrogen.

24. The compound according to claim 1 or a pharmaceutically acceptable salt thereof, wherein n is 1 and m is 1; or n is 2 and m is 0.

25. The compound according to claim 24 or a pharmaceutically acceptable salt thereof, wherein n is 1 and m is 1.

26. The compound according to claim 1 selected from the following compounds or a pharmaceutically acceptable salt thereof:
N-(7-fluoro-1,2,3,4-tetrahydroisoquinolin-6-yl)-1-(3,4,5-trifluorobenzyl)-1H-imidazole-4-carboxamide,
N-(5,6,7,8-tetrahydro-2,7-naphthyridin-3-yl)-1-(3,4,5-trifluorobenzyl)-1H-imidazole-4-carboxamide,
N-(1,2,3,4-tetrahydroisoquinolin-6-yl)-1-(3,4,5-trifluorobenzyl)-1H-imidazole-4-carboxamide,
8-fluoro-N-[1-(3,4,5-trifluorobenzyl)-1H-imidazol-4-yl]-1,2,3,4-tetrahydroisoquinoline-6-carboxamide,
N-[1-(3,4,5-trifluorobenzyl)-1H-imidazol-4-yl]-1,2,3,4-tetrahydroisoquinoline-6-carboxamide,
N-[1-(3,4,5-trifluorobenzyl)-1H-imidazol-4-yl]-5,6,7,8-tetrahydro-2,7-naphthyridine-3-carboxamide,
N-{1-[3-(trifluoromethyl)benzyl]-1H-imidazol-4-yl}-5,6,7,8-tetrahydro-2,7-naphthyridine-3-carboxamide,
N-{1-[3-(trifluoromethyl)benzyl]-1H-imidazol-4-yl}-5,6,7,8-tetrahydro-1,6-naphthyridine-2-carboxamide,
N-[1-(3,4,5-trifluorobenzyl)-1H-imidazol-4-yl]-5,6,7,8-tetrahydro-1,6-naphthyridine-2-carboxamide,
N-[1-(3,4,5-trifluorobenzyl)-1H-imidazol-4-yl]-5,6,7,8-tetrahydro-1,7-naphthyridine-3-carboxamide,
N-{1-[3-(trifluoromethyl)benzyl]-1H-imidazol-4-yl}-5,6,7,8-tetrahydro-1,7-naphthyridine-3-carboxamide,
N-{1-[3-(trifluoromethyl)benzyl]-1H-imidazol-4-yl}-1,2,3,4-tetrahydroisoquinoline-6-carboxamide,
1-(3,4-difluorobenzyl)-N-(5,6,7,8-tetrahydro-2,7-naphthyridin-3-yl)-1H-imidazole-4-carboxamide,
N-[1-(3,5-difluorobenzyl)-1H-imidazol-4-yl]-5,6,7,8-tetrahydro-1,7-naphthyridine-3-carboxamide,
N-[1-(3,4-difluorobenzyl)-1H-imidazol-4-yl]-5,6,7,8-tetrahydro-1,7-naphthyridine-3-carboxamide,
N-{1-[3-(trifluoromethoxy)benzyl]-1H-imidazol-4-yl}-5,6,7,8-tetrahydro-1,7-naphthyridine-3-carboxamide,
N-[1-(3-phenoxybenzyl)-1H-imidazol-4-yl]-5,6,7,8-tetrahydro-1,7-naphthyridine-3-carboxamide,
N-[1-(4-chloro-3-fluorobenzyl)-1H-imidazol-4-yl]-5,6,7,8-tetrahydro-1,7-naphthyridine-3-carboxamide,
N-[1-(3-chloro-5-fluorobenzyl)-1H-imidazol-4-yl]-5,6,7,8-tetrahydro-1,7-naphthyridine-3-carboxamide,
N-{1-[4-fluoro-3-(trifluoromethyl)benzyl]-1H-imidazol-4-yl}-5,6,7,8-tetrahydro-1,7-naphthyridine-3-carboxamide,
N-{1-[4-chloro-3-(trifluoromethyl)benzyl]-1H-imidazol-4-yl}-5,6,7,8-tetrahydro-1,7-naphthyridine-3-carboxamide,
N-{1-[4-(trifluoromethyl)benzyl]-1H-imidazol-4-yl}-5,6,7,8-tetrahydro-1,7-naphthyridine-3-carboxamide,
N-[1-(4-chlorobenzyl)-1H-imidazol-4-yl]-5,6,7,8-tetrahydro-1,7-naphthyridine-3-carboxamide,
N-{1-[3-chloro-5-(trifluoromethoxy)benzyl]-1H-imidazol-4-yl}-5,6,7,8-tetrahydro-1,7-naphthyridine-3-carboxamide,
N-[1-(3-phenoxybenzyl)-1H-imidazol-4-yl]-1,2,3,4-tetrahydroisoquinoline-6-carboxamide,
N-[1-(4-chloro-3-fluorobenzyl)-1H-imidazol-4-yl]-1,2,3,4-tetrahydroisoquinoline-6-carboxamide,
N-[1-(3-chloro-5-fluorobenzyl)-1H-imidazol-4-yl]-1,2,3,4-tetrahydroisoquinoline-6-carboxamide, N-{1-[4-fluoro-3-(trifluoromethyl)benzyl]-1H-imidazol-4-yl}-1,2,3,4-tetrahydroisoquinoline-6-carboxamide, N-{1-[4-chloro-3-(trifluoromethyl)benzyl]-1H-imidazol-4-yl}-1,2,3,4-tetrahydroisoquinoline-6-carboxamide, N-[1-(3-chloro-4-fluorobenzyl)-1H-imidazol-4-yl]-1,2,3,4-tetrahydroisoquinoline-6-carboxamide, N-{1-[4-methyl-3-(trifluoromethyl)benzyl]-1H-imidazol-4-yl}-1,2,3,4-tetrahydroisoquinoline-6-carboxamide, N-{1-[3-fluoro-5-(trifluoromethyl)benzyl]-1H-imidazol-4-yl}-1,2,3,4-tetrahydroisoquinoline-6-carboxamide, N-{1-[3-chloro-5-(trifluoromethoxy)benzyl]-1H-imidazol-4-yl}-1,2,3,4-tetrahydroisoquinoline-6-carboxamide, N-[1-(3,5-dichlorobenzyl)-1H-imidazol-4-yl]-1,2,3,4-tetrahydroisoquinoline-6-carboxamide, and N-[1-(3,4-dichlorobenzyl)-1H-imidazol-4-yl]-1,2,3,4-tetrahydroisoquinoline-6-carboxamide.

27. The compound according to claim 1 selected from the following compounds or a pharmaceutically acceptable salt thereof:

N-(5,6,7,8-tetrahydro-2,7-naphthyridin-3-yl)-1-(3,4,5-trifluorobenzyl)-1H-imidazole-4-carboxamide, 8-fluoro-N-[1-(3,4,5-trifluorobenzyl)-1H-imidazol-4-yl]-1,2,3,4-tetrahydroisoquinoline-6-carboxamide, N-[1-(3,4,5-trifluorobenzyl)-1H-imidazol-4-yl]-1,2,3,4-tetrahydroisoquinoline-6-carboxamide, N-{1-[3-(trifluoromethyl)benzyl]-1H-imidazol-4-yl}-5,6,7,8-tetrahydro-1,6-naphthyridine-2-carboxamide, N-[1-(3,4,5-trifluorobenzyl)-1H-imidazol-4-yl]-5,6,7,8-tetrahydro-1,6-naphthyridine-2-carboxamide, N-[1-(3,4,5-trifluorobenzyl)-1H-imidazol-4-yl]-5,6,7,8-tetrahydro-1,7-naphthyridine-3-carboxamid, and N-{1-[3-(trifluoromethyl)benzyl]-1H-imidazol-4-yl}-5,6,7,8-tetrahydro-1,7-naphthyridine-3-carboxamide.

28. A method for treating cancer which comprises administering a therapeutically effective amount of the compound according to claim 1 or a pharmaceutically acceptable salt thereof to a patient in need thereof.

29. A pharmaceutical composition comprising the compound according to claim 1 or a pharmaceutically acceptable salt thereof and a pharmaceutically acceptable excipient.

30. A compound selected from the following compounds or a pharmaceutically acceptable salt thereof:

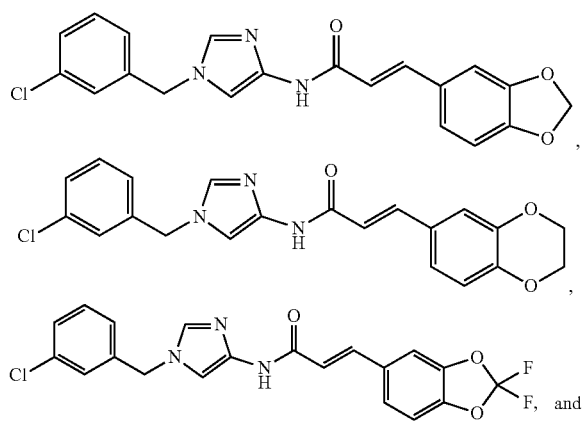
, and

-continued

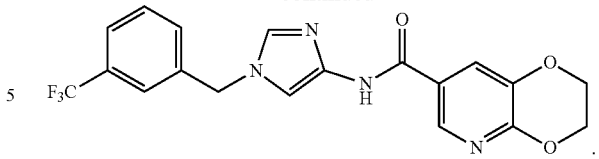
.

31. A method for treating tumor which comprises administering a therapeutically effective amount of the compound according to claim 1 or a pharmaceutically acceptable salt thereof to a patient in need thereof, wherein the tumor is acute leukemia, chronic lymphatic leukemia, chronic myelocytic leukemia, polycythemia vera, malignant lymphoma, myeloma, brain tumor, head and neck cancer, esophageal cancer, thyroid cancer, small cell lung cancer, non-small cell lung cancer, breast cancer, stomach cancer, gallbladder or bile duct cancer, liver cancer, pancreatic cancer, colon cancer, rectal cancer, ovarian cancer, chorioepithelioma, endometrial cancer, cervical cancer, urothelial cancer, renal cell cancer, prostate cancer, testicular tumor, Wilms' tumor, malignant melanoma, neuroblastoma, osteosarcoma, Ewing's sarcoma, or soft tissue sarcoma.

32. A method for treating cancer which comprises administering a therapeutically effective amount of the compound according to claim 1 or a pharmaceutically acceptable salt thereof and another anti-cancer agent selected from the group consisting of an anticancer alkylating agent, an anticancer antimetabolite, an anticancer antibiotic, a plant-based anti-cancer agent, an anticancer platinum coordination compound, an anticancer camptothecin derivative, an anticancer tyrosine kinase inhibitor, a serine-threonine kinase inhibitor, a phospholipid kinase inhibitor, a monoclonal antibody, an interferon, a biological response modifier, a hormone preparation, an immune checkpoint inhibitor, an epigenetics-related molecule inhibitor, a post-translational protein modification inhibitor, and an anti-cancer agent other than the foregoings or a pharmaceutically acceptable salt thereof to a patient in need thereof.

33. A method for treating cancer which comprises administering a therapeutically effective amount of the compound according to claim 26 or a pharmaceutically acceptable salt thereof to a patient in need thereof.

34. A pharmaceutical composition comprising the compound according to claim 26 or a pharmaceutically acceptable salt thereof and a pharmaceutically acceptable excipient.

35. A method for treating tumor which comprises administering a therapeutically effective amount of the compound according to claim 26 or a pharmaceutically acceptable salt thereof to a patient in need thereof, wherein the tumor is acute leukemia, chronic lymphatic leukemia, chronic myelocytic leukemia, polycythemia vera, malignant lymphoma, myeloma, brain tumor, head and neck cancer, esophageal cancer, thyroid cancer, small cell lung cancer, non-small cell lung cancer, breast cancer, stomach cancer, gallbladder or bile duct cancer, liver cancer, pancreatic cancer, colon cancer, rectal cancer, ovarian cancer, chorioepithelioma, endometrial cancer, cervical cancer, urothelial cancer, renal cell cancer, prostate cancer, testicular tumor, Wilms' tumor, malignant melanoma, neuroblastoma, osteosarcoma, Ewing's sarcoma, or soft tissue sarcoma.

36. A method for treating cancer which comprises administering a therapeutically effective amount of the compound according to claim 26 or a pharmaceutically acceptable salt thereof and another anti-cancer agent selected from the group consisting of an anticancer alkylating agent, an anticancer antimetabolite, an anticancer antibiotic, a plant-based anti-cancer agent, an anticancer platinum coordination compound, an anticancer camptothecin derivative, an anticancer tyrosine kinase inhibitor, a serine-threonine kinase inhibitor, a phospholipid kinase inhibitor, a monoclonal antibody, an interferon, a biological response modifier, a hormone preparation, an immune checkpoint inhibitor, an epigenetics-related molecule inhibitor, a post-translational protein modification inhibitor, and an anti-cancer agent other than the foregoings or a pharmaceutically acceptable salt thereof to a patient in need thereof.

* * * * *